US010017586B2

(12) United States Patent
Modahl et al.

(10) Patent No.: US 10,017,586 B2
(45) Date of Patent: Jul. 10, 2018

(54) MONODISPERSE SUBMICRON POLYMER PARTICLES

(71) Applicant: LIFE TECHNOLOGIES AS, Oslo (NO)

(72) Inventors: Grete Modahl, Oslo (NO); Geir Fonnum, Fjellhamar (NO); Astrid Molteberg, Fetsund (NO); Silje Lien, Kloefta (NO); Nini Kjus, Oslo (NO)

(73) Assignee: LIFE TECHNOLOGIES AS, Olso (NO)

( * ) Notice: Subject to any disclaimer, the term of this patent is extended or adjusted under 35 U.S.C. 154(b) by 0 days.

(21) Appl. No.: 15/453,750

(22) Filed: Mar. 8, 2017

(65) Prior Publication Data

US 2017/0218095 A1 Aug. 3, 2017

Related U.S. Application Data

(62) Division of application No. 13/266,910, filed as application No. PCT/EP2010/055874 on Apr. 29, 2010, now abandoned.

(Continued)

(30) Foreign Application Priority Data

Apr. 29, 2009 (GB) .................................. 0907372.7

(51) Int. Cl.
*B32B 5/16* (2006.01)
*B32B 9/00* (2006.01)
(Continued)

(52) U.S. Cl.
CPC .................. *C08F 2/22* (2013.01); *C08J 9/20* (2013.01); *C08J 2325/08* (2013.01)

(58) Field of Classification Search
CPC .... C08C 1/00; C08C 1/02; C08C 1/04; C08C 2/06; C08C 2/02; C08C 2/00; C08C 4/00; Y02P 20/125
(Continued)

(56) References Cited

U.S. PATENT DOCUMENTS 4,530,956 A 7/1985 Ugelstad et al.
4,654,267 A 3/1987 Ugelstad et al.
(Continued)

FOREIGN PATENT DOCUMENTS

EP 0003905 9/1979
EP 0523116 6/1996
(Continued)

OTHER PUBLICATIONS

Ahmad, H. et al., "Preparation of Sub-micron to Micron-sized Di-functional Polymer Particles and Their Characterization", *Malaysian Polymer Journal*, vol. 5, No. 2, 2010, pp. 181-192.
(Continued)

*Primary Examiner* — William K Cheung

(57) ABSTRACT

This invention relates to monodisperse cross-linked polymer particles, comprising particles with a substantially smooth outer surface and an average diameter of less than 1 µm, wherein the particles are solid or porous, and wherein the coefficient of variation (CV) % of the particles, when measured by CPS disk centrifugation analysis, is less than 15%. These monodisperse cross-linked polymer particles may comprise magnetic material and are useful in various application. This invention also relates to monodisperse polymer particles for use as seed particles in the Ugelstad process.

17 Claims, 25 Drawing Sheets

Related U.S. Application Data

(60) Provisional application No. 61/174,407, filed on Apr. 30, 2009.

(51) Int. Cl.
  *C08F 4/46* (2006.01)
  *C08F 2/22* (2006.01)
  *C08J 9/20* (2006.01)

(58) Field of Classification Search
  USPC .......................... 428/407, 402, 403; 526/181
  See application file for complete search history.

(56) References Cited

U.S. PATENT DOCUMENTS

| | | |
|---|---|---|
| 5,147,937 A | 9/1992 | Frazza et al. |
| 5,234,809 A | 8/1993 | Boom et al. |
| 5,496,897 A | 3/1996 | Yoshimatsu et al. |
| 5,750,341 A | 5/1998 | Macevicz |
| 5,969,119 A | 10/1999 | Macevicz |
| 5,972,363 A | 10/1999 | Clikeman et al. |
| 6,197,907 B1 | 3/2001 | Yoshida et al. |
| 6,232,465 B1 | 5/2001 | Hiatt et al. |
| 6,306,597 B1 | 10/2001 | Macevicz et al. |
| 6,559,217 B1 | 5/2003 | Nordal et al. |
| 6,664,079 B2 | 12/2003 | Ju et al. |
| 6,710,118 B2 * | 3/2004 | Koppers .............. C08F 212/04 428/510 |
| 7,057,026 B2 | 6/2006 | Barnes et al. |
| 7,217,762 B1 | 5/2007 | Jorgedal et al. |
| 2002/0173610 A1 | 11/2002 | Aert et al. |
| 2005/0147822 A1 | 7/2005 | Fonnum et al. |
| 2006/0035388 A1 | 2/2006 | Yoshinaga et al. |
| 2006/0188905 A1 | 8/2006 | Fonnum et al. |
| 2007/0265390 A1 | 11/2007 | Jorgedal et al. |
| 2008/0268552 A1* | 10/2008 | Geiger ............. G01N 33/54346 436/534 |
| 2009/0053690 A1 | 2/2009 | Schwartz |
| 2009/0099027 A1 | 4/2009 | Greiner et al. |
| 2010/0163778 A1 | 7/2010 | Zhang et al. |

FOREIGN PATENT DOCUMENTS

| | | |
|---|---|---|
| EP | 0190886 | 8/1996 |
| EP | 2000484 | 12/2008 |
| JP | 2005232426 | 9/2005 |
| JP | 2009057479 | 3/2009 |
| KR | 10-2007-0050530 | 11/2005 |
| WO | WO1994/007923 | 4/1994 |
| WO | WO1997/012921 | 4/1997 |
| WO | WO2000/024005 | 4/2000 |
| WO | WO2000/061647 | 10/2000 |
| WO | WO2000/61648 | 10/2000 |
| WO | WO2004/053490 | 6/2004 |
| WO | WO2005/015216 | 2/2005 |
| WO | WO2006/075185 | 7/2006 |
| WO | WO2006/084132 | 8/2006 |
| WO | WO2008/079905 | 7/2008 |
| WO | WO2009/026546 | 2/2009 |

OTHER PUBLICATIONS

GB 0907372.7, , "Search Report dated Dec. 14, 2009".
GB 0907372.7, , "Search Report dated Sep. 9, 2009".
GB 1018544.5, , "Further Search Report dated Jul. 7, 2011".
GB 1018544.5, , "Search Report dated Mar. 1, 2011", 8.
Gugliotta, et al., "Emulsion polymerization of styrene. Use of n-nonyl mercaptan for molecular weight control", *Polymer* vol. 42, Issue 7, Mar. 2001, 2719-2726.
Hanton, , "Mass Spectrometry of Polymers and Polymer Surfaces", *Chemical Reviews*, vol. 101, Issue 2,, Jan. 27, 2001, 527-570.
Harrison, et al., "Techniques for the Analysis of Cross Linked Polymers", *Polymer Reviews*, vol. 25, Issue 4,, 1985, 481-549.
Kim, J et al., "Monodisperse polymer particles synthesized by seeded polymerization techniques", *Journal of Industrial and Engineering Chemistry*, vol. 14, 2008, pp. 1-9.
Liu, "Monodisperse Polystyrene Nanospheres with Ultrahigh Surface Area: Application for Hydrogen Storage", *Macromolecular Chemistry and Physics*, vol. 211, Issue 9,, May 3, 2010, 1012-1017.
MacIntyre, et al., "Synthesis of Ultrahigh Surface Area Monodisperse Porous Polymer Nanospheres", *Macromolecules*, vol. 39, 2006, 5381-5384.
Mendoza, et al., "Kinetics of the Styrene Emulsion Polymerization Using n-Dodecyl Mercaptan as Chain-Transfer Agent", *Journal of Polymer Science, Part A: Polymer Chemistry*, vol. 38, Issue 24, Dec. 15, 2000, 4490-4505.
Okubo, M. et al., "Production of submicron-size monodisperse polymer particles having aldehyde groups by seeded aldol condensation polymerization", *Colloid Polym Sci*, vol. 271, 1993, pp. 109-113.
Qian, et al., "Rapid Polymer Identification by In-Source Direct Pyrolysis Mass Spectrometry and Library Searching Techniques", *Analytical Chemistry*, vol. 68, Issue 6,, Mar. 15, 1996, 1019-1027.
Römpp, , "Vinylpyridine", https://roempp.thieme.de/roempp4.0/do/data/RD-22-00837, 2016, 1 page.
Schwartz, et al., "High Density Single Molecule Surface Patterning With Colloidal Epitaxy", *Applied Physics Letters*, vol. 91, Issue 8,, Aug. 21, 2007, 083902.
Stoffelbach, et al., "Surfactant-Free, Controlled/Living Radical Emulsion Polymerization in Batch Conditions Using a Low Molar Mass, Surface-Active Reversible Addition-Fragmentation Chain-Transfer (RAFT) Agent", *Macromolecules* vol. 41, Issue 21, Oct. 8, 2008, 7850-7856.
Ziegler, et al., "Silicon-Based Polymer Science: A Comprehensive Resource", *American Chemical Society*, Washington, DC, Advances in Chemistry Series 224, 1990.

* cited by examiner

50% v% toluene

70% v% toluene

MONODISPERSE SUBMICRON POLYMER PARTICLES

CROSS-REFERENCE TO RELATED APPLICATIONS

This application is a Divisional Application of U.S. Ser. No. 13/266,910, filed Feb. 22, 2012, which is a National Phase Application under 35 U.S.C. § 371 of PCT Application Serial No. PCT/EP2010/055874, filed Apr. 29, 2010, which claims priority to U.S. provisional Application Ser. No. U.S. 61/174,407, filed Apr. 30, 2009, and also claims priority to GB patent Application No. 0907372.7 filed Apr. 29, 2009, the entire contents of which are incorporated herein by reference.

This invention relates to monodisperse polymer particles useful in biological assays and other applications. It also relates to processes for preparing such particles, intermediates used in such processes and methods of using the particles, as well as other subject matter.

BACKGROUND

A common reaction for making polymers is free radical polymerisation, which is used to make polymers from unsaturated monomers, for example styrene and/or acrylates. Free radical polymerisation may be performed by emulsion polymerisation or suspension polymerisation. Emulsion polymerisation is the standard process for production of polymer particles in sizes around 100-500 nm. The product is often called a latex and is the main component of water based paints. In emulsion polymerisation unsaturated monomers are, as just mentioned, converted to polymers by the use of free radical polymerisation. Typically the polymerisation is carried out in water and the monomers have a low water solubility.

In a typical procedure, a monomer such as styrene, for example, is mixed with water and surfactants and the mix is stirred to make relatively large styrene droplets (1-10 µm). A water soluble initiator is added. The initiator decomposes to two radicals and starts reacting with the monomers that have been solubilised in the water phase. In the case of styrene, the growing chain soon becomes water insoluble and the molecules aggregate to nanometer-sized particles. If the initiation phase is short the resulting particles can be monosized.

The particles then grow by the following mechanism: The monomers diffuse through the water phase into the polymer particles. The polymerisation in the particles is initiated by the adsorption of growing polymers from the water phase. Since the particles are so small only one radical can survive in the particle at the same time, and the adsorption of a second growing chain will therefore result in termination. The polymerisation stops when the monomer in the large droplets has diffused into the growing particles and polymerised.

Emulsion polymerisation is dependent on the transfer of monomer from the large droplets to the smaller particles and radical adsorption. If a high amount of crosslinking monomer is used—that is above 10-15%—the small particles will be crosslinked and the polymerisation does not continue.

Emulsion polymerisation is used to produce monosized seed particles as starting material for the Ugelstad two step swelling process.

This application teaches a method which is able to produce submicron highly crosslinked polymer particles which it is believed cannot be obtained by emulsion polymerisation. It is known to produce cross-linked porous or solid monodisperse polymer particles by a two stage process, named the Ugelstad process after the late Professor John Ugelstad, which is described for example in EP-B-3905 (Sintef) and U.S. Pat. No. 4,530,956 (Ugelstad). An improved Ugelstad process is described in WO 00/61647. In the Ugelstad process, seed particles, suitably made by emulsion polymerisation, are converted in two steps into monodisperse particles by seeded suspension polymerisation. In a first step, the seed particles are swollen by making a fine (e.g. submicron) aqueous emulsion of a relatively low molecular weight water-insoluble substance and then adding a water-miscible organic solvent (e.g. acetone) so that the water-insoluble substance diffuses into the seed particles. It is convenient for the water-insoluble substance to be a heat-activated polymerisation initiator. In a second step, the solvent is then removed, locking the water-insoluble substance in the seed particles, and the seed particles take up a large quantity of monomer and also a cross-linker, driven by an increase in entropy when the monomer and cross-linker diffuse into the seed particles and dilutes the water-insoluble substance. In practice, after the seed particles have been swollen and absorbed the water-insoluble substance, the dispersion containing them is typically contacted with an aqueous emulsion containing the monomer and cross-linker; the amount of water is chosen to be sufficient for the water to act to remove the water-miscible solvent by dilution and the monomer is driven into the seed particles. The seed particles swell and, following initiation of polymerisation, e.g. by heating to activate the initiator, larger polymer particles are produced. The Ugelstad process therefore comprises making seed particles by emulsion polymerisation and expanding the seed particles by suspension polymerisation. The smallest monodisperse particles described in the aforementioned prior art have an average diameter of 1 µm.

A porogen may be contacted with the seed particles in the final swelling and polymerisation stage in order to make the particles porous. A porogen is an organic liquid which does not participate in the polymerisation reaction. It may be a good solvent for the polymer in which case it will make small pores, or a poor solvent for the polymer, in which case it will form large pores. The present inventors have not been able to control the pore morphology of submicron beads to provide a smooth outer surface by selection of porogens.

In a simplified version of the Ugelstad process, the enhanced capacity for swelling may be achieved simply by the use of oligomeric seed particles, e.g. where the oligomer weight average molecular weight corresponds to up to 50 monomer units (a molecular weight of about 5000 in the case of polystyrene).

Conveniently, a very fine submicron (e.g. 0.05-0.5 µm) stable oil-in-water emulsion can be made if there is used as the emulsifier a combination of a water-soluble surfactant and a less water soluble organic compound. The surfactant is usually ionic but alternatively may be non-ionic.

Prior art Ugelstad methods described above do not provide smooth monodisperse porous particles at small particle sizes. In particular, the prior art methods do not produce smooth particles at the lower size limits. Instead, the outer surface of these small porous particles would be irregular and, for example appear rough or knobbly when viewed at a magnification of e.g. 10,000, e.g. when compared to larger particles. This rough appearance is caused by the morphology of the pores, e.g. excessive pore size.

BRIEF SUMMARY OF THE DISCLOSURE

The invention is in part based on an appreciation that smaller particles than previously made by the Ugelstad process would be expected to increase the sensitivity and reproducibility of assays using them, as compared to larger particles (on a per gram basis). For example when compared to particles of greater than 1 μm diameter submicron particles provide many more particles per gram (FIG. 1), leading to increased surface area and better statistics for small samples. Smaller particles would significantly reduce the amount of biological material required for a biological assay because less volume will be occupied by the particle itself. In addition, submicron particles have application in micro- and nano-fluidics and other nanotechnology areas.

Polymer particles may have an irregular shape, with a surface which appears rough or knobbly under magnification, for instance when viewed under a magnification of 10,000 with a scanning electron microscope. It has further been appreciated that for some applications it would be beneficial to provide a technique for preparing particles having a surface which gives an overall smooth appearance to the particles; such particles have an appearance more of regular spheres than irregular shapes.

It has thus been appreciated that smooth polymer particles have advantages when compared to polymer particles with an irregular shape. One advantage is that where the particles are magnetic, smooth particles provide a uniform magnetic signal in all directions, unlike irregular particles. This provides for a more consistent performance when exposed to a magnetic field. A further advantage of smooth particles is that all of the outer surface is readily accessible, e.g. to a solution. This advantage is particularly important where the outer surface is functionalised, for example with antibodies. Antibodies or other ligands attached to any part of the surface of a smooth particle are able to interact with binding partners present in a solution, potentially providing a sensitive and reproducible assay. Antibodies or other ligands attached to the surface of a rough polymer particle can be located at sites with limited access to the solution, reducing the sensitivity and/or reproducibility of the assay.

The present invention is believed to enrich the field of polymer particles and the technology of their manufacture in a number of ways. Thus, the invention provides novel monodisperse submicron polymer particles having characteristics which it is believed cannot be obtained repeatedly, if at all, by emulsion polymerisation; such characteristics may include one, two, three, four or five of: high cross-linking; porosity; morphology, swelling characteristics, and magnetism (which may be implemented by the incorporation of magnetic particles). The invention includes within its ambit monodisperse submicron polymer particles having characteristics which it is believed could not previously be obtained by Ugelstad polymerisation; such characteristics may include one of more of morphology (in particular porous particles which appear smooth or spherical to the eye when viewed at a scanning electron microscope magnification of 10,000) and size. It will be appreciated therefore that certain implementations of the invention embrace monodisperse submicron particles having characteristics which it is believed cannot be obtained by previous processes for making polymer particles.

The invention also enriches polymer particle technology with a variant of the Ugelstad process which is capable of making the polymer particles described herein. The invention also provides a novel seed particle useful in the Ugelstad process to control the pore size and hence surface smoothness of the end product particles. In this regard, aspects of the invention are predicated on a finding that the pore size of the end product particles may be controlled by controlling the size of the polymer molecules forming the seed particle.

The products, processes and uses of the invention are not limited to the subject matter just-mentioned but are, without limitation, described more fully in the following description and claims and illustrated by the accompanying drawings.

In accordance with one aspect of the present invention there are provided monodisperse, cross-linked submicron polymer particles, i.e. monodisperse particles having an average diameter of less than 1 μm. ("Submicron" means less than 1 μm.)

The particles may be magnetic. The invention includes monodisperse magnetic polymer particles comprising a matrix polymer and magnetic particles, the particles having an average diameter of less than 1 μm. In one embodiment, the magnetic particles are superparamagnetic crystals and in another embodiment they are ferromagnetic, e.g. the magnetic particles may be ferrimagnetic or superparamagnetic iron oxide crystals.

Another aspect of the invention resides in monodisperse, cross-linked polymer particles having a smooth outer surface.

The invention includes monodisperse, cross-linked submicron polymer particles having a smooth outer surface.

As explained in more detail below, "monodisperse" refers herein to particles having a low coefficient of variation (CV) of a specific parameter (e.g. particle diameter), for example a CV of less than 20% and is particular of less than 15%, e.g. of less than 10% and sometimes of less than 5%.

The invention includes within its scope both porous and solid particles. So-called "solid" particles may have very low porosity, as is known in the art, and are alternatively called "compact" particles.

One class of submicron particles disclosed herein are monodisperse and porous. These particles may have specified surface characteristics. In one sub-class the surface is smooth. In another sub-class, the specific surface area of the particles is from 300 $m^2/g$ to 700 $m^2/g$, when measured by gas absorption analysis.

Further included in the invention are monodisperse polymer particles useful as seed particles for making the described submicron particles, wherein the seed particles have an average diameter of from 50 nm to 200 nm and wherein the polymer has a mean weight average molecular weight of more than 1,000 and less than 70,000, when measured by gel permeation chromatography. In embodiments the average diameter is from 50 nm to less than 200 nm.

In another aspect, there is provided a process for the preparation of monodisperse polymer particles for use as seed particles in seeded suspension polymerisation, the process comprising an emulsion polymerisation process comprising:

forming an aqueous dispersion comprising an ethylenically unsaturated monomer and a water soluble polymerisation initiator; and mixing until the commencement of particle nucleation; characterised in that:

the aqueous dispersion comprises a surfactant and in that a chain transfer agent is added after the commencement of particle nucleation, such that the polymerisation forms monodisperse seed particles having an average diameter of from 50 nm to 200 nm and, when measured by gel permeation chromatography, the polymer has a mean weight average molecular weight of more than 1,000 and less than 70,000. In embodiments, the average diameter of the seed particles is from 50 nm to less than 200 nm.

The invention includes the use of the mentioned monodisperse seed particles as seed particles in an Ugelstad process. In this way, the seed particles may be used as an intermediate in the preparation of submicron and/or smooth polymer particles described herein.

The Ugelstad process may comprise:

(i) forming an aqueous dispersion comprising
the monodisperse seed particles,
finely divided droplets comprising an organic compound of molecular weight below 5,000 and water solubility at 25° C. of less than $10^{-2}$ g/L, and
an organic solvent in which the organic compound is soluble, the organic solvent being optional when the polymer forming the seed particles has an average molecular weight which corresponds to up to 50 monomer units;

(ii) allowing the organic compound to diffuse into the monodisperse seed particles, causing the seed particles to become activated;

(iii) removing the organic solvent, where present, from inside the seed particles, and contacting the activated seed particle with an aqueous vehicle containing a monomer, for example one that is at least 10 times more soluble in water than the organic compound, and a crosslinker;

(iv) allowing the monomer to diffuse into the activated seed particles to form an aqueous dispersion of swollen seed particles; and (v) initiating polymerisation of the monomer in the swollen seed particles.

The invention includes particles which have been obtained by the processes described in this specification.

The invention also includes particles having the characteristics of particles obtained by the methods disclosed herein; whilst such particles are obtainable by the processes described herein, they are characterized solely by their properties and not by their method of manufacture and, accordingly, the scope of protection of claims directed to particles specified by their characteristics is determined solely by the characteristics of the particles to the exclusion of their actual method of manufacture.

BRIEF DESCRIPTION OF THE DRAWINGS

Embodiments of the invention are further described hereinafter with reference to the accompanying drawings, in which.

DETAILED DESCRIPTION

Figure 1:
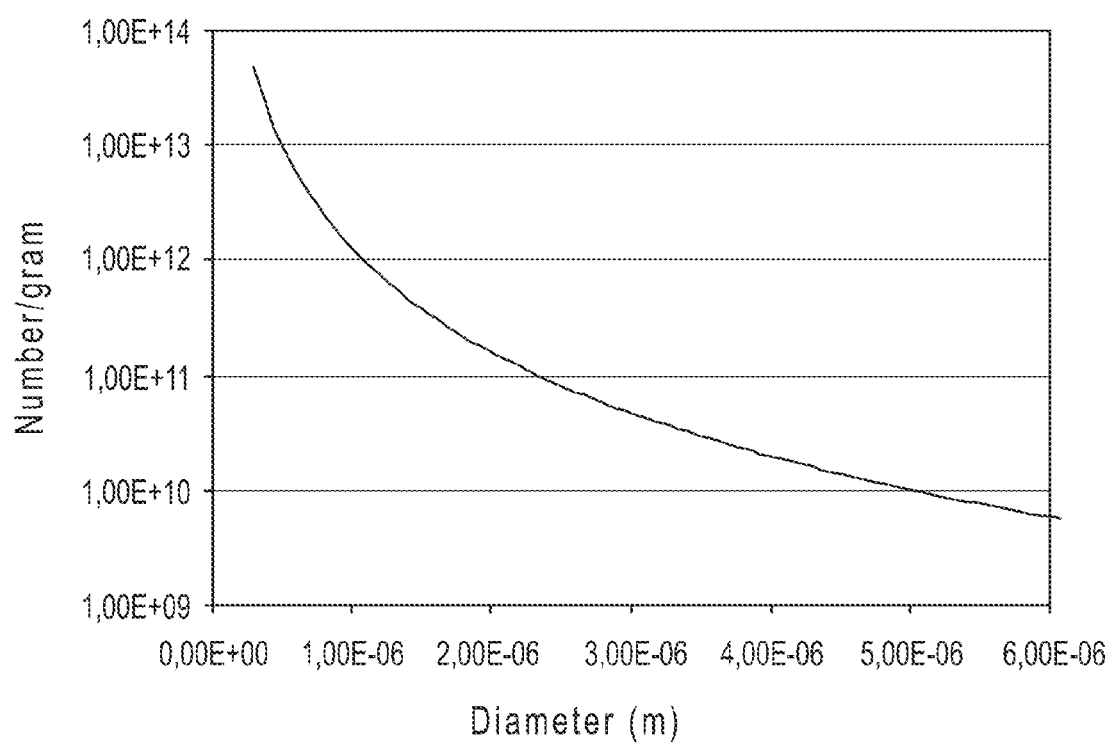
FIG. 1 is a graph indicating the relationship between bead number per gram and diameter for beads of the disclosure having a particle density of 1.5 g/cm³.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

All publications, patent applications, patents, and other references mentioned herein are incorporated by reference in their entirety. In case of conflict, the present specification, including definitions, will control.

The present invention provides novel polymer particles and a modified Ugelstad process by which the novel particles may be prepared. It also provides seed particles for use in the modified Ugelstad process and methods of using the polymer particles which may be obtained by the modified Ugelstad process.

The Ugelstad process described herein involves, therefore, two different particles, namely a seed particle which is subjected to a swelling and polymerisation process to form a polymer particle. The terms "seed particle" and "polymer particle" are therefore used herein as follows:

"Seed particle" means a particle obtainable by emulsion polymerisation and used as an intermediate in the modified Ugelstad process.

"Polymer particle" refers to a particle which may be made from the seed particle by suspension polymerisation in the modified Ugelstad process described herein.

The mention in this specification of "average" diameters refers to the z-average diameter, e.g. the z-average diameter measured by photon correlation spectroscopy. However, across the entire scope of the invention, there are also hereby disclosed embodiments in which the average diameters are the mode diameter, e.g. as measured by CPS disc centrifuge. Across the entire scope of the invention, there are further hereby disclosed embodiments in which the average diameters are the mean diameter. However, some embodiments specify that polymer particles have an average diameter which falls within at least one of the following two categories: (i) a specific range of z-average diameters; (ii) a specific range of mean diameters. Thus, a prescribed class of particles falling within the disclosure requires the particles to have an average diameter which falls within at least one of the following two categories: (i) a z-average diameter of less than 1 μm; (ii) a mean diameter of less than 1 μm; in such a case, a population of particles will fall within the prescribed class if it belongs to category (i) or category (ii) or both categories (i) and (ii).

The Polymer Particle

The invention provides particles which are polymeric and monodisperse. The invention includes embodiments in which the particles are porous and embodiments in which the particles are solid. Particles of the type comprising a polymer shell over liquid core containing magnetic particles are not included in the invention.

The particles may be in a population of at least 100, e.g. at least 1000.

By "monodisperse" is meant that for a plurality of particles (e.g. at least 100, more preferably at least 1000) the particles have a coefficient of variation (CV) of their diameters of less than 20%, for example less than 15%, typically of less than 10% and optionally of less than 8%, e.g. less than 5%. A particular class of polymer particles has a CV of less than 5%. CV when referred to in the claims of this specification is defined as 100 times (standard deviation) divided by average where "average" is mean particle diameter and standard deviation is standard deviation in particle size. The disclosure also includes embodiments where the "average" is either the z-average or mode particle diameter. In accordance with usual practice, CV is calculated on the main mode, i.e. the main peak, thereby excluding minor peaks relating to aggregates. Thus some particles below or above mode size may be discounted in the calculation which may for example be based on about 90% of total particle number (of detectable particles that is). Such a determination of CV is performable on a CPS disc centrifuge.

The invention provides also monodisperse polymer particles which are of submicron size, i.e. have an average diameter of less than 1 μm.

The invention also provides monodisperse polymer particles having a smooth outer surface.

More particularly, the invention provides monodisperse submicron particles having a smooth outer surface. In one embodiment monodisperse submicron particles have an outer surface that has a smooth appearance when viewed at a scanning electron microscope (SEM) magnification of 10,000.

The polymer particles may be produced by an Ugelstad process described later in the specification.

In one embodiment, the invention provides monodisperse cross-linked polymer particles having the following characteristics:
  a substantially smooth outer surface
  a z-average diameter of less than 1 μm
  the particles are porous
  a coefficient of variation (CV) %, when measured by CPS disk centrifugation analysis, of less than 15%.

A second embodiment resides in monodisperse cross-linked polymer particles being a first population of polymer particles and having the following characteristics:
  a substantially smooth outer surface
  a z-average diameter of less than 1 μm
  a coefficient of variation (CV) %, when measured by CPS disk centrifugation analysis, of less than 15%
  a swellability of not more than the swellability of a second population of polymer particles, wherein the second population of particles are reference particles produced by a known Ugelstad process and made of a comparable polymer to the first population, wherein the amount of cross-linker monomer used in the suspension polymerisation stage of the known Ugelstad process is >25% by weight of the total weight of monomers used in the suspension polymerisation stage, optionally wherein the first population of polymer particles are polystyrenic particles and the monomers used in the suspension polymerisation stage in the preparation of the reference particles were styrene and, as a cross-linker monomer, divinylbenzene, the divinylbenzene being in an amount of >25% by weight of the total of styrene plus divinylbenzene.

The invention further provides monodisperse cross-linked polymer particles, having the following characteristics:
- a z-average diameter of less than 1 µm,
- a coefficient of variation (CV) %, when measured by CPS disk centrifugation analysis, of less than 15%
- a specific surface area of from 300 to 700 $m^2/g$ when measured by gas adsorption analysis.

In a further embodiment, the invention provides monodisperse cross-linked polymer particles having the following characteristics:
- a substantially smooth outer surface
- an average diameter which falls within at least one of the following categories (i) a mean diameter of less than 1 µm; (ii) a z-average diameter of less than 1 µm
- the particles are porous
- a coefficient of variation (CV) %, when measured by CPS disk centrifugation analysis, of less than 15%.

A further implementation of the invention resides in monodisperse cross-linked polymer particles being a first population of polymer particles and having the following characteristics:
- a substantially smooth outer surface
- an average diameter which falls within at least one of the following categories (i) a mean diameter of less than 1 µm; (ii) a z-average diameter of less than 1 µm
- a coefficient of variation (CV) %, when measured by CPS disk centrifugation analysis, of less than 15%
- the swellability of a second population of polymer particles, wherein the second population of particles are reference particles produced by a known Ugelstad process and made of a comparable polymer to the first population, wherein the amount of cross-linker monomer used in the suspension polymerisation stage of the known Ugelstad process is >25% by weight of the total weight of monomers used in the suspension polymerisation stage, optionally wherein the first population of polymer particles are polystyrenic particles and the monomers used in the suspension polymerisation stage in the preparation of the reference particles were styrene and, as a crosslinker monomer, divinylbenzene, the divinylbenzene being in an amount of >25% by weight of the total of styrene plus divinylbenzene.

The invention further provides monodisperse cross-linked polymer particles, having the following characteristics:
- an average diameter which falls within at least one of the following categories (i) a mean diameter of less than 1 µm; (ii) a z-average diameter of less than 1 µm,
- a coefficient of variation (CV) %, when measured by CPS disk centrifugation analysis, of less than 15%
- a specific surface area of from 300 to 700 $m^2/g$ when measured by gas adsorption analysis.

Reverting now to the polymer particles, this specification discloses cross-linked polymer particles. It is a characteristic of cross-linked particles that, when placed in a good solvent for the polymer, the particles swell instead of dissolving. By way of example, toluene and THF (tetrahydrofuran) are good solvents for styrene polymers, whilst THF is also a good solvent for acrylic polymers. Included in the disclosure are polymer particles comprising a cross-linked polymer obtainable by a process calculated to provide at least 2% cross-linking.

The level of cross-linking in a polymer particle made by the Ugelstad process can be expressed as the percentage by weight (% wt) of cross-linker monomer included in the total monomer used in the suspension polymerisation. Thus, where the monomers used in the suspension polymerisation are, for example, styrene and divinylbenzene (DVB) the percentage of DVB (the cross-linker monomer) is calculated as weight percent based upon the total weight of DVB plus styrene. Typical levels of cross-linking include >10% wt cross-linker, for example >15% wt cross-linker, or >20% wt cross-linker, e.g. >25% wt cross-linker, levels which, e.g. are suitable for non-porous (i.e. solid) particles. The level of cross-linking may also be, for instance 20-70% wt cross-linker, for example 30-60% wt cross-linker, e.g. 40-50% wt cross-linker, levels which, e.g. are suitable for porous particles. As stated above, cross-linked particles swell when placed in a good solvent for the polymer. The amount of swelling, e.g. measured as an increase in diameter, is related to the level of cross-linking. Particles with a higher degree of cross-linking will typically swell less than particles made from a similar polymer, but with a lower degree of cross-linking. This property can be used to determine the relative level of cross-linking in a sample of polymer particles by comparing the sample with a series of standards of known, different levels of cross-linking. For example, it may be determined whether a sample of particles have a degree of cross-linking exceeding 25% by comparing their swellability with that of reference particles made of a comparable polymer and prepared using 25% cross-linker as described above. In order to provide chemically comparable reference particles, the sample of particles (or, more precisely, a specimen from the sample) is analysed to determine what class of polymer the sample is made of. Suitable analytical techniques are mentioned in more detail later in this specification and may include mass spectrometry, where pyrolysis mass spectrometry is especially useful to determine polymer class of cross linked polymers. FTIR and NMR may also be used in the polymer analysis. The reference particles and the test particles suitably have substantially similar average diameters, for example substantially similar z-average diameters, e.g. the reference particles may have the same average diameter as the test particles ±5%, e.g. ±2%.

In some instances, polystyrenic test particles have their cross-linking compared with a reference population. The identity of the test particles as polystyrenic may be known or determined by analysis. The reference particles are made by an Ugelstad process in which the monomers used in the suspension polymerisation stage are styrene and, as a crosslinker, divinylbenzene, the divinylbenzene being in a known amount, e.g. of 25% by weight of the total of styrene plus divinylbenzene. The reference particles and the test particles suitably have substantially similar average diameters. The test particles and the reference particles are contacted with a swelling agent, i.e. a suitable solvent, and allowed to swell. The swelling (increase in diameter) of the test particles is compared with that of the reference particles and, if it is found to be less than that of the reference particles, then the degree of cross-linking is deduced to be higher than in the reference particles, e.g. higher than 25%. Particles made of any particular class of polymer will swell different amounts with different solvents. It is advantageous to select a solvent which produces a relatively high degree of swelling, and this may be selected empirically. In the case of polystyrenic particles, toluene may be used as the swelling agent.

The invention therefore includes embodiments of the polymer particles wherein the polymer particles constitute a first population of particles and have the swellability of a second population of polymer particles, wherein the second population of particles are reference particles produced by a known Ugelstad process and made of a comparable polymer to the first population, wherein the amount of cross-linker monomer used in the suspension polymerisation stage of the known Ugelstad process is >25% by weight of the total weight of monomers used in the suspension polymerisation stage, optionally wherein the first population of polymer particles are polystyrenic particles and the monomers used in the suspension polymerisation stage in the preparation of the reference particles were styrene and, as a crosslinker monomer, divinylbenzene, the divinylbenzene being in an amount of >25% by weight of the total of styrene plus divinylbenzene. The amount of the cross-linker monomer used in said suspension polymerisation stage may be 30-60%, optionally 40-50%.

The particles suitably comprise addition polymer made by polymerising one or more ethylenically unsaturated monomers. In particular, the monomers may be vinylic, for example a styrenic monomer or an acrylic monomer. Styrenic monomers may be mentioned in particular. Suitable monomers include styrene, methyl methacrylate, methacrylic acid, hydroxyethyl methacrylate, glycidyl methacrylate, butylmethacrylate, acrylic acid, ethyleneglycol dimethacrylate, trimethylolpropane trimethacrylate, trimethylol triacrylate, pentaerythritol tetraacrylate and other acrylic or methacrylic monomers. Cross-linking may be achieved by incorporating a cross-linker comprising two vinyl groups as a comonomer, for example divinylbenzene or ethyleneglycol dimethacrylate. The invention includes the use of a combination of cross-linkers. As a particular monomer may be mentioned styrene, for which divinylbenzene is a suitable cross-linker. In some embodiments, cross-linker may include compounds in which the number of ethylenic double bonds is greater than two, e.g. three.

The described Ugelstad processes include polymerisation reactions which consist of free radical polymerisation of unsaturated monomers. The disclosure therefore includes polymer particles wherein the polymer (the matrix polymer) is derived from radical polymerisation of unsaturated monomers. Cross-linking, therefore, is obtained by incorporation of cross linkers which comprise two ethylenic double bonds (as mentioned elsewhere in this specification, the cross-linker preparation may include molecules in which the number of ethylenic double bonds is more than two, e.g. three), and the polymer particles contain the residue of such cross-linkers incorporated in the polymer network. An alternative cross-linking method which has been used in the manufacture of polymer particles is Lewis-acid catalysed Davankov-type crosslinking which is used in the case of suspension-polymerised particles. In the Davankov method, particles are made by suspension polymerisation using vinylbenzyl chloride (VBC) as one of the monomers. After the particles have been made, they are cross-linked in a separate reaction by combining the particles with $FeCl_3$, which catalyses coupling of a pendant —$CH_2Cl$ group of a former VBC molecule now incorporated in a polymer chain with a neighbouring phenyl group, so as to form a methylene bridge between the two phenyl groups: -Ph-$CH_2$-Ph-. It will be appreciated that it is inherent in particles obtainable by the Ugelstad process that they are free of such -Ph-$CH_2$-Ph- fragments containing methylene-bridged benzene rings, and this provides a way of distinguishing between suspension polymerisation particles made using Davankov cross-linking and Ugelstad particles. It is envisaged that the presence or absence of such -Ph-$CH_2$-Ph- fragments may be determined by one or more analytical techniques, for example NMR or mass spectrometry, particularly NMR. The disclosure therefore includes within its scope monodisperse submicron particles free of -Ph-$CH_2$-Ph- fragments. Particles made by the Ugelstad process may be free of chlorine when subjected to elemental analysis whereas it is believed that particles made using the Davankov process will contain residual chlorine in unreacted —$CH_2Cl$ groups. The disclosure therefore includes within its scope monodisperse submicron particles free of chlorine.

The polymer network produced by Davankov crosslinking of suspension polymerised particles is therefore different from that which results from Ugelstad polymerisation. Such structural differences are reflected in physico-chemical properties, for example in relation to solvent uptake and swelling properties. Thus, polymer particles made by suspension polymerisation to form intermediate gel-type particles followed by Davankov crosslinking show a much higher degree of swellability than Ugelstad particles, resulting in large differences of swelling and solvent uptake between different solvents. Where the polymer particles may be used in procedures which require switching between solvents, e.g. between aqueous and organic solvents (e.g. hydrocarbon solvent), such sharp differences of behaviour are disadvantageous.

The submicron particles of the invention may have an average diameter of at least 200 nm, e.g. at least 300 nm, optionally at least 400 nm, as in the case of particles having a diameter of at least 450 nm.

The submicron polymer particles may have an average diameter of no more than 900 nm, optionally no more than 700 nm, e.g. of no more than 600 nm, as in the case of particles having a diameter of no more than 500 nm.

The invention includes a class of polymer particles having average diameters of from 400 nm to 800 nm, e.g. 450 nm to 700 nm. Particular polymer particles have an average diameter of from 450 nm to 650 nm, e.g. 450 nm to 550 nm. In embodiments, the polymer particles may have an average diameter of from 200 nm, e.g. 300 nm and optionally 400 nm, to 450 nm.

The size and size distribution of seed particles may be determined as described below under the heading "analytical methods".

One class of polymer particles is porous. Another class of polymer particles is non-porous. The porous particles and, independently, the non-porous particles may have average diameters as just indicated.

The disclosure includes porous polymer particles having a specific surface area of from 100 to 700 $m^2/g$, for example from 300 to 600 $m^2/g$, or from 400 to 600 $m^2/g$, e.g. from 450 to 550 $m^2/g$. The specific surface area values are determined by gas adsorption analysis.

The disclosure includes porous polymer particles having a ratio of specific surface area, as measured by gas adsorption analysis, to theoretical specific surface area for a compact particle, of at least 10:1, for example of from 10:1 to 150:1, e.g. from 10:1 to 120:1 as in the case of 10:1 to 110:1. The ratio may be at least 20:1 and is optionally at least 50:1 e.g. at least 80:1. Thus, the ratio may be from 20:1 or 50:1 to 150:1, whilst in other embodiments it is from 20:1 to 120:1 or alternatively from 50:1 to 120:1. In some embodiments, the ratio is from 80:1 to 150:1, e.g. from 80:1 to 120:1, as in the case of 80:1 to 110:1.

The disclosure includes magnetic polymer particles having a specific surface area of greater than 30 m²/g, for example greater than 35 or 40 m²/g. The specific surface area may for example be from greater than 30 m²/g (e.g. greater than 40 m²/g) to 100 m²/g, for example to 90 m²/g; in some embodiments the specific surface area does not exceed 80 m²/g and in particular embodiments it does not exceed 70 m²/g. Particles having such properties are obtainable by forming porous particles by the novel methods described herein and then incorporating magnetic material in the pores and coating the particles.

The disclosure includes magnetic polymer particles having a ratio of specific surface area, as measured by gas adsorption analysis, to theoretical specific surface area for a compact particle, of at least 2:1, for example of from 2:1 to 20:1, e.g. from 2:1 to 18:1 as in the case of 2:1 to 16:1. The ratio may be at least 3:1 and is optionally at least 4:1. Thus, the ratio may be from 3:1 or 4:1 to 20:1, whilst in other embodiments it is from 3:1 to 16:1 or alternatively from 4:1 to 16:1. In some embodiments, the ratio is from 2:1 to 14:1, e.g. from 3:1 to 14:1.

In the case of non-porous polymer particles, the disclosure includes particles having a specific surface area of less than 20 m²/g. In one embodiment the non-porous particles have a specific surface area of from 2 to 20 m²/g, particularly of from 5 to 20 m²/g, e.g. from 6 to 20 m²/g. In another embodiment, the specific surface area is from 2 to 10, e.g. 2 to 8 m²/g. By way of example, particles having a density of 1.05 g/ml and a diameter of from 900 to 300 nm would have a specific surface area of from about 6 to about 20 m²/g. Exemplary specific surface areas are as follows:

Diameter—0.3 μm, density 2.5 g/mL→$A_s$=8.0 m²/g
Diameter—0.9 μm, density 2.5 g/mL→$A_s$=2.7 m²/g
Diameter—0.3 μm, density 1.8 g/mL→$A_s$=11.1 m²/g
Diameter—0.9 μm, density 1.8 g/mL→$A_s$=3.7 m²/g
Diameter—0.3 μm, density 1.05 g/mL→$A_s$=19.0 m²/g
Diameter—0.9 μm, density 1.05 g/mL→$A_s$=5.7 m²/g.

For porous coated magnetic particles the specific surface area will normally be at least twice the specific surface area of the corresponding compact particle having the same mean particle size and density. A typical density for coated magnetic beads is 1.8 g/mL The magnetic beads can have lower density (less magnetic material incorporated) or higher density. In embodiments, a maximum density for a coated magnetic bead would be 2.5 g/mL.

The measurement of specific surface areas is described later in the specification under the heading "analytical methods".

Porous polymer particles may comprise a magnetic material in the pores, for example one or more magnetic materials. By incorporating the magnetic material in the pores, it is possible to retain the smooth appearance of smooth porous submicron particles of the disclosure. The invention is not limited as to the identity of the magnetic material, e.g. the magnetic material may comprise at least one of a paramagnetic, superparamagnetic, ferromagnetic or ferrimagnetic material. One class of polymer particles comprises a paramagnetic material. Another class of polymer particles comprises a superparamagnetic material. A further class of polymer particles comprises ferromagnetic material, ferrimagnetic material or both. At this point, it may be helpful to refresh the reader's knowledge of these terms:

Magnetic: responds to a magnetic field.
Paramagnetic: the magnetic properties are switched off when the magnetic field is removed.
Superparamagnetic: the switching off of the magnetic properties with removal of the magnetic field is very rapid/instant.
Ferromagnetic: all of its magnetic atoms within each domain add a positive contribution to the net magnetization. Retains magnetic properties after an external magnetic field is removed. Above the Curie temperature becomes a paramagnetic material.
Ferrimagnetic: some magnetic atoms within each domain are opposed, but overall exhibits net magnetization. Retains magnetic properties after an external magnetic field is removed. Above the Curie temperature becomes a paramagnetic material.

In one class of embodiments, therefore, the polymer particles described herein comprise superparamagnetic material, particularly superparamagnetic crystals. The superparamagnetic crystals of the polymer particles may be of any material capable of being deposited in superparamagnetic crystalline form on the polymer particles or in the pores thereof, should the particle be porous The magnetic material may comprise, or be, an iron oxide, for example a ferrite such as, e.g. magnetite or maghemite, or a combination thereof. A portion of the iron in the iron oxide, e.g. magnetite or maghemite, may be substituted by (i.e. replaced with) Al, Mn, Ni, Cu, Co, Zn, Ca, Ge, Te, Ti or Sn or a combination thereof. In particular, magnetite or maghemite may have a portion of their iron substituted by Mn. As mentioned, some particles contain a combination of magnetite and maghemite; in this case, either the magnetite or the maghemite, or both, may have such partial substitution of their iron content. Additionally or alternatively, particles of the disclosure may include iron-based metal nanoparticles and FeNi alloy nanoparticles, in either case to increase the saturation magnetization of the particles. Where a portion of the iron is substituted by one or more other elements the total amount substituted can be up to 5 mol %, for example in the range of 0.1 to 5 mol %, for example 0.5 to 4 mol %, e.g. 1 to 3 mol %.

In another class of embodiments, the polymer particles are ferrimagnetic and in particular may comprise, or be, ferrimagnetic iron oxide crystals. Accordingly, the disclosure includes polymer particles as described herein which comprise magnetic particles selected from ferrimagnetic iron oxide crystals, superparamagnetic iron oxide crystals and combinations thereof.

The magnetic particles of a polymer particle may comprise, or be, iron oxide crystals.

The total quantity of magnetic material present is generally more than 20%, preferably more than 25%, desirably more than or equal to 30%, e.g. up to 85% wt or at least 50 wt %, e.g. 30 to 80 wt %. The percentage is a weight percentage calculated on the weight of magnetic material (e.g. metal oxides) based upon the overall dry weight of the particles. Where the magnetic material consists of superparamagnetic material, therefore, the total quantity of superparamagnetic material present is generally more than 20%, preferably more than 25%, desirably more than or equal to 30%, e.g. up to 85% wt or at least 50 wt %, e.g. 30 to 80 wt %, the percentages each being a weight percentage calculated on the weight of magnetic material (e.g. metal oxides) based upon the overall dry weight of the particles.

The outer surfaces of the polymer particles may be coated. As exemplary coatings may be mentioned those formed by reacting surface-functionalized particles with an epoxide monomer or with a polyisocyanate, e.g. diisocyanate, and a diol, as described in WO 2004/053490, WO 2005/015216 or WO 2006/075185, the contents of all of which are incorporated herein by reference in their entirety. Other exemplary coatings include metal coatings, e.g. gold plating or silver, copper, zinc or tin coatings, as described in WO 00/24005 (incorporated herein by reference in its entirety).

The incorporation of magnetic particles in the particle pores and the coating of particles do not substantially change external morphology, i.e. smooth porous submicron particles remain visually smooth when viewed by SEM at a magnification of 10,000. It is a characteristic of porous polymer particles obtainable by the Ugelstad process and having magnetic material incorporated as described herein (see under the heading below "Preparation of Particles" for a description of the methods of incorporating magnetic material) that the magnetic material is distributed throughout the particle in a relatively homogenous way, as shown in FIG. 29. The Figure shows that the iron oxide particles are dispersed throughout the polymer particles without clumping and that, whilst the density of iron oxide particles appears to reduce towards the centre of the particle, there is no variation in density in a circumferential direction. In view of the absence of clumping and the wide dispersal of the particles, the distribution of the magnetic material may for practical purposes be regarded as homogeneous.

For the magnetised and coated, originally porous, particles, there are two distinct properties that generally reflect the porous nature of the polymer particle.
1) the magnetic material, e.g. iron oxide, is distributed evenly through the polymer bead (in pores) as discussed in the previous paragraph
2) magnetised and coated, originally porous, polymer particles will have a specific surface area which is slightly larger than the specific surface area of a corresponding compact polymer particle.

A corresponding compact polymer particle (same diameter and density) will have a theoretical specific surface area $A_s$:

$$A = \frac{6}{D} \cdot \frac{m}{\rho} \text{ for } m = 1\,g \qquad A_s = \frac{6}{D \cdot \rho},$$

where $D$ = particle diameter ($\mu m$)

$\rho$ = density (g/mL)

$m$ = sample weight (g)

$A$ = surface area (m$^2$)

$A_s$ = specific surface area (m$^2$/g).

The density of the coated polymer particle can be determined by a helium pycnometer.

Typical values for the specific surface area of coated and functionalised magnetic particles made using the Ugelstad method are:
1 µm particles: 6-30 m$^2$/g
0.5 µm particles of the invention: 10-70 m$^2$/g.
The invention therefore includes in some implementations magnetic particles having a diameter of less than 1 µm and a specific surface area of greater than 30 m$^2$/g, for example greater than 35 or 40 m$^2$/g. The specific surface area may for example be from greater than 30 m$^2$/g (e.g. greater than 40 m$^2$/g) to 100 m$^2$/g, for example to 90 m$^2$/g; in some embodiments the specific surface area does not exceed 80 m$^2$/g and in particular embodiments it does not exceed 70 m$^2$/g.

Additionally or alternatively to coating, the surfaces of the polymer particles may be provided with a functional group or a combination of functional groups, for example selected from a carboxylic acid, amine, tosyl, epoxy or hydroxy group. Such functionalisation enables further reaction of the particles, e.g. enables conjugation of substances to the particles.

If desired, therefore, the surfaces of the coated magnetic polymer particles may be further conjugated with a desired substance, e.g. by coupling a drug molecule, a reporter label (e. g. a chromophore, fluorophore, enzyme or radiolabel), or a ligand (e. g. an antibody or antibody fragment, a metal ion complexing agent, a member of a specific binding partner pair (e. g. biotin or streptavidin), an oligopeptide, an oligonucleotide, or an oligosaccharide.

Such coupling may be direct or indirect (and so may or may not involve the use of a coupling agent to form a linkage between the particle and the substance being coupled to it) and may be biodegradable or non-biodegradable. Biodegradable couplings may be desired if the polymer particles are to be used for the targeted release of an active compound. Where such derivatisation is desired, functional groups must be provided on the particles for the attachment of conjugated substances; for example, where the particle is coated, pendent groups of the coating may be manipulated to provide appropriate functionality (for example carboxy, epoxy, hydroxy, amino, tosyl etc. functionalities).

The functionalised coated magnetic particle may be bound to an affinity ligand the nature of which will be selected based on its affinity for a particular analyte whose presence or absence in a sample is to be ascertained. The affinity molecule may therefore comprise any molecule capable of being linked to a magnetic probe which is also capable of specific recognition of a particular analyte. Affinity ligands therefore include monoclonal antibodies, polyclonal antibodies, antibody fragments, nucleic acids, oligonucleotides, proteins, oligopeptides, polysaccharides, sugars, peptides, peptide encoding nucleic acid molecules, antigens, drugs and other ligands. Examples of suitable affinity ligands are available in the published literature and are well known. The use of further binding partners, secondary affinity ligands and linking groups which is routine in the art will not be discussed further herein although it will be appreciated that the use of such species with the particles of the invention is possible if desired.

It will be appreciated from the aforegoing that the particles of the disclosure, which may be in a population of at least 100, e.g. of at least 1,000, include particles characterised by a z-average diameter of less than 1 µm and monodispersity, which is conveniently defined as a coefficient of variation (CV) %, when measured by CPS disk centrifugation analysis, of less than 15% and optionally of less than 12%, e.g. of less than 10% as in the case of less than 5%. The particles may be characterized in terms of one of more additional properties described herein which, individually or in various combinations, distinguish the particles from those in the prior art:
(i) a z-average diameter falling within a sub-class mentioned previously, e.g. (a) of no more than: 900 nm, 700 nm, 600 nm or 500 nm and/or (b) of at least 200 nm and/or (c) of from 400-800 nm, 450-700 nm, 450-650 nm, 450-550 nm, 200-450 nm, or 300-450 nm;
(ii) a substantially smooth outer surface when viewed by SEM at a magnification of 10,000, e.g. a surface morphology substantially as it appears in FIGS. 4-6, 10C and 10D;
(iii) a characteristic, e.g. swellability, indicating a degree of cross-linking corresponding to that of a particle having a comparable matrix polymer and made by the Ugelstad process wherein the level of cross-linking greater than 25% (e.g. at least 30% such as, for example, 30-60% or 40-50%) expressed as the percentage by weight of cross-linker monomer included in the total monomer (monomer and cross-linker monomer) used in the suspension polymerisation part of the Ugelstad process, in particular where the monomers used in the suspension polymerisation are styrene and, as cross-linker, divinylbenzene;

(iv) the polymer of which the body of the particle is made, i.e. the matrix polymer, is selected from polymers and copolymers of monomers selected from acrylic monomers (e.g. methacrylate) and styrenic monomers (e.g. styrene);

(v) the particle is porous, compact or magnetic (a magnetic particle is a former porous particle now containing magnetic material in its pores and usually coated).

In the following embodiments, the particles comprise the following features:

| Embodiment | Features |
| --- | --- |
| A | (i) |
| B | (ii) |
| C | (iii) |
| D | (iv) |
| E | (i), (ii) |
| F | (iii), (ii) |
| G | (iv), (ii) |
| H | (i), (iii) |
| I | (i), (iv) |
| J | (iii), (iv) |
| K | (i), (ii), (iii) |
| L | (i), (ii), (iv) |
| M | (i), (iii), (iv) |
| N | (ii), (iii), (iv) |
| O | (i), (ii), (iii), (iv) |

Porous particles may have one or more of the following characteristics:

(vi) a specific surface area determine by gas adsorption analysis of from 100 to 700 $m^2/g$, 300 to 600 $m^2/g$, 400 to 600 $m^2/g$, or 450 to 550 $m^2/g$;

(vii) a ratio of specific surface area, as measured by gas adsorption analysis, to theoretical specific surface area for a compact particle, of at least 10:1 (for example 10:1 to 150:1, 10:1 to 120:1, or 10:1 to 110:1), of at least 20:1 (for example 20:1 to 150:1, 20:1 to 120:1, or 20:1 to 110:1), of at least 50:1 (for example 50:1 to 150:1, 50:1 to 120:1, or 50:1 to 110:1), or of at least 80:1 (for example 80:1 to 150:1, 80:1 to 120:1, or 80:1 to 110:1).

In the following embodiments, the porous particles comprise the following features, where e.g. "A+ (vi), (vii)" designates a combination of the features of embodiment A above with features (vi) and (vii):

| Embodiment | Features |
| --- | --- |
| P | (vi) |
| Q | (vii) |
| R | (vi), (vii) |
| S | A + (vi) |
| T | A + (vii) |
| U | A + (vi), (vii) |
| V | B + (vi) |
| W | B + (vii) |
| X | B + (vi), (vii) |
| Y | C + (vi) |
| Z | C + (vii) |
| AA | C + (vi), (vii) |
| AB | D + (vi) |
| AC | D + (vii) |
| AD | D + (vi), (vii) |
| AE | E + (vi) |
| AF | E + (vii) |
| AG | E + (vi), (vii) |
| AH | F + (vi) |
| AI | F + (vii) |
| AJ | F + (vi), (vii) |
| AK | G + (vi) |
| AL | G + (vii) |
| AM | G + (vi), (vii) |
| AN | H + (vi) |
| AM | H + (vii) |
| AO | H + (vi), (vii) |
| AP | I + (vi) |
| AQ | I + (vii) |
| AR | I + (vi), (vii) |
| AS | J + (vi) |
| AT | J + (vii) |
| AU | J + (vi), (vii) |
| AV | K + (vi) |
| AW | K + (vii) |
| AX | K + (vi), (vii) |
| AY | L + (vi) |
| AZ | L + (vii) |
| BA | L + (vi), (vii) |
| BB | M + (vi) |
| BC | M + (vii) |
| BD | M + (vi), (vii) |
| BE | N + (vi) |
| BF | N + (vii) |
| BG | N + (vi), (vii) |
| BH | O + (vi) |
| BI | O + (vii) |
| BJ | O + (vi), (vii) |

Magnetic particles may have one or more of the following characteristics:

(viii) a specific surface area determine by gas adsorption analysis of greater than 30 $m^2/g$, for example greater than 35 $m^2/g$ or 40 $m^2/g$ (e.g. from more than 30 $m^2/g$ to 100 $m^2/g$, from 40 $m^2/g$ to 100 $m^2/g$, from more than 30 $m^2/g$ to 90 $m^2/g$, from 40 $m^2/g$ to 90 $m^2/g$, from more than 30 $m^2/g$ to 80 $m^2/g$, from 40 $m^2/g$ to 80 $m^2/g$, from more than 30 $m^2/g$ to 70 $m^2/g$, from 40 $m^2/g$ to 70 $m^2/g$);

(ix) a ratio of specific surface area, as measured by gas adsorption analysis, to theoretical specific surface area for a compact particle, of at least 2:1, (e.g. from 2:1 to 20:1, 2:1 to 18:1, 2:1 to 14:1), optionally of at least 3:1 (e.g. from 3:1 to 20:1, 3:1 to 18:1, 3:1 to 14:1) and is optionally at least 4:1 (e.g. from 4:1 to 20:1, 4:1 to 18:1, 4:1 to 14:1).

In the following embodiments, the magnetic particles comprise the following features, where e.g. "A+(vi), (vii)" designates a combination of the features of embodiment A above with features (vi) and (vii):

| Embodiment | Features |
| --- | --- |
| BK | (viii) |
| BL | (ix) |
| BM | (viii), (ix) |
| BN | A + (viii) |
| BO | A + (ix) |
| BQ | A + (viii), (ix) |
| BR | B + (viii) |

-continued

| Embodiment | Features |
| --- | --- |
| BS | B + (ix) |
| BT | B + (viii), (ix) |
| BU | C + (viii) |
| BW | C + (ix) |
| BX | C + (viii), (ix) |
| BY | D + (viii) |
| BZ | D + (ix) |
| CA | D + (viii), (ix) |
| CB | E + (viii) |
| CD | E + (ix) |
| CE | E + (viii), (ix) |
| CF | F + (viii) |
| CG | F + (ix) |
| CH | F + (viii), (ix) |
| CI | G + (viii) |
| CJ | G + (ix) |
| CK | G + (viii), (ix) |
| CL | H + (viii) |
| CM | H + (ix) |
| CN | H + (viii), (ix) |
| CO | I + (viii) |
| CP | I + (ix) |
| CQ | I + (viii), (ix) |
| CR | J + (viii) |
| CS | J + (ix) |
| CT | J + (viii), (ix) |
| CU | K + (viii) |
| CV | K + (ix) |
| CW | K + (viii), (ix) |
| CX | L + (viii) |
| CY | L + (ix) |
| CZ | L + (viii), (ix) |
| DA | M + (viii) |
| DB | M + (ix) |
| DC | M + (viii), (ix) |
| DD | N + (viii) |
| DE | N + (ix) |
| DF | N + (viii), (ix) |
| DG | O + (viii) |
| DI | O + (ix) |
| DJ | O + (viii), (ix) |

For all embodiments, any one or more compatible features mentioned earlier in this specification may be included, for example attachment of functional groups, silica coating, absence of methylene bridged benzene rings etc.

Seed Particles

The polymer particles may be prepared by the Ugelstad process, starting with specific seed particles. The polymer seed particles are monodisperse and have an average diameter of from 20 nm to 200 nm, and the polymer, e.g. polystyrene, has a mean weight average molecular weight of greater than 1,000 but less than 70,000, when measured by gel permeation chromatography. Additionally or alternatively to the specified molecular weight range, the polymer may comprise about 10 to 700 monomer units. In embodiments, the average diameter of the seed particles is from 50 nm to less than 200 nm, e.g. 50 nm to 190 nm.

The mean weight average molecular weight of the seed particle polymer may be less than 40,000, optionally less than 30,000, further optionally less than 20,000, e.g. less than 15,000. The mean weight average molecular weight may be more than 2,000, optionally more than 4,000, further optionally more than 6,000, as in the case of more than 8,000, e.g. more than 10,000. For example, the mean weight average molecular weight may be from 6,000 to 70,000, e.g. from 6,000 to 40,000, for example from 8,000 to 70,000 or from 8,000 to 40,000.

In particular embodiments, the mean weight average molecular weight of the seed particles is from 8,000 to 20,000.

The polymer may comprise fewer than 400 monomer units, optionally fewer than 300 monomer units, further optionally fewer than 200 monomer units, e.g. fewer than 150 monomer units. The polymer may comprise more than 20 monomer units, optionally more than 40 monomer units, further optionally more than 60 monomer units, as in the case of more than 80 monomer units, e.g. more than 100 monomer units.

In particular embodiments, the polymer of the seed particle has from 80 to 200 monomer units.

The CV of the seed particle diameters, when measured by CPS disc centrifugation analysis, may be less than 10%, optionally less than 5%, e.g. less than 2% in some cases.

The seed particles suitably comprise or consist of addition polymer made by polymerising one or more ethylenically unsaturated monomers. In particular, the monomers may be vinylic, for example a styrenic monomer or an acrylic monomer. Styrenic monomers may be mentioned in particular. Suitable monomers include styrene, methyl methacrylate, methacrylic acid, hydroxyethyl methacrylate, glycidyl methacrylate, butylmethacrylate and acrylic acid and other acrylic or methacrylic monomers.

The seed particles in particular may consist of polystyrene.

Preparation of Particles

The seed particles may be made by emulsion polymerisation, following in general the procedures described in Example 9 of WO 00/61647 (incorporated herein by reference in its entirety) but with modifications to control the molecular weight of the polymer of the seed particles and the diameter of the seed particles. The preparation may be carried out under substantially oxygen-free conditions as described in WO 00/61647, but alternatively is carried out in the presence of oxygen.

The seed particles may therefore be made by an emulsion polymerisation process comprising:

forming an aqueous dispersion comprising an ethylenically unsaturated monomer and a water soluble polymerisation initiator; and agitating, e.g. mixing, until the commencement of particle nucleation; characterised in that:

the aqueous dispersion comprises a surfactant and in that a chain transfer agent is added after the commencement of particle nucleation, such that the polymerisation forms monodisperse seed particles having an average diameter of from 50 nm to 200 nm and, when measured by gel permeation chromatography, the polymer has a mean weight average molecular weight of more than 1,000 and less than 70,000.

The ethylenically unsaturated monomer may be vinylic, for example a styrenic monomer or an acrylic monomer. Styrenic monomers may be mentioned in particular. Suitable monomers include styrene, methyl methacrylate, methacrylic acid, hydroxyethyl methacrylate, glycidyl methacrylate, butylmethacrylate and acrylic acid and other acrylic or methacrylic monomers.

The polymerisation initiator may be any water soluble initiator. A suitable initiator is a persulfate (also known as peroxodisulfate), e.g. potassium or ammonium persulfate.

The surfactant may be ionic or non-ionic and is in particular ionic, for example sodium dodecyl sulfate (SDS).

The chain transfer agent may be a haloalkane, for example bromotrichloromethane, or an alkyl mercaptan, e.g. butyl mercaptan, isooctyl 3-mercaptopropionate or octylmercaptan (1-octanethiol).

Other optional components may be included as desired in the reaction mixture, in particular a buffer. Borax, i.e.

sodium borate, sodium tetraborate, disodium tetraborate, and/or hydrates thereof e.g. tetraborate decahydrate, is a suitable buffer, or another buffer may be used.

Where it is desired to reduce or substantially prevent exposure to oxygen, the polymerisation reaction may be carried out under an oxygen-free atmosphere (e.g. a noble gas). The oxygen content of the aqueous phase may be reduced by boiling the water before use or water and/or other liquid reagents may be purged with nitrogen before use. The oxygen content of the liquid reagents may also be reduced by purging with an oxygen-free atmosphere comprising another inert gas, e.g. argon. One or both of these two measures (use of an oxygen free atmosphere and de-oxygenation of water and optionally other liquids) may be performed.

In embodiments, the preparation comprises combining: a monomer, for example styrene; a buffer, for example borax; a surfactant, particularly SDS; a water soluble polymerisation initiator, for example a persulfate; and water, to form an emulsion, and agitating, e.g. mixing, until particle nucleation commences. After particle nucleation has started, a chain transfer agent is added, for example bromotrichloromethane or an alkyl mercaptan.

Where desired, any one or more of the reagent classes (monomer, buffer, surfactant, polymerisation initiator, chain transfer agent) may comprise a combination of compounds.

In embodiments, the surfactant is below its critical micelle concentration (CMC), for example below its CMC in aqueous solution. The CMC of a surfactant is a function of temperature. For example when SDS is used as the surfactant, its CMC at 25° C. is 2.3 g/L of water. Thus in embodiments the concentration of SDS is less than 2.3 g/L of water, optionally less than 2 g/L of water.

The disclosure includes methods in which the surfactant is present in a concentration of not more than 2.5 g/L, optionally not more than 2 g/L, further optionally not more than 1.7 g/L, still further optionally not more than 1.5 g/L. Also included are methods in which the surfactant is present in a concentration of at least 0.5 g/L, optionally at least 0.8 g/L, further optionally at least 1 g/L, still further optionally at least 1.2 g/L, even further optionally at least 1.5 g/L. For example, the surfactant may be present in an amount of from 0.5 g/L, optionally at least 0.8 g/L, to 2.5 g/L. In some methods, the surfactant is present in an amount of from 0.8 g/L, optionally at least 1 g/L, to 2.3 g/L, for example as in the case where the surfactant is present in an amount of from 0.8 g/L, optionally at least 1 g/L, to 2 g/L, e.g. wherein the concentration does not exceed 1.7 g/L.

The amount of the surfactant controls the particle size and is selected to give the desired average diameter. In this regard, it has been found that particle size decreases as the concentration of surfactant is increased. For example, where styrene is selected as the monomer and SDS as the surfactant, an increase in the SDS concentration from 1 g/L to 2 g/L was found in one experiment to reduce average particle size from about 180 nm to about 55 nm. The concentration of a surfactant that will provide particles with the desired average particle diameter can be determined empirically.

The addition of a chain transfer agent reduces the molecular weight of the polymer of the seed particles by reacting with the free radical of a growing polymer chain to terminate the chain and transfer the lone electron to a radical species derived from the chain transfer agent. The total amount of chain transfer agent added can be in the range 1 mol per 10 mol of monomer to 1 mol per 300 mol of monomer, for example 1 mol per 20 mol of monomer to 1 mol per 100 mol monomer, e.g. approximately 1 mol chain transfer agent per 30 mol of monomer. The time of addition of the chain transfer agent is important to obtain monodisperse seed particles: the chain transfer agent should be added shortly after the particle nucleation step and may be added over an extended time period or all the agent may be added at substantially the same time. The particle nucleation step can be detected by the presence of visible particle nucleation, e.g. by the solution becoming cloudy. If the chain transfer agent is added before particle nucleation, polydisperse seed particles may be formed. If all the chain transfer agent is added at the same time (e.g. at a single timepoint), a two peak molecular weight distribution plot is obtained (see FIG. 8). A suitable time to start adding the chain transfer agent is about 5 to 15 minutes after particle nucleation, e.g. about 10 minutes after particle nucleation. If the chain transfer agent is added over an extended time period, it is typically added for 20 minutes to 4 hours, for example for 30 minutes to 1.5 hours, e.g. for about 40 minutes. The rate of addition may be constant or variable. Where the chain transfer agent is added over a suitably extended period, a single peak may be obtained in the molecular weight distribution plot.

Figure 2A:
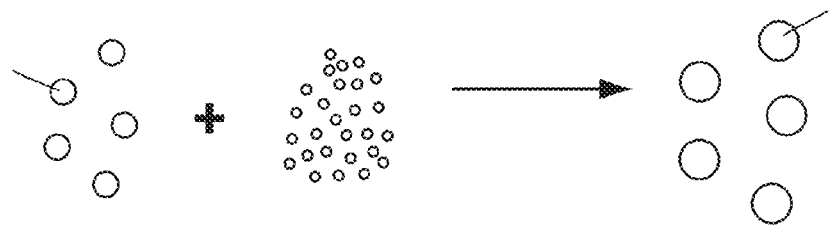
FIG. 2A, FIG. 2B, and FIG. 2C provide an overview of an Ugelstad process.
Figure 2B:
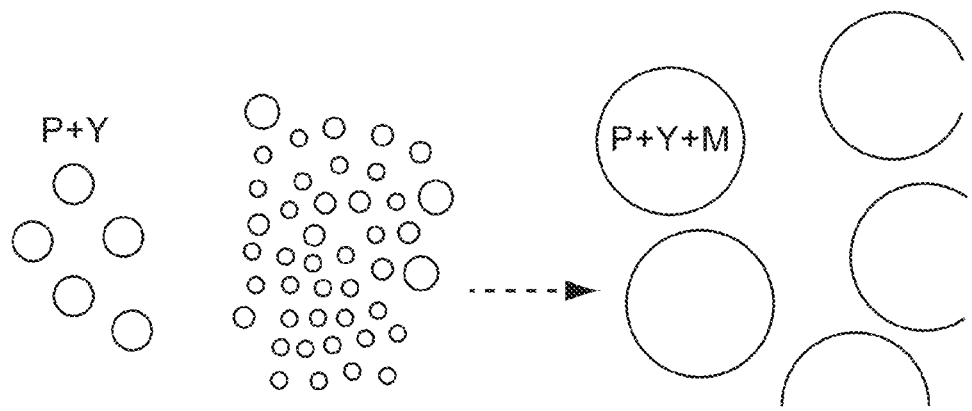
Figure 2C:
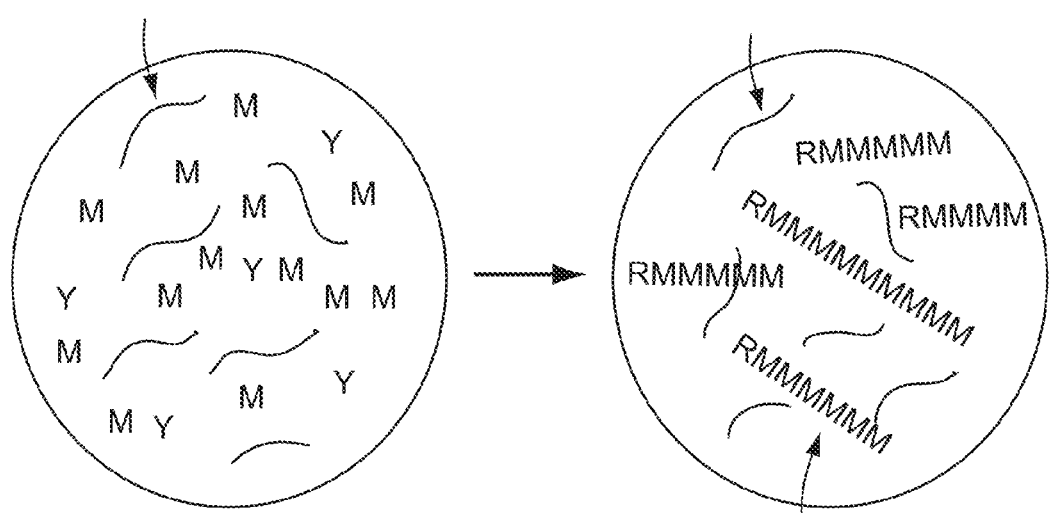

The monodisperse seed particles can then be directly subjected to an Ugelstad process, for example as outlined in FIGS. 2A, 2B and 2C. FIG. 2 is conveniently divided into 3 steps, activation of the seed particles (step A), swelling of the activated seed particles (step B) and polymerisation of the monomer in the swollen seed particles (step C). Step A involves contacting an aqueous dispersion of monodisperse polymeric seed particles (1) with an emulsion comprising finely divided droplets of an organic compound with low water solubility (2), e.g. water solubility at 25° C. of less than $10^{-2}$ g/L and/or water solubility of less than $\frac{1}{1000}^{th}$ that of a monomer (6) used in a subsequent step of the procedure. The mixture comprising the aqueous dispersion and emulsion can also comprise an organic solvent, which it is believed assists in transporting the organic compound into the seed particles. The organic compound diffuses into the seed particles over a period of time (for instance 12 to 36 hours, e.g., 24 hours, during which the mixture can be agitated, e.g. by stirring), forming activated seed particles (3). Where present the organic solvent is then removed, e.g. by dilution. The activated seed particles (3) in aqueous dispersion are in step B mixed with an aqueous vehicle containing a monomer (4), e.g. are mixed with an emulsion comprising droplets of a monomer (4). It will be appreciated that the mixing of step B can provide removal by dilution of the organic solvent in the Ugelstad method, for example the activated seed particles are typical contacted with an excess of emulsion to dilute the organic solvent, e.g. the weight of the emulsion may be at least about 5 times greater than that of the suspension containing the seed particles, e.g. about 10 times greater (for example 9 times greater). The monomer diffuses into the activated seed particles, providing swollen particles (5). The swollen particles (5) comprise a mixture of at least the monomer (6), the organic compound (7) and polymer from the seed particle (8). The swollen particle may also include other components, for instance one or more porogens or cross linkers, which can enter the particles if included in the mixture during step B. In step C polymerisation of the monomer is initiated, creating polymer (9) from the monomer inside the swollen particles (6).

Accordingly, the invention includes a method of making submicron monodisperse particles having a substantially smooth outer surface and an average diameter of less than 1 μm, the method comprising performing the Ugelstad process using seed particles having an average diameter of from 50 nm to 200 nm and made of polymer having a mean weight average molecular weight of more than 1,000 and less than 70,000, when measured by gel permeation chromatography.

Suitably, the Ugelstad process comprises:
(i) forming an aqueous dispersion comprising
the monodisperse seed particles,
finely divided droplets comprising an organic compound of molecular weight below 5,000 and water solubility at 25° C. of less than $10^{-2}$ g/L, and
an organic solvent in which the organic compound is soluble, the organic solvent being optional when the polymer forming the seed particles has an average molecular weight which corresponds to up to 50 monomer units;
(ii) allowing the organic compound to diffuse into the monodisperse seed particles, causing the seed particles to become activated;
(iii) removing the organic solvent, where present, from inside the seed particles, and contacting the activated seed particles with an aqueous vehicle containing (a) a monomer having a solubility in water at least 10 times that of the organic compound and (b) a cross-linker;
(iv) allowing the monomer and the cross-linker to diffuse into the activated seed particles to form an aqueous dispersion of swollen seed particles; and
(v) initiating polymerisation of the monomer and the cross-linker in the swollen seed particles.

The monomer used in step (iii) is usually much more soluble in water than is the organic compound. For example, it may be at least ten times more soluble in terms of weight per unit volume of water.

The cross-linker used in step (iii) is usually much more soluble in water than is the organic compound. For example, it may be at least ten times more soluble in terms of weight per unit volume of water.

As mentioned, removal of the organic solvent normally involves dilution of the organic solvent by the aqueous vehicle and step (iii) may be restated as "contacting the activated seed particles with an aqueous vehicle containing (a) a monomer having a solubility in water at least 10 times that of the organic compound and (b) a cross-linker".

It is possible to perform the Ugelstad process with more than one swelling and polymerisation stage. In these embodiments, the Ugelstad process comprises a first and a final pass, optionally at least one intermediate pass between the first and final pass, of the following steps (i) to (vi):
(i) forming an aqueous dispersion comprising
the monodisperse seed particles (first pass) or intermediate particles (final pass and optional intermediate pass),
finely divided droplets comprising an organic compound of molecular weight below 5,000 and water solubility at 25° C. of less than $10^{-2}$ g/L, and
an organic solvent in which the organic compound is soluble, the organic solvent being optional when the polymer forming the seed particles has an average molecular weight which corresponds to up to 50 monomer units;
(ii) allowing the organic compound to diffuse into the monodisperse seed particles, causing the seed particles to become activated;
(iii) removing the organic solvent, where present, from inside the seed particles, and contacting the activated seed particles or intermediate particles with an aqueous vehicle containing a monomer having a solubility in water at least 10 times that of the organic compound and, in the final pass only, a cross-linker;
(iv) allowing the monomer and, in the final pass only, the cross-linker to diffuse into the activated seed particles or intermediate particles to form an aqueous dispersion of swollen seed particles or intermediate particles; and
(vi) initiating polymerisation of the monomer and, in the final pass only, the cross-linker in the swollen seed particles.

Steps (i) to (v) are performed once for each pass, with the particles formed at step (v) representing intermediate particles suitable for use in step (i) of the subsequent pass, for all but the final pass. Ugelstad processes with more than one swelling and polymerisation stage typically involve two or three swelling and polymerisation stages, i.e. two or three passes of the above procedures.

Advantageously, the organic compound is a polymerisation initiator and desirably a heat-activated polymerisation initiator. Optionally the heat-activated polymerisation initiator is an organic peroxide, for example dioctanoylperoxide.

Where porous particles are desired, a porogen should be incorporated in the swollen seed particles, preferably in at least the final swelling and polymerisation stage ((iii)-(v)). As porogens can be used organic substances which are not polymerised in the polymerisation stage and which can be removed from the particles after polymerisation thereby producing porous particles. Porogens can also be used as blowing agents-particles impregnated with such materials, on heating may expand as the porogen vaporizes. Examples of suitable porogens include organic acids, alcohols, esters, aromatic solvents, optionally substituted aliphatic hydrocarbons having up to 12 carbons, e. g. toluene, cyclohexanol, butyl acetate, propane, pentane, cyclopentane, cyclobutane, heptane, methyl chloride, ethyl chloride, dichlorodifluoromethane, etc. As a particular example of a porogen may be mentioned toluene. A porogen may comprise a combination of compounds.

Step (iii) may therefore include contacting the seed particles with a porogen. In particular, the seed particles may be combined with an emulsion comprising water, monomer, cross-linker, and a porogen. The emulsion typical contains also a surfactant, for example SDS or another ionic surfactant. The resulting reaction mixture is maintained at a moderate temperature (e.g. no more than 30° C., typically at for example 30° C.), for example for a period of from 1 to 30 hours (typically from 10 to 24 hours), and polymerisation is then initiated. Where the organic compound used to swell the seed particles is a heat-activated polymerisation initiator, polymerisation may be initiated by raising the temperature of the reaction mixture to at least the activation temperature of the initiator; for example, when dioctanoylperoxide is selected as the organic compound, polymerisation may be initiated by raising the temperature above 30° C., typically to 60 to 70° C.

In embodiments, the Ugelstad process therefore comprises:
forming an aqueous dispersion comprising the seed particles and an emulsion comprising a water insoluble heat-activated polymerisation initiator and a water-miscible organic solvent in which the initiator is soluble and allowing the initiator to diffuse into the seed particles;
contacting the particles with an aqueous medium comprising a monomer and a cross-linker and allowing the monomer and the cross-linker to diffuse into the polymer particles to form swollen particles; and
heating the particles to activate the polymerisation initiator and polymerise the monomer and the cross-linker within the swollen particle, optionally wherein the monomer comprises an acrylic monomer, a styrene monomer or a methacrylate monomer.

A porogen is included in the aqueous medium when porous particles are to be made.

The monomer is ethylenically unsaturated and may be vinylic, for example a styrenic monomer or an acrylic monomer. Styrenic monomers may be mentioned in particular. Suitable monomers include styrene, methyl methacrylate, methacrylic acid, hydroxyethyl methacrylate, butylmethacrylate and acrylic acid and other acrylic, e.g. methacrylic, monomers. The monomer may comprise a mixture of monomer compounds, i.e. comonomers may be used. Further compounds to be mentioned as monomers or comonomers are ethyl vinyl benzene, vinyl pyridine, aminostyrene, methylstyrene, 2-hydroxyethylmethacrylate, methyl methacrylate, glycidyl methacrylate, vinyl benzyl chloride, vinylchloride, dimethylstyrene, ethylstyrene, ethyl-methyl-styrene, p-chlorostyrene, 2,4-dichlorostyrene, methyl acrylate, ethyl acrylate, butylacrylate, methacrylic acid, ethyl methylmethacrylate, maleic acid, maleic anhydride, dimethyl maleate, diethyl maleate, dibutyl maleate, fumaric acid, dimethyl fumarate, diethyl fumarate and acrylonitrile The cross-linker may be a divinylic monomer, for example divinylbenzene (DVB) or a di or multifunctional acrylate or methacrylate, for example ethylene dimethacrylate, (EDMA). Commercially available DVB is typically in admixture with a significant proportion of ethylvinylbenzene (EVB) and in practice a styrene/DVB mixture will therefore typically contain also EVB.

Functional groups may be introduced by the use of a functionalised monomer or comonomer, e.g. glycidyl methacrylate, HEMA (2-hydroxyethyl methacrylate), nitrostyrene or aminostyrene. As an alternative to the polymer particles being formed carrying surface functionalisation, or additionally thereto, functionalisation of the polymeric material may take place after polymerisation by, for example, nitration and subsequent reduction of the thus-formed nitro groups to pendant amine groups, or direct amination, for example by treatment with aminoethanol. After preparation of functionalised polymer particles, functional groups may be subjected to one or more functional group transformations, for example nitro groups may be reduced to amino groups. Functional groups, whether introduced in the synthesis of the particles, added after synthesis of the particles, or created by transformation of either such group, may undergo further reactions, for example to conjugate the particles to another substance.

The present invention thus relates also to conjugates comprising a particle of the invention coupled to another substance, for example a ligand, by a residue of a reaction between two functional groups. Suitable ligands include a biological molecule, such as an antibody, an antibody fragment, a protein, a polypeptide, an enzyme, a polynucleotide, biotin, a probe, a primer, or a nucleic acid fragment; or chemical molecules, such as chemical polymers, medicinal substances, cage molecules, chelating agents, or catalysts. The present invention also relates to the uses of these conjugates, for example use in biological assays.

One class of particles of the invention is non-magnetic. Another class of particles is magnetic, e.g. superparamagnetic. Suitable processes for preparing magnetic polymer particles are described in U.S. Pat. No. 4,654,267 (Ugelstad) the contents of which are incorporated herein by reference. U.S. Pat. No. 4,654,267 proposed a preparative method whereby, in its simplest form, porous polymer particles are impregnated with solutions of iron compounds whereafter the iron is precipitated, for instance by raising the pH value. The precipitated iron compounds may then be converted to superparamagnetic iron oxide crystals by heating. In the process, solutions of iron salts and optionally salts of other metals which may form magnetic ferrites, in water or in a mixture of water and water-soluble organic solvents or in organic solvents, are mixed with polymer particles in dry form or dispersed in water or in a mixture of water and water-soluble organic liquids or in organic liquids, and the metals are precipitated in the form of hydroxides, for instance by raising the pH value, and, if desired, the particles are heated.

To produce porous magnetic polymer particles having magnetic material disposed within the polymer pores, U.S. Pat. No. 4,654,267 advocated the use of porous polymer particles having surface functional groups which serve to draw the iron ions into the polymer particles. U.S. Pat. No. 4,654,267 describes that examples of monomers which had been found to be particularly suitable were dimethylaminoethylmethacrylate, N-(dimethylaminopropyl)-methacrylic amide and vinyl pyridine, which compounds provide functional groups which will bind the iron salts with coordinate bonding. Other examples of suitable monomers described in the US patent are those which contain ethylene oxide groups or alkylene imine groups ($-CH_2-CHR-NH-$, in which R=H or alkyl).

U.S. Pat. No. 4,654,267 describes that it is also possible to bind the iron by means of ionic bonds. By having acid groups on and inside the particles, the iron may be transported from the outer phase of the dissolved iron salt to be bound to these groups. Examples of monomers which will provide such acid groups are methacrylic acid, p-vinyl benzoic acid and maleic anhydride. It will also be appreciated that acid groups can be created on polymers made from monomers that lack native acid groups, e.g. polystyrene, for example by reacting the polymer particles with a mixture of sulphuric and nitric acid, to generate nitrated polymer particles. The iron salt-binding groups may also be attached to the premade polymers. Thus, it is possible to prepare a copolymer from a monomer mixture which essentially consists of vinyl monomer with epoxy group(s) such as glycidyl methacrylate. By treating the final polymer with substances such as, for example, ethylenediamine which react with epoxy groups and which contain N-groups, said groups will become covalently bonded on and inside the particles.

Where the porous polymer particles comprise nitrated polymer particles, e.g. nitrated polystyrene, magnetic polymer particles can be prepared by the following procedure. A solution comprising the nitrated polymer particles and iron (II), e.g. $FeSO_4$, is made. After the polymer particles are impregnated with the iron compound, the pH is increased, e.g. by addition of ammonia. This causes partial oxidation of iron (II) to iron (III), partial reduction of nitro groups of the polymer particles to amine groups and precipitation of the iron ions as superparamagnetic ferrites, e.g. maghemite and/or magnetite, in the pores of the polymer particles. The amine groups provide surface functional groups that can react with monomers used to form a coating polymer.

The leaching of magnetic crystals (e.g. superparamagnetic crystals) from the porous polymer particles may be further inhibited by forming a coating over the magnetic crystal-loaded polymer particles. For example, a coating comprising at least one transition metal oxide, e.g. a titanium oxide or a zirconium oxide, can be formed over the superparamagnetic crystal-loaded polymer particles, as described in WO 2008/079905 (incorporated herein by reference in its entirety). Another exemplary coating is a polymer coating, as described below.

The leaching of superparamagnetic crystals from the porous polymer particles may be further inhibited by forming a coating over the superparamagnetic crystal-loaded polymer particles, or more particularly by at least partly filling the pores of the particles with a polymer coating, as described in WO 2004/053490 or WO 2006/075185 (incorporated herein by reference in their entirety). The resultant particles comprise a matrix polymer, magnetic crystals (e.g. superparamagnetic crystals) and a polymer coating.

Such coating polymers may typically be formed from monomers reactive with functional groups pendant from the surface of the polymer of the underlying particles.

The coating polymer may be formed from at least one epoxide compound, e.g. at least two epoxide compounds. The reaction of the porous magnetic polymer particle with the coating monomers generates a coating polymer within the pores of the matrix polymer particles which serves essentially to block these pores, physically encapsulating the superparamagnetic crystals within the polymer particles. The resulting "coated" particles then have reduced porosity relative to the porous starting material. It is believed that the superparamagnetic crystals appear to catalyse the polymerisation so that the coating forms preferentially in their vicinity. Since the majority of the superparamagnetic crystals are within pores in the starting porous particles, the coating may not form to any significant extent on the external surface of the particles.

In one embodiment, the porous polymer particles are reacted with a mixture of epoxides.

The coating polymer may be formed from one or more epoxides. At least one epoxide may contain at least one ether link and optionally a hydrophobic component, e. g. an alkylene chain. Generally the at least one epoxide will have a carbon atom content of from 3 to 50, preferably 3 to 25. Typical epoxides that may be used include epichlorohydrin, epibromohydrin, isopropylglycidyl ether, butyl glycidyl ether, allylglycidyl ether, 1,4-butanediol diglycidyl ether (1,4-bis(2,3-epoxypropoxy) butane), neopentylglycol diglycidyl ether, ethylene glycol diglycidyl ether, glycerol diglycidyl ether, glycidol, and glycidyl methacrylate, ethyl hexyl glycidylether, methyl glycidylether, glycerol propoxylate triglycidylether, poly(propylene glycol) diclycidylether, 1,3 butanediol diglycidylether, tert-butyl glycidylether, 1,4 cyclohexanedimethanol diglycidyl ether, diethylene glycol diglycidyl ether, dodecyl glycidylether, O-(2,3 epoxypropyl)-O'-methylpolyethylene glycol glycidylether, glycidyl tetrafluoroethyl ether, 1,6 hexanediol diglycidylether, octyl glycidylether, decyl glycidylether, poly(epichlorohydrin-co-ethylene oxide-co-allyl glycidylether), polyethylene glycol diglycidyl ether, trimethylolethane triglycidylether, trimethylolpropane, triglycidylether, tert-butyldimethylsilyl glycidylether, 1,2-epoxybutane, 1,2-epoxypentane, 1,2-epoxy-5-hexene, 1,2-epoxy-hexane, 1,2-epoxy-7-octene, 1,2-epoxyoctane, 1,2,7,8-diepoxyoctane, 1,2-epoxy-9-decene, 1,2-epoxydecane, 1,2-epoxydodecane, 1,2-epoxytetradecane etc. In embodiments, the coating polymer is formed from two or more epoxides which all contain at least one ether link and optionally a hydrophobic component.

Typically, the coating reaction may be effected by impregnating the porous magnetic polymer particle with the coating monomers e. g. using a solution of these (for example in an organic solvent such as methanol, toluene, xylene, diethyleneglycol, dimethyl ether or diglyme) or by mixing a dispersion of the porous particles in an organic solvent with a liquid epoxide mixture.

If desired, autofluorescence of the polymer particles may reduced or avoided by keeping the particle essentially free of conjugated delocalized electron systems, other than those in benzene rings, as described in WO 2004/053490 (incorporated herein by reference in its entirety). Such particles will not be cross-linked with divinylbenzene, since any unreacted compound will autofluoresce.

The polymer particles may be silica coated. The skilled reader will require no explanation as to the formation of silica coatings but a short summary is presented here for the non-skilled reader. Silica coatings on polymer particles can be formed by the same processes used for the polymerisation of metal alkoxides, for example the sol-gel process. This is a process in which the precursor, typically tertraethoxide silane (TEOS) undergoes a series of hydrolysis and polycondensation steps, leading to the silica coating on the polymer particles. In the first step, the silica alkoxide precursor is partially hydrolysed. The degree of hydrolysis is determined by the amount of water and catalyst (acid, base) present. In a second step, partially hydrolysed molecules react together in a condensation reaction, liberating small molecules, typically water or alcohol. This continues and yields a silica polymer. The structure of the silica polymer will be influenced by the rate of hydrolysis and condensation, and thereby catalysis. Prior to the silica coating the polymer particles can be surface-functionalized. This provides a template capable of reacting with the silicon alkoxide or the partially hydrolyzed reaction products.

The stages of the method are illustrated below:
Hydrolysis:
Alcohol condensation:
Water condensation:

The skilled reader will be aware that alternative technologies exist for applying silica coatings, e.g. water-in-oil emulsion techniques. For more information, the reader is referred to Brinker C. J. and Scherer G., *SOL-GEL SCIENCE: The Physics and Chemistry of Sol-Gel Processing*, Academic Press, San Diego 1990; and to Ziegler J. M. and Fearon F. W., *Silicon-Based Polymer Science: A Comprehensive Resource*, American Chemical Society, Washington D.C. 1990.

The swelling and polymerisation stages are typically performed in aqueous dispersion in the presence of materials, e. g. surfactants, stabilizers, organic solvents, etc., which it is desirable to remove from the particles. Likewise, it may be desirable to remove linear polymers which formed the seed particles, for example to avoid leakage during use in chromatography. Generally a water-miscible organic solvent in which the cross-linked polymer is insoluble, or an aqueous solution of such a solvent, may be used for removal of contaminants and linear polymers. However it is particularly suitable to use butyl acetate in this regard in view of its effectiveness in removing undesired residues from the Ugelstad polymerisation process.

Depending on their desired end use, the monodisperse polymer particles may be coated (e. g. with metallic coatings); they may have materials, e. g. magnetic crystals, specific binding partners (e. g. antibodies, avidin or streptavidin, etc.), or catalysts bound to their surface or deposited in pores or on the surface; or they may be expanded (e. g. using blowing agents). The invention therefore includes monodisperse submicron polymer particles as described herein having a matrix polymer (e.g. polystyrene) which may be porous and optionally further having one or more additional substances, for example selected from magnetic material included in any pores, one or more coating materials, one or more functional groups, one of more conjugated substances (e.g. specific binding partners, nucleic acids, proteins, other biological molecules or structures). The particles may be coupled to a substrate.

The invention includes particles obtained by, or having the characteristics of particles obtained by, the preparative processes described herein.

The Ugelstad processes described herein may be worked to be highly reproducible and scaleable. The invention therefore enables consistency between and within batches, which is a prerequisite for industrial application. The invention also enables production of pilot scale batches of e.g. at least 300 g as well as kilogram scale industrial batches, which is another prerequisite for viable industrial production. In contrast, suspension polymerisation processes seem to suffer from a lack of reproducibility and scaleability which makes them non-viable for industrial use, to the extent that one batch of particles may lack good and consistent spherical particle shape. The invention therefore provides the following inventions in relation to the particles and manufacturing processes of the disclosure:

manufacturing processes which result in batches of particles wherein the weight of particles when determined as dry particles is at least 300 g, e.g. at least 500 g and optionally at least 1 kg, for example at least 5 kg as in the case of at least 10 kg a particle batch wherein the weight of particles when determined as dry particles is at least 300 g, e.g. at least 500 g and optionally at least 1 kg, for example at least 5 kg as in the case of at least 10 kg a particle batch wherein the weight of particles when determined as dry particles is at least 300 g, e.g. at least 500 g and optionally at least 1 kg, for example at least 5 kg as in the case of at least 10 kg and wherein the particles of any two or more sub-populations (e.g. of at least 100 and optionally at least 1000 particles) of the batch have substantially indistinguishable characteristics, e.g. when 2, 5, 10 or 20 sub-populations (i.e. samples) are selected, optionally wherein the indistinguishable characteristics include one or a combination of (e.g. all of) size, shape, surface morphology, swelling properties and specific surface area methods comprising the parallel or sequential performance of batch manufacturing processes to result in 2 or more batches of polymer particles, for example 5 or more batches, e.g. 10 or more batches, wherein the particles of each batch have identical characteristics with the particles of each other batch within industrial acceptable tolerance, e.g. the variation between batches of one or more of (e.g. all of) size, swelling properties and specific surface are 15% or less, e.g. 10% or less and optionally 5% or less, wherein the weight of particles of each batch when determined as dry particles may for example be at least 300 g, e.g. at least 500 g and optionally at least 1 kg, for example at least 5 kg as in the case of at least 10 kg a collection of 2 or more batches of polymer particles, for example 5 or more batches, e.g. 10 or more batches, wherein the particles of each batch have identical characteristics with the particles of each other batch within industrial acceptable tolerance, e.g. the variation between batches of one or more of (e.g. all of) size, swelling properties and specific surface are 15% or less, e.g. 10% or less and optionally 5% or less, wherein the weight of particles of each batch when determined as dry particles may for example be at least 300 g, e.g. at least 500 g and optionally at least 1 kg, for example at least 5 kg as in the case of at least 10 kg a method for the delivery of particles comprising transporting on or in a vehicle (e.g. a road vehicle, a ship or an aircraft) at least one batch (for example 5 or more batches, e.g. 10 or more batches) of particles wherein the weight of particles of each batch when determined as dry particles is at least 300 g, e.g. at least 500 g and optionally at least 1 kg, for example at least 5 kg as in the case of at least 10 kg.

In view of the consistency of the quality and characteristics which the particles of the disclosure may possess, they may be used in methods which comprise performing processes in relation to a conjugated substance, e.g. selected from labels, biological molecules and biological structures, for example biological molecules such as amino acids, saccharides, nucleotides and nucleosides and multimers made by condensing together two or more such monomers, e.g. polypeptides, proteins, polysaccharides, oligonucleotides and nucleic acids. As labels may be mentioned dyes, e.g. fluorescent dyes, quenchers, enzymes, and semiconductor nanocrystals. The invention includes such uses as well as:

i) conjugates comprising a population of particles of the disclosure at least a portion of which are coupled to a conjugated substance, e.g. one as just described ii) a method comprising coupling at least a portion of a population of particles of the disclosure to a substance, e.g. one as just described iii) a method comprising coupling at least a portion of a population of particles of the disclosure to a substrate.

The Ugelstad processes described herein can be performed consistently without the problems which in practice can arise with emulsion polymerisation, e.g. agglomeration of particles as well as variation in the product.

Uses of the Particles

The particles, whether magnetic or non-magnetic, can be used in many applications, e.g. information storage, color imaging, bioprocessing, diagnostic microbiology, biosensors and drug delivery. Magnetic particles may be used in magnetic refrigeration, ferrofluids and magnetic switches. In particular, the magnetic particles, for example magnetic particles coupled to a ligand or magnetic particles comprising one or more specific binding partners, can be detected by magnetic detectors, for example a giant magnetoresistive sensor (GMR), Hall sensor, or superconducting quantum interference device (SQUID) sensor.

A SQUID is a very sensitive magnetometer that can be used to measure extremely small magnetic fields, based upon superconducting loops containing Josephson junctions. Magnetic particles of the invention typically have small magnetic fields, e.g. due to the small size of the particles. The high sensitivity of SQUID means that it is a particularly suitable detector for the magnetic particles of the invention.

The magnetic particles can, for example, be used as contrast agents in SQUID imaging, as described in EP0523116 (incorporated herein by reference in its entirety). The magnetic particles can also be used in an assay, e.g. an affinity based assay and/or a bioassay and/or a competitive binding assay. In this regard it will be appreciated that the magnetic particles of the invention can be used as a detection tag in the assay, linked to one of the binding partners in an assay. For example, a specific binding partner (for instance an affinity molecule), e.g. an antibody, can be attached to the surface of a magnetic particle. Where the specific binding partner is an antibody, an antigen-antibody reaction will take place between the antibody and an antigen (the target substance) to produce a weak magnetic field signal attributable to the magnetic marker, which can be measured by a magnetic detector, e.g. a SQUID, as is described in US 2006/0035388 (incorporated herein by reference in its entirety).

The particles, e.g. functionalised polymer particles, can be used to assist in creating a semi-ordered array of molecules for assaying. For example, such molecules may be bound to the particles with a first binding site where binding may be covalent; the binding is optionally cleavable by enzymatic, chemical, photonic or other appropriate methods. The molecules to be assayed can contain a second binding site designed to bind to a third binding site on a surface to which deposition will occur. In this sense, the particles can act as spacers preventing two molecules from binding to the surface at less than a user defined distance where such distance is defined by the diameter of the particle. This can be useful for individual molecules so that they may be individually detectable by minimizing crosstalk from neighbouring molecules. It can also be useful for depositing molecules, such as polynucleotides (or RNA, or proteins, or other biomolecules) that will be amplified. In embodiments using amplification, overlap of the resulting localized populations can be controlled by considering the size of the particles, the rate of amplification and the amount of time for which the reaction is run. After initial deposition, or after amplification, the particles can be cleaved granting easier access to the molecules to be assayed. Methods involving the use of silica particles to assist in creating a semi-ordered array of molecules are disclosed in J. J. Schwartz and S. R. Quake, "High density single molecule surface patterning with colloidal epitaxy", Applied Physics Letters, 91, 083902 (2007) and US 2009/0053690 (both incorporated herein by reference in their entirety) and it will be appreciated that these methods can be readily adapted to particles of the present invention, e.g. polymer particles functionalised with amino groups.

Silica-coated particles may be useful in processes for the analysis or treatment of nucleic acids the well known principle of nucleic acid binding to a silica surface. U.S. Pat. No. 5,234,809, for example, describes a method where nucleic acids are bound to a solid phase in the form of silica particles, in the presence of a chaotropic agent such as a guanidinium salt, and thereby separated from the remainder of the sample. Processes using magnetic particles are increasingly being used as high-throughput techniques for the automated isolation of nucleic acids, in which total nucleic acid (both DNA and RNA) is isolated from a biological sample by reversible binding to SiOH-modified magnetic particles. For this purpose the nucleic acids to be isolated are contacted with silica-modified magnetic particles in a chaotropic binding buffer. In a typical process using silica-coated particles, the binding of the nucleic acids to the particle surface takes place over a range of temperatures, from ~18° to ~38° C. for example, over a period of time up to an hour while the particle suspension is mixed by shaking or vortexing. The particles loaded with nucleic acids are then drawn towards the vessel wall by applying a magnetic field, and the supernatant is aspirated and discarded. After removing the magnetic field, the particles are resuspended and washed several times with a washing buffer or buffers. The nucleic acids bound to the magnetic particles are then removed from the particles at a high temperature, such as for example at 90° C. for 10 mins, with the aid of an elution buffer. After re-applying the magnetic field, the eluate containing the nucleic acids can be pipetted off.

The SOLiD™ sequencing system (Sequencing by Oligonucleotide Ligation and Detection) of Applied Biosystems uses stepwise cycled ligation for high throughput DNA sequencing. In this bead based system, beads (i.e. polymer particles) loaded with DNA templates undergo sequential ligation and cleavage reactions using 4-colour, fluorescently-labeled octameric probes. These probes are delivered serially and serve to interrogate dinucleotide positions on DNA strands. It would be desirable to support higher bead densities that facilitate an increased number of bead events per instrument run and improved probe chemistry, affording increased sequencing fidelity.

Sequencing by Oligonucleotide Ligation and Detection involves attachment of a nucleic acid target to a cross-linked polymer particles (beads) followed by immobilization of a plurality of the particles onto a surface. Each nucleic acid-bead conjugate comprises a unique DNA sequence, Sequencing techniques of this type are disclosed in International Publication No. WO 2006/084132 A2 (included herein by reference).

Methods of attachment of the beads to the support have utilized a flat glass microscope slide irreversibly coated with streptavidin. Nucleic acid-laden beads are contacted with biotinylated nucleotides (e.g., obtained by the action of biotinylated dNTP's and terminal deoxytransferase on the DNA target subsequent to attachment to the bead). Incubation of the biotinylated beads with the streptavidin coated slide results in immobilization of the beads onto the slide by the interaction of streptavidin with the biotin. While kinetically this is a very effective attachment scheme, movement of the beads on the slide was sometimes observed under the conditions required by the DNA sequence assay. When beads are present in high densities on the slide (e.g., up to 100,000 beads/mm$^2$) and interrogated multiple times (e.g., up to 25 times), any significant bead movement can preclude robust identification of a particular bead on subsequent scans within a dense population of beads.

US 2009/0099027 (equivalent to WO2009026546, both included herein by reference) therefore describes a covalent system for bead immobilization that reduces movement of the beads during sequencing and other forms of genetic analysis. The method comprises: reacting a nucleophilic group on the surface of a substrate with a molecule comprising a plurality of electrophilic groups thereby providing one or more free electrophilic groups on the surface of the substrate; and reacting nucleophilic groups on a surface of a particulate material with the one or more free electrophilic groups on the surface of the substrate to covalently attach the particulate material to the substrate.

US 2009/0099027 describes the modification of a nucleophilic (more particularly, amino functional) surface with a multifunctional electrophilic reagent. For example, the electrophilic surfaces of silicate glass microscope slides can be readily converted to a nucleophilic surface by reacting surface groups with (aminopropyl) trialkoxysilanes.

A DNA target nucleic acid that had been covalently attached to a cross-linked polymer bead may be modified by the action of aminoalkyl dNTP's and terminal deoxytransferase on the DNA target subsequent to attachment to the bead. The nucleophilic amino group on the DNA target can then react with the residual electrophilic group of the support surface to form multiple stable covalent bonds between the bead and the glass surface.

It has been found that stable covalent bonds can be formed between a surface containing electrophilic groups and particles containing nucleophilic groups. In addition, beads containing nucleophilic amino groups from the action of amino-dNTP's and terminal deoxytransferase on a DNA target can be immobilized under aqueous basic conditions on the modified surface. For example, surfaces comprising amino groups that have been activated with benzene 1,4-diisothiocyanate can be used to immobilize beads with nucleophilic groups. In addition, the covalent attachment appears to be quite stable, and no bead movement is observed.

The surface immobilized beads can be used in methods of analysing nucleic acid sequences based on repeated cycles of duplex extension along a single stranded template via ligation. Sequencing methods of this type are disclosed in U.S. Pat. Nos. 5,750,341; 5,969,119; and 6,306,597 B1 and in International Publication No. WO 2006/084132 A2. Each of these publications is incorporated by reference herein in its entirety. Moreover, the techniques described in the aforementioned publications can be used to analyse (e.g., sequence) nucleic acid templates attached to particles that are bound to supports as described herein. The immobilized beads can be used in sequencing methods that do not necessarily employ a ligation step, such as sequencing using labeled nucleotide that have removable blocking groups that prevent polynucleotide chain extension (e.g., U.S. Pat. Nos. 6,664,079; 6,232,465; and 7,057,026, each of which is incorporated by reference herein in its entirety). The immobilized beads can be used in a variety of techniques in which signals on the beads are repeated detected through multiple cycles.

The beads which are used in SOLiD sequencing may be monodisperse submicron particles of the disclosure. The present invention therefore includes the use of the monodisperse submicron particles in the methods and products disclosed in the publications mentioned in the previous paragraph and the applicant of the present application considers all such uses, methods and products to fall within the present invention and reserves the right to claim them. The use of submicron particles in SOLiD sequencing enables a greater density of particles to be attached to the glass surfaces (e.g. glass panels or microscope slides). Further included in the present invention is a method of performing SOLiD sequencing which uses monodisperse submicron particles of the disclosure, e.g. wherein monodisperse submicron particles of the present disclosure are coupled to a nucleic acid target and immobilised on a surface, e.g. a glass surface. The method of immobilisation is not critical and may be covalent or non-covalent, examples of non-covalent coupling being through streptavidin/avidin-biotin binding. The covalent coupling may be as described in US 2009/0099027 and WO2009026546, for example, but any other suitable technique for covalent coupling may be used. Included in the invention, therefore, is a method of forming a product (an article of manufacture), comprising coupling monodisperse submicron particles of the present disclosure to a nucleic acid and optionally further comprising immobilising the resultant nucleic acid-laden particles on a surface, e.g. a glass surface. The nucleic acid may be used as a target in sequencing, e.g. using SOLiD sequencing.

For example, a method is provided that comprises:
(a) hybridizing a first initializing oligonucleotide probe to a target polynucleotide to form a probe-target duplex, wherein the oligonucleotide probe has an extendable probe terminus, wherein the target polynucleotide is attached to a polymer particle which is a member of a population of polymer particles as disclosed herein and wherein the particle is covalently attached to the surface of a solid support;
(b) ligating a first end of an extension oligonucleotide probe to the extendable probe terminus thereby forming an extended duplex containing an extended oligonucleotide probe, wherein the extension oligonucleotide probe comprises a cleavage site and a detectable label;
(c) identifying one or more nucleotides in the target polynucleotide by detecting the label attached to the just-ligated extension oligonucleotide probe;
(d) cleaving the just-ligated extension oligonucleotide probe at the cleavage site to generate the extendable probe terminus, wherein cleavage removes a portion of the just-ligated extension oligonucleotide probe that comprises the label from the probe-target duplex; and
(e) repeating steps (b), (c) and (d) until a sequence of nucleotides in the target polynucleotide is determined.

Also provided is a method of sequencing a nucleic acid comprising:
(a) hybridizing a primer to a target polynucleotide to form a primer-target duplex, wherein the target polynucleotide is attached at a 5' end to a polymer particle which is a member of a population of polymer particles as disclosed herein and wherein the polymer particle is covalently attached to the surface of a support;
(b) contacting the primer-target duplex with a polymerase and one or more different nucleotide analogues to incorporate a nucleotide analogue onto the 3' end of the primer thereby forming an extended primer strand, wherein the incorporated nucleotide analogue terminates the polymerase reaction and wherein each of the one or more nucleotide analogues comprises (i) a base selected from the group consisting of adenine, guanine, cytosine, thymine and uracil and their analogues (ii) a unique label attached to the base or analogue thereof via a cleavable linker; (iii) a deoxyribose; and (iv) a cleavable chemical group which caps an —OH group at a 3'-position of the deoxyribose;
(c) washing the surface of the support to remove any unincorporated nucleotide analogues;
(d) detecting the unique label attached to the just-incorporated nucleotide analogue to thereby identify the just-incorporated nucleotide analogue;
(e) optionally, permanently capping any unreacted —OH group on the extended primer strand;
(f) cleaving the cleavable linker between the just incorporated nucleotide analogue and the unique label;
(g) cleaving the chemical group capping the —OH group at the 3'-position of the deoxyribose of the just incorporated nucleotide analogue to uncap the —OH group;
(h) washing the surface of the support to remove cleaved compounds;
(i) repeating steps (b)-(h).

The polymer particles of the disclosure may be used in any method of nucleic acid sequencing which involves a polymer particle. The invention includes particles of the disclosure coupled to a nucleic acid as well as a method of sequencing a nucleic acid which comprises coupling a nucleic acid to a population of particles of the disclosure. The nucleic acid may be DNA or RNA.

The present disclosure includes a product (e.g. an article of manufacture) comprising a plurality of monodisperse submicron particles of the disclosure coupled to a substrate such as, for example, glass surface, for example through a streptavidin-biotin linkage, an avidin-biotin linkage or through a covalent linkage, e.g. as described in US 2009/0099027 and WO2009026546. The particles may be coupled to the substrate through a nucleic acid. The present disclosure includes the use of the monodisperse submicron particles of the disclosure to make such a product. The present invention includes the use of the attachment chemistry described in US 2009/0099027 and WO2009026546 to attach monodisperse submicron particles of the disclosure to a substrate, and the applicant reserves the right to claim methods of using such chemistry and the products thereof. The present specification therefore includes by reference the disclosures of US 2009/0099027 and WO2009026546, including without limitation [0007] to [0029], [0057] to [0094] and the claims of US 2009/0099027 and the applicant reserves the right both to claim combinations of such teachings with monodisperse submicron beads of the present disclosure (i.e. in which the particles/beads of the US specification are replaced by particles of the present disclosure) and to reproduce the contents of US 2009/0099027 and WO2009026546, including without limitation [0007] to [0029], [0057] to [0094] of US 2009/0099027, verbatim in the present specification. For the avoidance of doubt, it is hereby confirmed that the applicant reserves the right to reproduce in the present specification the figures of US 2009/0099027 referred to in said paragraphs, and incorporates said figures herein by reference.

The invention therefore includes methods in which functionalised monodisperse polymer particles of the disclosure are subjected to one or more further reactions to obtain a desired product. The invention also includes the use of these products in applications.

Analytical Methods
Molecular Weight Measurement

The molecular weight distribution of the polymers in a seed particle or other non cross-linked polymeric particle can be measured by a form of size exclusion chromatography (SEC), e.g. gel permeation chromatography (GPC), calibrated with suitable polymeric molecular weight standards. For example, determination of the molecular weight of polystyrene polymers by GPC ideally uses polystyrene molecular weight markers as set out in the following procedure. A calibration curve, e.g. an 8 point calibration curve, is prepared using polystyrene standards; (Polymer Labs) PS-1 MW range 266-8,000,000 amu can be used. The sample is dissolved in tetrahydrofuran (THF) containing 0.015% sulphur (S added as a retention time marker) to make a solution of 0.5 mg/ml, and filtered (0.45 µm Nylon Aerodisc) prior to instrumental analysis. Both the standards and the sample are suitably run on the SEC instrumentation detailed below, allowing molecular weight to be determined.

Instrumentation:

The SEC system used for GPC may consist of the following units:
Rheodyne i725 injector with 100 µl sample loop
Waters 510 HPLC pump
Waters 484 Tunable adsorbance (UV) Detector operated at 254 nm
Column Set:
Pre-column filter
2. PLgel 5 µm Mixed C Waters (in THF)
connected in series and placed in a column heating module Waters 038040
Column temperature. 40° C.
Eluent: THF (HPLC grade)
The THF has been pre-filtered (Millipore Fluoropore 0.45 µm membrane filter).

Size and Size Distribution

The size distribution of samples can be measured using disc centrifugation, e.g. CPS Disc Centrifugation™ on Disc Centrifuge Model DC20000, using protocols provided by the instrument manufacturer. Accurate results require calibration with a standard of similar density to the sample being analysed and thus is only of use where a suitable polymeric standard is available, for example a set of compact polystyrene particle standards for particles of the disclosure comprising predominantly polystyrene. Where the samples being measured have a density that is not known, e.g. for porous particles, the measurement obtained by CPS disc centrifugation will be reproducible but will not provide the actual diameter.

Photon correlation spectroscopy (PCS) can be used to obtain the hydrodynamic diameter of a particle in the form of the z-average. The measurement is independent of the particle density and based on Brownian motion of small particles. PCS measurements for nanosized particles can be obtained, for example with a Malvern ZetaSizer Nano-ZS, Model ZEN3600. Further details and methods can be found in the Malvern Zetasizer Nano series manual (incorporated herein by reference in its entirety).

Another technique that can be used to determine the diameters of individual submicron particles is measurement of the diameter of the dry polymer particles as imaged by scanning electron microscopy (SEM). Dry particle samples can be prepared for SEM imaging by capture on an SEM compatible surface and coating of the sample with carbon or gold by vapour deposition. The diameter can be determined by individual measurements of the particles appearing the SEM image. When assessing the surface morphology of submicron particles, e.g. of at least 200 nm and less than 1000 nm diameter, a suitable SEM magnification is 10,000. Measurements should be made of at least 10 particles. SEM images can, for example, be obtained with a Philips XL30 instrument, operated at an acceleration voltage of 20 kV, with a typical detection area of 0.0004 $mm^2$ and magnification of 10,000.

PCS is a preferred method of determining average diameter, suitable for use with particles of both known and unknown density.

Visual Appearance

Visual appearance of SEM images is particularly important for characterizing the surface morphology of the particles, e.g. whether the particles have a relatively smooth surface (regular spherical shape) or are rough and irregular (so-called "cauliflower particles"). Polymer particles of the invention have a smooth, spherical appearance at a magnification of 10,000. As mentioned above, measurements made from an SEM image can also be used to determine the size of individual particles and the size distributions of relatively small populations, such as for 20 to 50 particles.

Surface Area and Pore Size Distribution

Surface area can be measured by gas adsorption methods, with the surface area calculated using BET theory (see, e.g. Chapter 3, "Surface area and pore structure by gas adsorption" of P A Webb and C Orr, Analytical methods in fine particle technology, Micromeritics, 1997, incorporated herein by reference in its entirety). An example of an instrument that can be used to perform surface area measurements of submicron beads is the Tristar Surface Analyser and Porosity Analyser. This instrument can be used to measure the specific surface area and also the pore size distribution. When measuring the pore size distribution of polymer particles, the procedure measures the distribution of small pores with a pore radius of from approximately 10 Å to 350 Å. The determination of pore size distribution is based upon the BHJ method and the Harkins-Jura equation to estimate the film thickness.

Detection of Coatings

The presence of coatings on polymeric beads can be determined in a number of ways. Infrared spectroscopy (IR), for example fourier transform infrared (FTIR) spectroscopy, can be used to qualitatively detect the presence of functional groups or other coatings on the surface of polymeric beads. Coating increases the mass of the beads, so detection of a weight increase relative to uncoated beads is indicative of the presence of a coating. Coated beads also typically have a reduced surface area compared to uncoated beads, so comparative surface area measurements can be used to confirm the presence of a coating. There are also other methods that are suitable for detecting the presence of specific functional groups, for instance:

titration to detect acidic functional groups, e.g. to detect free carboxylic acid moieties, or determination of amine groups on a polystyrene bead by ultraviolet (UV) spectroscopy.

Characterisation of Crosslinking

A method for determining the level of cross-linking by ascertaining the amount of swelling induced by solvent and correlating this with known standards has previously been described in this specification. For a more detailed discussion of characterisation of crosslinking, the reader is referred to Harrison, D J P, Yates, W R and Johnson, J F (1985) 'TECHNIQUES FOR THE ANALYSIS OF CROSS-LINKED POLYMERS', Polymer Reviews, 25:4, 481-549. Methods based on the swelling of polymers are described on pages 494-504 of this publication. Harrison eta/describe a number of techniques to measure swelling, both volumetric and gravimetric.

The swellability of a polymer when contacted with a particular solvent depends on the polymer class to which the polymer belongs, e.g. the solubility of polystyrene and a polyacrylate in a particular solvent may differ widely. It is therefore necessary for the known particles used as standards to determine swellability to belong to the same polymer class as the test particle/particle population. The polymer class may be determined by known analytical techniques, in particular mass spectrometry, where pyrolysis mass spectrometry is especially useful to determine polymer class of cross linked polymers. FTIR and NMR may also help resolve the polymer class. The application of mass spectrometry to polymer analysis is described in S. D. Hanton, Mass Spectrometry of Polymers and Polymer Surfaces, *Chem. Rev.* 2001, 101, 527-569. A more detailed account of pyrolysis mass spectrometry may be found in Kuangnan Qian, William E. Killinger, and Melissa Casey, Analytical Rapid Polymer Identification by In-Source Direct Pyrolysis Mass Spectrometry and Library Searching Techniques, Anal. Chem. 1996, 68, 1019-1027.

The degree of cross-linking of an unknown polymer particle population may therefore be determined by analysing a specimen particle or particle group to determine the polymer class, and then by comparing the swellability of the unknown particles in a solvent with the swellability in the same solvent of a plurality of standards belonging to the same polymer class.

Accordingly, by comparing the swelling of an unknown polymer sample against comparable standards, the degree of cross-linking (expressed as the amount of crosslinker monomer used in manufacture as discussed above) may be determined or approximated.

The examples below are given so as to illustrate the practice of this invention. They are not intended to limit or define the entire scope of this invention. The reagents employed in the embodiments below are commercially available or can be prepared using commercially available instrumentation, methods, or reagents known in the art. The examples illustrate various aspects of the invention and practice of the methods of the invention. The examples are not intended to provide an exhaustive description of the many different embodiments of the invention. Thus, although the foregoing invention is described in some detail by way of illustration and example for purposes of clarity of understanding, those of ordinary skill in the art will realize readily that many changes and modifications can be made thereto without departing from the spirit or scope of the appended claims.

EXAMPLES

Synthesis of Seed Particles

In embodiments, the seed is synthesised comprising monomer (M), styrene; a water-soluble initiator (I), potassium persulfate or ammonium persulfate; a surfactant (S), sodium dodecylsulfate (SDS); optionally a buffer, borax; and a chain transferring agent (T), bromotrichloro methane, alkyl mercaptans. The polymerisation procedure is an emulsion polymerisation performed with a surfactant below the critical micelle concentration. The seed synthesis follows generally the same procedures for seeds formed by emulsion polymerisation as that described in WO00/61647 (incorporated herein by reference in its entirety). The difference in the comparable procedures is:

The type and amount of surfactant is changed. SDS is used in the present procedure, with the concentration of SDS varied between 1 and 2 g/L. In the examples given below, the SDS used had a purity of ≥98.5%.

The present synthesis involves the addition of the chain transferring agent (T). The chain transfer agent is added after the commencement of nucleation, e.g., at a concentration of at least 1.5 mmol/L water and not more than 45 mmol/L water. The occurrence of nucleation is detected by the emulsion becoming cloudy, for example turning white when styrene is used as the monomer.

Example 1: Synthesis of Low Molecular Weight Seed Particles

Preparation of initial seed particles with a weight average molecular weight of $1.8 \times 10^4$ gram/mol and a mode diameter of 0.12 µm.

Figure 3:
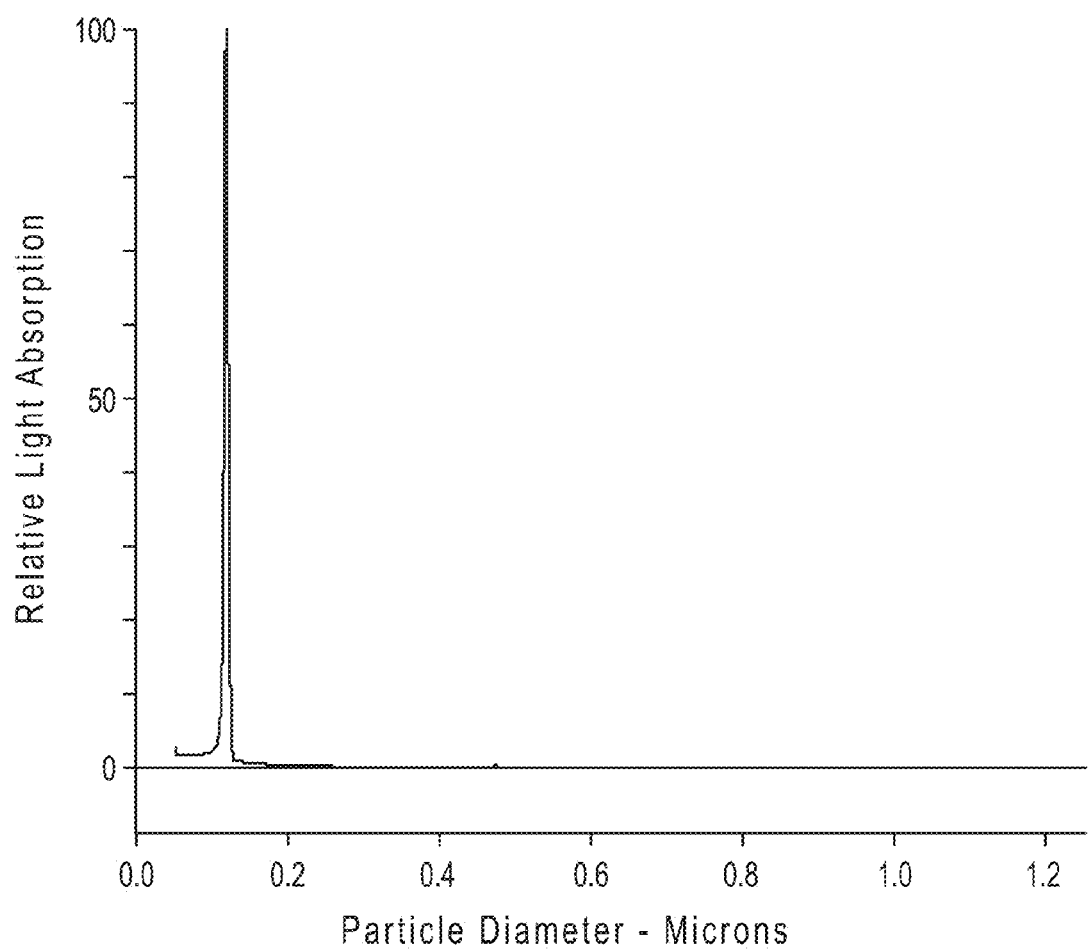
FIG. 3 illustrates the diameter and coefficient of variation (CV %) of the diameter obtained by disc centrifugation for polystyrene seed particles formed according to the procedure of Example 1, with a weight average CV of the main peak of 4% as determined from the diameter range of 0.1-0.17 μm.

84.6 g styrene was extracted with 150 ml 10 wt % sodium hydroxide, then washed with water to pH7 and then flushed with argon for 10 min. In a 2 L reactor, 1733 g of water and 0.59 g of borax were heated to 80° C., and 50 g water was evaporated off under reduced pressure to remove oxygen. Then 2.25 g sodium dodecyl sulfate (SDS) in 20 ml boiled water was added and the mixture was stirred for 10 min, then the washed and substantially oxygen free styrene was added and the mixture was stirred for a further 15 min. 3.08 g ammonium persulfate in 107 ml boiled water was then added. After 5 minutes the emulsion turned white. After an additional 10 minutes 5.5 gram of 1-octanethiol was added. The mixture was kept at 80° C. in an argon atmosphere for 20 hours. A dispersion of monosized polymeric particles was formed having a particle mode diameter of 0.12 µm determined by disc centrifugation, as illustrated in FIG. 3.

Example 2: Synthesis of Low Molecular Weight Seed Particles

Preparation of initial seed particles with a weight average molecular weight of $1.16 \times 10^4$ gram/mol and a z average diameter of 0.14 µm.

84.7 g styrene was extracted with 150 ml 10 wt % sodium hydroxide, then washed with water to pH7 and then flushed with argon for 10 min. In a 2 L reactor, 1720 g of water and 0.59 g of borax were heated to 80° C., and 50 g water was evaporated off under reduced pressure to remove oxygen. Then 2.34 g sodium dodecyl sulfate (SDS) in 20 ml boiled water was added and the mixture was stirred for 10 min, then the washed and substantially oxygen free styrene was added and the mixture was stirred for a further 15 min. 3.08 g ammonium persulfate in 100 ml boiled water was then added. After 5 minutes the emulsion turned white. After an additional 10 minutes 2.38 mL bromotrichloromethane was continuously added at a rate of 0.05 mL/min. The mixture was kept at 80° C. in an argon atmosphere for 12 hours. A monodisperse suspension of polymeric particles was formed having a z average diameter of 0.14 μm determined by photon correlation spectroscopy.

Example 3: Synthesis of Low Molecular Weight Seed Particles

Preparation of initial seed particles with a weight average molecular weight of $1.0 \times 10^4$ gram/mol and a z average diameter of 0.15 μm.

98.7 g styrene was extracted with 175 ml 10 wt % sodium hydroxide, then washed with water to pH7 and then flushed with argon for 10 min. In a 2 L reactor, 2000 g of water and 0.68 g of borax were heated to 80° C., and 50 g water was evaporated off under reduced pressure to remove oxygen. Then 2.62 g sodium dodecyl sulfate (SDS) in 20 ml boiled water was added and the mixture was stirred for 10 min, then the washed and substantially oxygen free styrene was added and the mixture was stirred for a further 15 min. 3.59 g ammonium persulfate in 101 ml boiled water was then added. After 7 minutes the emulsion turned white. After an additional 10 minutes 6.4 g bromotrichloromethane was added. The mixture was kept at 80° C. in an argon atmosphere for 18 hours. A monodisperse suspension of polymeric particles was formed having a z average diameter of 0.15 μm determined by photon correlation spectroscopy.

Application of the Ugelstad Process to Form Polymer Particles From Seed Particles Reaction scheme 1 illustrates, in general terms, an embodiment of the Ugelstad process that can be used to create submicron polymer particles. In reaction scheme 1, the seed particle contains P, a low molecular weight polymer. Y is an organic molecule with a suitably low water solubility, which may also be a polymerisation initiator, for example dioctanoylperoxide. The weight ratio Y/P is of the order of 1 to 3 after the activation step. In the next step one or more monomers are added, for instance the illustrated monomers 1,3-divinylbenzene and styrene, optionally with a porogen, such as toluene. The weight ratio of (monomer plus porogen) to polymer may be 60 to 100. After allowing the one or more monomers to swell the activated seed particle, the monomers are polymerised, forming the polymer particles.

Reaction Scheme 1

SEED; P  ACTIVATION
Low Mwt*  Hydrophobic
              Y emulsion
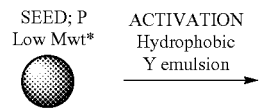
→

-continued
M/P ~ 60-100

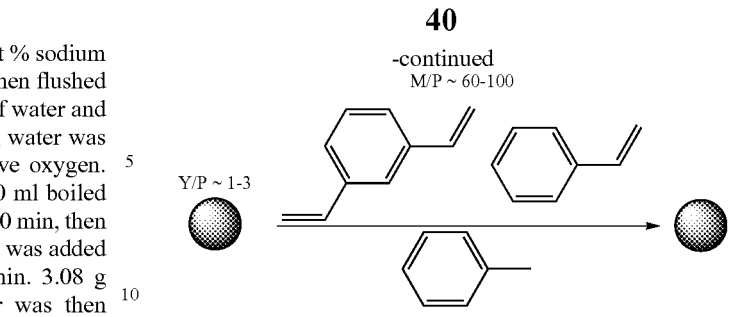

Example 4: Synthesis of Polymer Particles From Low Molecular Weight Seed Particles 17.8 g SDS, 1480 g water, 74 g acetone and 148.0 g dioctanoylperoxide were mixed with an ultraturax type Ystral™ X10/25 homogeniser ("ultraturax") for 3 minutes and homogenised with a pressure homogeniser for 10 minutes (=initiator emulsion).

330.9 g toluene, 118.7 g 65% divinylbenzene (DVB) (comprising 74.8 g DVB and 43.9 g ethylvinylbenzene), 30 g styrene, 44.5 g polyvinylpyrrolidone (PVP) K-30, 2.7 g SDS and 2827.0 g water were mixed by ultraturax for 4 minutes, and further homogenised for 30 minutes (=monomer emulsion).

In a 0.5 L reactor 23.3 g of the seed particle dispersion prepared according to Example 1 was gently mixed with 25.9 g of the initiator emulsion. The mixture was stirred at 25° C. for 24 hours.

In a 0.5 L reactor 22.4 gram of the activated seed particles and 344.3 gram of the monomer emulsion was added. The mixture was stirred for 2 hours at 25° C. and then 133.4 g water was added, and the mixture was then heated to 60° C. After 1 hour at 60° C. the temperature was raised to 70° C. and maintained at this temperature for 20 hours.

The dispersion was repeatedly washed with methanol, then air dried over night followed by a further 15 hours of drying at 50° C.

Figure 4:
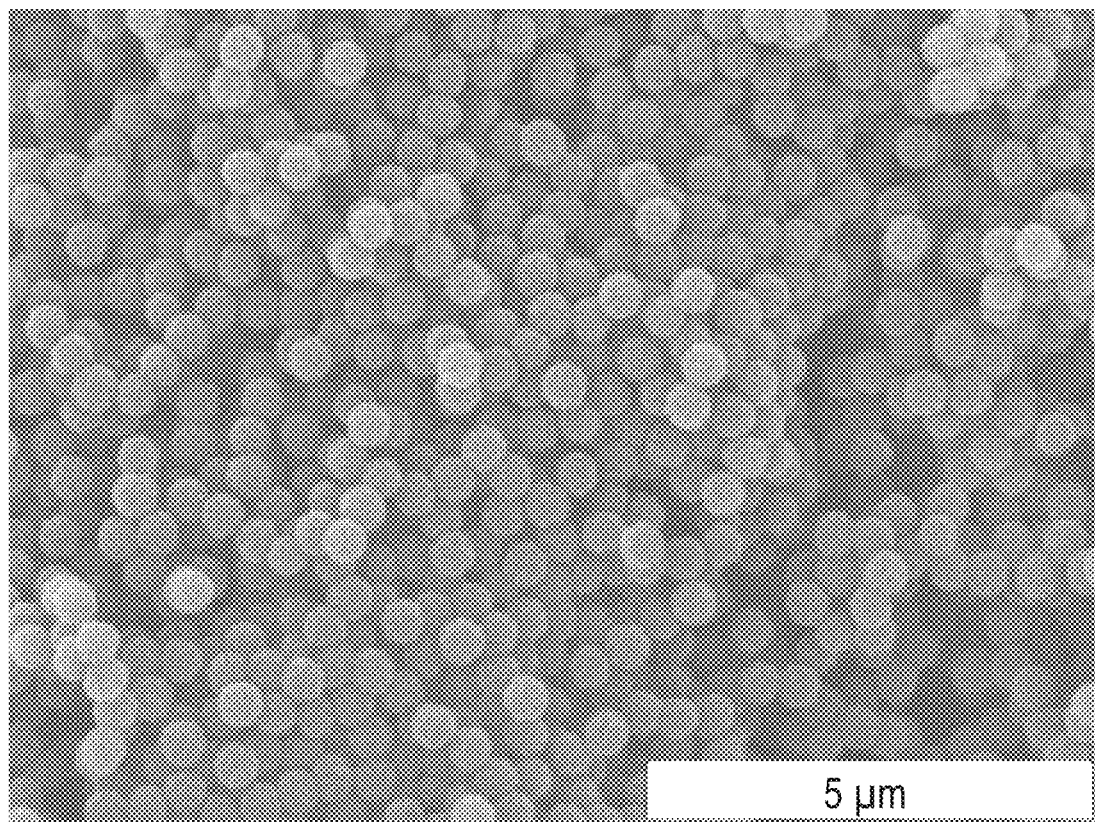
FIG. 4 is an SEM images of submicron polymer particles, formed by application of an Ugelstad process to seed particles comprising low molecular weight polymer.

FIG. 4 is an SEM showing the resulting particle morphology and uniform size. The diameter of the particles is estimated to be 0.54 μm from FIG. 4.

Example 5: Synthesis of Polymer Particles From Low Molecular Weight Seed Particles The initiator emulsion and the monomer emulsion composition were prepared as described in Example 4. In a 0.25 L reactor, 40.7 g of the seed particle dispersion prepared according to Example 2 was gently mixed with 49.9 g of the initiator emulsion. The mixture was stirred at 25° C. for 24 hours. In a 0.5 L reactor 36.3 gram of the activated seed particles and 335.0 gram of the monomer emulsion was added. The mixture was stirred for 2 hours at 25° C., then 133.4 g water was added, and then the mixture was heated to 60° C. After 1 hour at 60° C. the temperature was raised to 70° C. and maintained at this temperature for 20 hours.

The dispersion was repeatedly washed with methanol and air dried over night followed by a further 15 hours of drying at 50° C.

Figure 5:
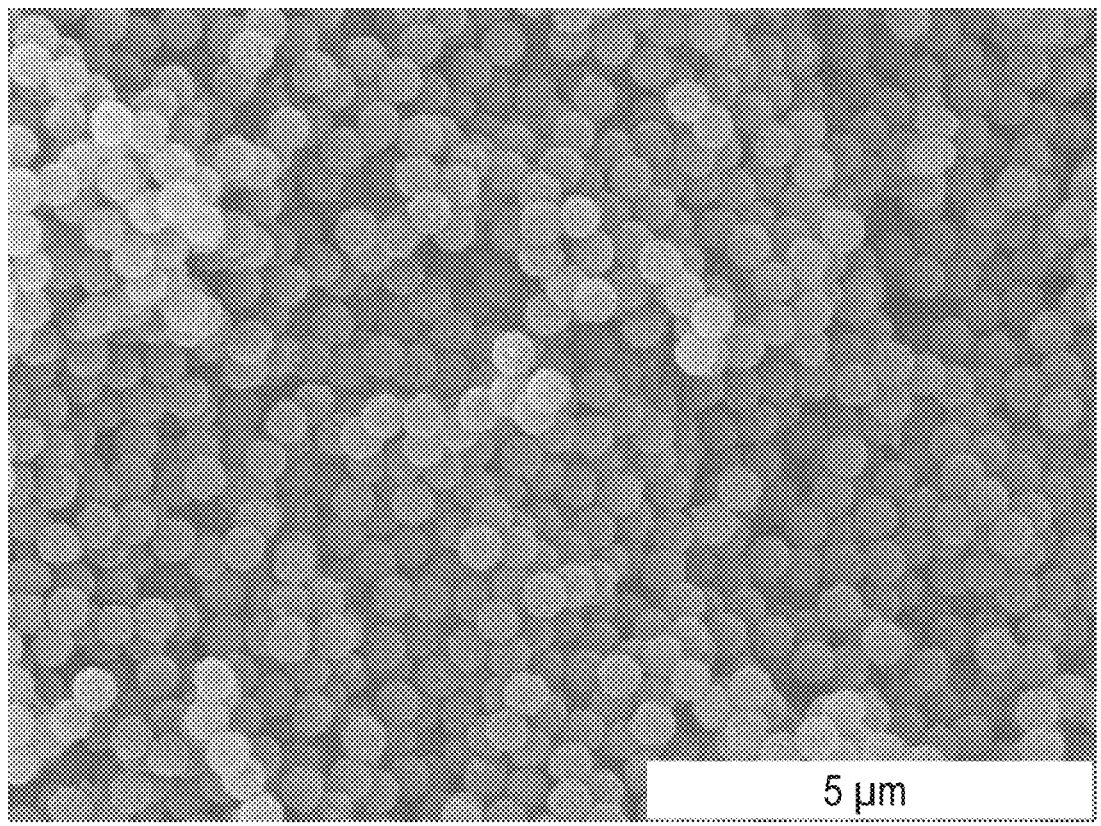
FIG. 5 is an SEM image of submicron polymer particles, formed by application of an Ugelstad process to seed particles comprising low molecular weight polymer.

FIG. 5 is an SEM showing the resulting particle morphology and uniform size. The diameter of the particles is estimated to be 0.52 μm from FIG. 5.

Example 6: Synthesis of Polymer Particles From Low Molecular Weight Seed Particles The initiator emulsion and the monomer emulsion composition were prepared as described in Example 4. In a 0.25

L reactor, 50.6 g of the seed particle dispersion prepared according to Example 3 was gently mixed with 47.8 g of the initiator emulsion. The mixture was stirred at 25° C. for 24 hours. In a 0.5 L reactor, 31.7 gram of the activated seed particles and 333.8 gram of the monomer emulsion was added. The mixture was stirred for 2 hours at 25° C., then 133.0 g water was added, and the mixture was then heated to 60° C. After 1 hour at 60° C. the temperature was raised to 70° C. and maintained at this temperature for 20 hours.

Figure 6:
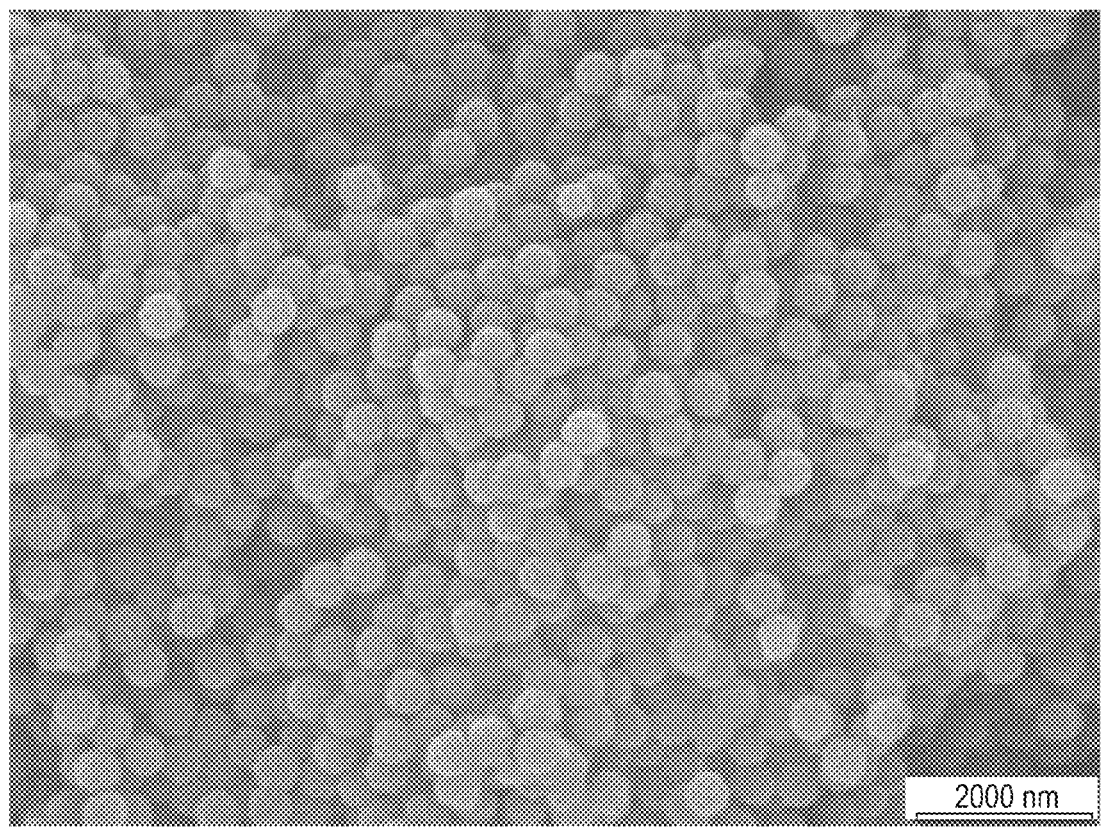
FIG. 6 is an SEM image of submicron polymer particles, formed by application of an Ugelstad process to seed particles comprising low molecular weight polymer.

FIG. 6 is an SEM showing the resulting particle morphology and uniform size.

Example 7: Analysis of Seed Particles Made Under Different Conditions

Figure 7:
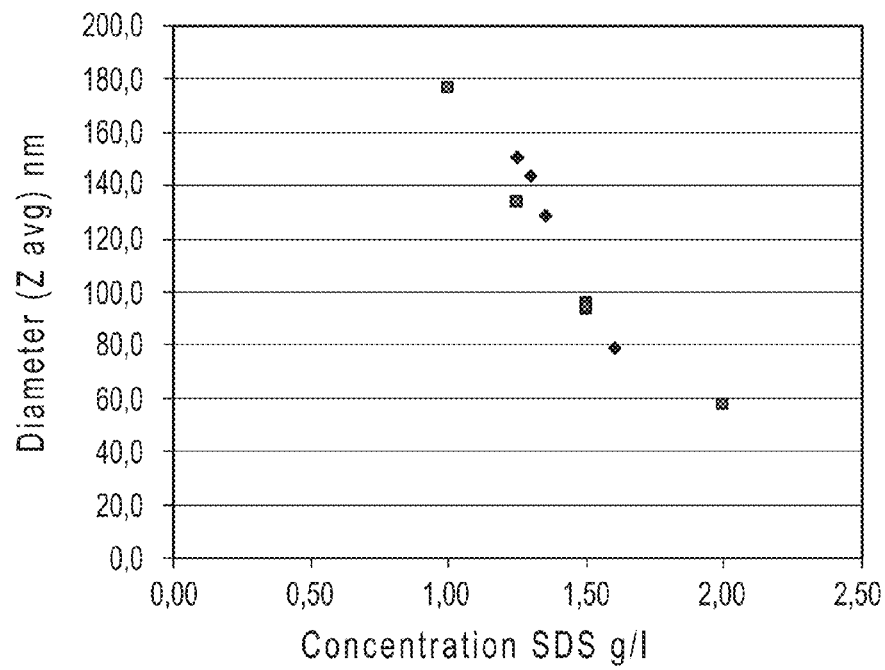
FIG. 7 is a graph illustrating how seed particle diameter is affected by sodium dodecyl sulfate (SDS) concentration, both with (diamond data points) and without (square data points) the presence of a chain transfer reagent.

Table 1 and FIG. 7 illustrate how the size of the starting polystyrene seed particle can be controlled by adjusting the concentration of the surfactant SDS in the aqueous dispersion used for emulsion polymerisation, while keeping the concentration of the polymer and initiator constant. Diamond data points are for syntheses including the chain transfer agent (T) and square data points are for reactions without T. Particle sizes obtained were from 0.058 μm-0.20 μm, with most from 0.09 nm to 0.16 nm. As can be seen from the data, seed particle size is related to SDS concentration, with a higher concentration of SDS resulting in a smaller seed particle. The presence or absence of T during seed synthesis did not have a significant effect on seed particle size.

TABLE 1

SDS concentration and particle diameter

| sample ID | | SDS concentration gram/liter water | particle diameter (z average) nm | polymer weight average molecular weight |
|---|---|---|---|---|
| LI541 | a-1 | 1 | 177 | 8.4E+04 |
| LI542 | a-2 | 1.25 | 134 | 9.1E+04 |
| LI532 | a-3 | 1.5 | 94 | 1.2E+05 |
| LI534 | a-4 | 1.5 | 94 | 1.5E+05 |
| LI537 | a-5 | 1.5 | 95 | 1.4E+05 |
| LI538 | a-6 | 1.5 | 96 | 1.4E+05 |
| LI509 | a-7 | 2 | 58 | 2.4E+05 |
| LI662 | b-1 | 1.25 | 151 | 1.6E+04 |
| LI728 | b-2 | 1.25 | 151 | 1.0E+04 |
| LI740 | b-3 | 1.25 | 151 | 1.2E+04 |
| LI794 | b-4 | 1.3 | 144 | 1.2E+04 |
| LI804 | b-5 | 1.35 | 129 | 1.3E+04 |
| LI670 | b-6 | 1.6 | 78 | 7.4E+04 |

Figure 8:
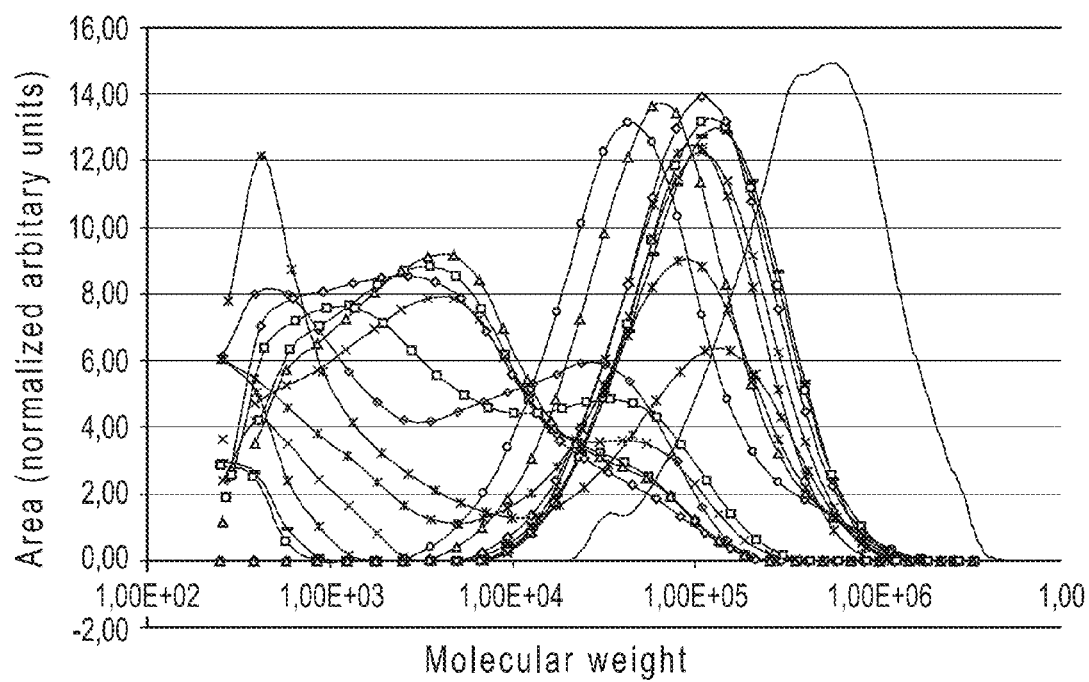
FIG. 8 is a graph illustrating the molecular weight distribution of various polystyrene seed particles, as measured by gel permeation chromatography (GPC)

Samples a-1 to a-7 are without T and b-1 to b 6 are with T.
Styrene concentration = [M] = 47 g/L water (0.45 mol/L water)
Initiator concentration = [I] = 1.7 g/L(7.5 mmol/l) ammonium persulfate.
T concentration (b-1 to b-6) = [T] = 15 mmol/L water The presence or absence of T did, however, have a significant effect on the molecular weight distribution of the starting seed particles, as is apparent from Table 1. The effect of T on molecular weight is also illustrated in FIG. 8. The molecular weight distributions illustrated in FIG. 8 were determined with GPC calibrated with polystyrene molecular weight standards. The curves in the graph show the differences between 4 classes of polymer seed particles, as follows:

1) Trace 20: seed particle with high molecular weight.

2) Traces 21 to 28: seed particles with a reduced molecular weight which is controlled by reducing the amount of monomer phase present during the seed synthesis, i.e. lowering of the particle number i.e. surface area gives a reduced molecular weight of the polystyrene.

3) Traces 30 to 32: seed particles synthesised with chain transfer agent added a short time after particle nucleation visible appearance (i.e., the chain transfer agent was added shortly after the solution appeared cloudy). The entire amount of chain transfer agent is added at the same time. The molecular weight is further reduced, but demonstrates a bimodal distribution.

4) Traces 40 to 42: seed particles synthesised with the chain transfer agent added over time with the initial addition shortly after the visible appearance of particle nucleation with visible appearance determined by the solution becoming cloudy.

As can be observed, T reduces the overall molecular weight distribution of the polymer. It is believed that it is able to do this by extraction of the radicals from growing polymer chains.

It is important to add T at the correct time, to obtain monosized seed particles. The chain transfer agent should therefore be added a short time after the particle nucleation step, either all at once or over a longer period of time. If T is added before particle nucleation the presence of T may alter the nucleation-step and generate polydisperse seed particles.

Disc centrifuge analysis of the seed particle samples plotted in FIG. 8, revealed coefficients of variation below <5% for all of the seed particle populations.

Example 8: Analysis of Further Seed Particles

The average molecular weights were measured for a number of other samples, as illustrated in Table 2, with samples listed as seed type "high" and "med." ("medium") representing comparative examples with polymer molecular weights above those of the seed particles of the present invention. Seed type "low" represents seed particles made according to methods analogous to those of Examples 1 to 3.

TABLE 2

Molecular weight data for seed particles obtained by GPC analysis

| Batch-peak No. | Component RT mins | % SEC Area | Peak Mwt | Weight Average Mw | No. Average Mn | Weight Average Mw sample | seed-type |
|---|---|---|---|---|---|---|---|
| B650-1 | | | | 5.96E+05 | | 5.96E+05 | high |
| LI532-1 | 12.023 | 73.86 | 9.44E+04 | 1.19E+05 | 6.18E+04 | 8.76E+04 | med. |
| LI532-2 | 17.132 | 26.14 | 3.21E+02 | 2.50E+02 | 1.09E+02 | | |
| LI541-1 | 12.756 | 99.05 | 4.44E+04 | 8.41E+04 | 2.93E+04 | 8.33E+04 | med. |
| LI541-2 | 18.614 | 0.96 | 3.08E+01 | 2.93E+01 | 2.77E+01 | | |
| LI728-1 | 15.229 | 87.44 | 3.59E+03 | 1.01E+04 | 1.50E+03 | 8.85E+03 | low |

TABLE 2-continued

Molecular weight data for seed particles obtained by GPC analysis

| Batch-peak No. | Component RT mins | % SEC Area | Peak Mwt | Weight Average Mw | No. Average Mn | Weight Average Mw sample | seed-type |
|---|---|---|---|---|---|---|---|
| LI728-2 | 18.719 | 12.56 | 2.85E+01 | 4.74E+01 | 3.29E+01 | | |
| LI804-1 | 13.051 | 14.175 | 4.18E+04 | 6.78E+04 | 5.09E+04 | 1.28E+04 | low |
| LI804-2 | 15.3 | 55.893 | 4.27E+03 | 5.61E+03 | 2.07E+03 | | |
| LI804-3 | 17.673 | 29.933 | 2.31E+02 | 2.07E+02 | 1.59E+02 | | |
| LI662-1 | 13.224 | 53.13 | 2.78E+04 | 2.91E+04 | 1.21E+04 | 1.59E+04 | low |
| LI662-2 | 16.865 | 46.87 | 4.61E+02 | 8.91E+02 | 4.34E+02 | | |
| LI735-1 | 12.843 | 35.442 | 4.37E+04 | 4.74E+04 | 2.42E+04 | 1.80E+04 | low |
| LI735-2 | 16.095 | 50.684 | 1.38E+03 | 2.26E+03 | 1.05E+03 | | |
| LI735-3 | 18.635 | 13.874 | 3.56E+01 | 5.08E+01 | 3.39E+01 | | |

Note:
"RT" = retention time
"SEC" = size exclusion chromatography

Figure 9:
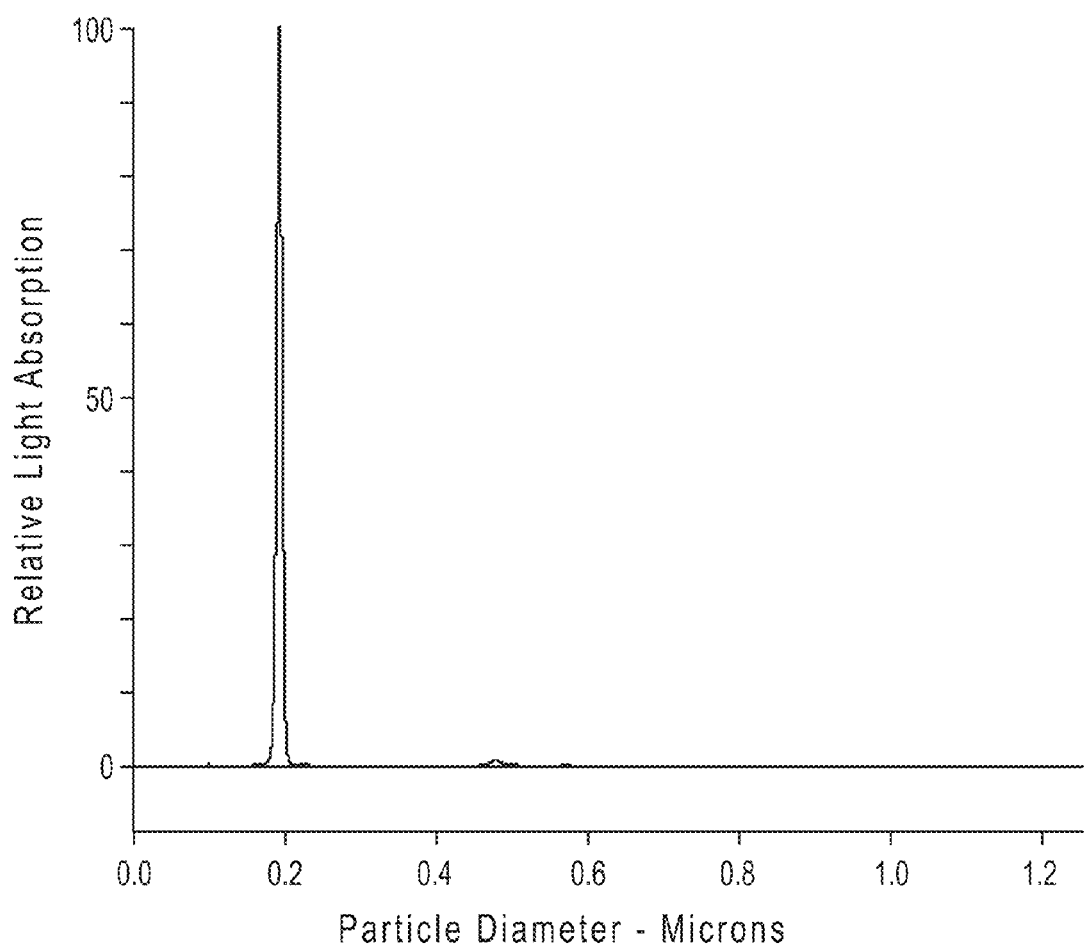
FIG. 9 illustrates the diameter and coefficient of variation (CV %) of the diameter obtained by disc centrifugation for polystyrene seed particle L1740, with a weight average CV of main peak of 2% as determined from the diameter range of 0.15-0.50 μm.

FIGS. 3 and 9 illustrate the CPS Disc Centrifugation results obtained for two representative seed particle samples. The CPS Disc Centrifugation runs used to generate the data for FIGS. 3 and 9 used a standard diameter of 0.478 µm and a speed of 19500. 2969 data points were recorded for FIG. 3 over a runtime of 110.47 minutes, while 2729 data points were recorded for FIG. 9 over a runtime of 50.74 minutes. The mode particle diameter illustrated in FIG. 3 is 0.119 µm, with a peak half width of 0.005. The mode particle diameter illustrated in FIG. 9 is 0.186 µm, with a peak half width of 0.006. The particle diameter is an overestimate, since the particles have a higher density than the polystyrene standard used. Notwithstanding this, the CV % is less than 5% for these samples.

Example 9: Analysis of Porous Polymer Particles

Figure 10A:
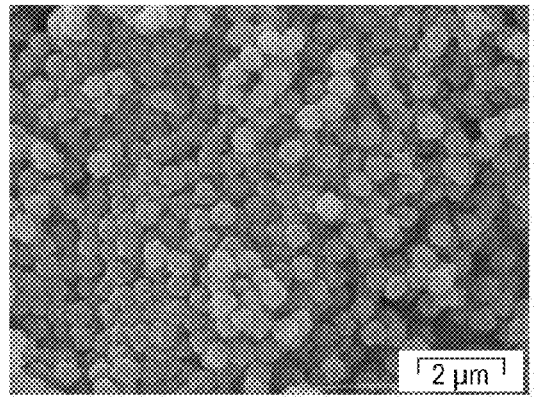
FIG. 10A, FIG. 10B, FIG. 10C, and FIG. 10D are micrographs of four different submicron porous polymer particles.
Figure 10B:
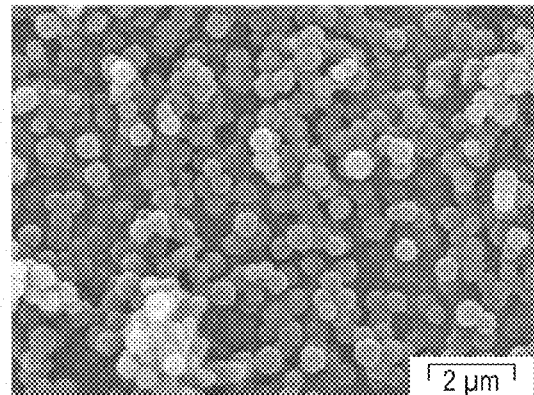
Figure 10C:
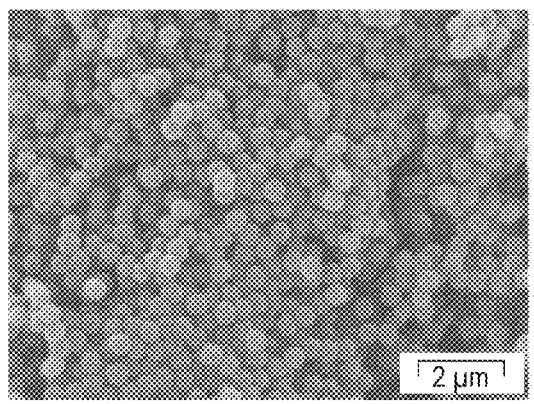
Figure 10D:
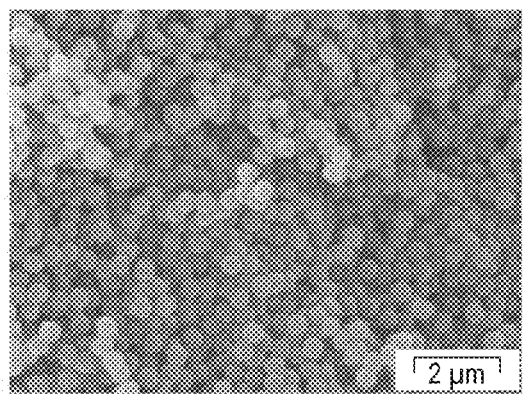

FIGS. 10A to 10D illustrate various porous polymer particles obtained after expansion of seed particles according to the Ugelstad processes. FIG. 10A illustrates, for comparison, irregular shaped particles with diameter of approximately 0.65 µm obtained from high molecular weight seed particles. FIG. 10B illustrates, for comparison, particles obtained from medium molecular weight seed particles. The particles in FIG. 10B have a diameter of approximately 0.5 µm, but a broad distribution with a large CV. The particles in FIGS. 10C and 10D illustrate particles made according to the method of Examples 4 and 5 respectively, with average particle diameters of 0.54 and 0.53 µm. In both FIG. 10C and FIG. 10D, the observed submicron particles show a narrow distribution of diameters, have smooth outer surfaces, and are approximately spherical.

Figure 11:
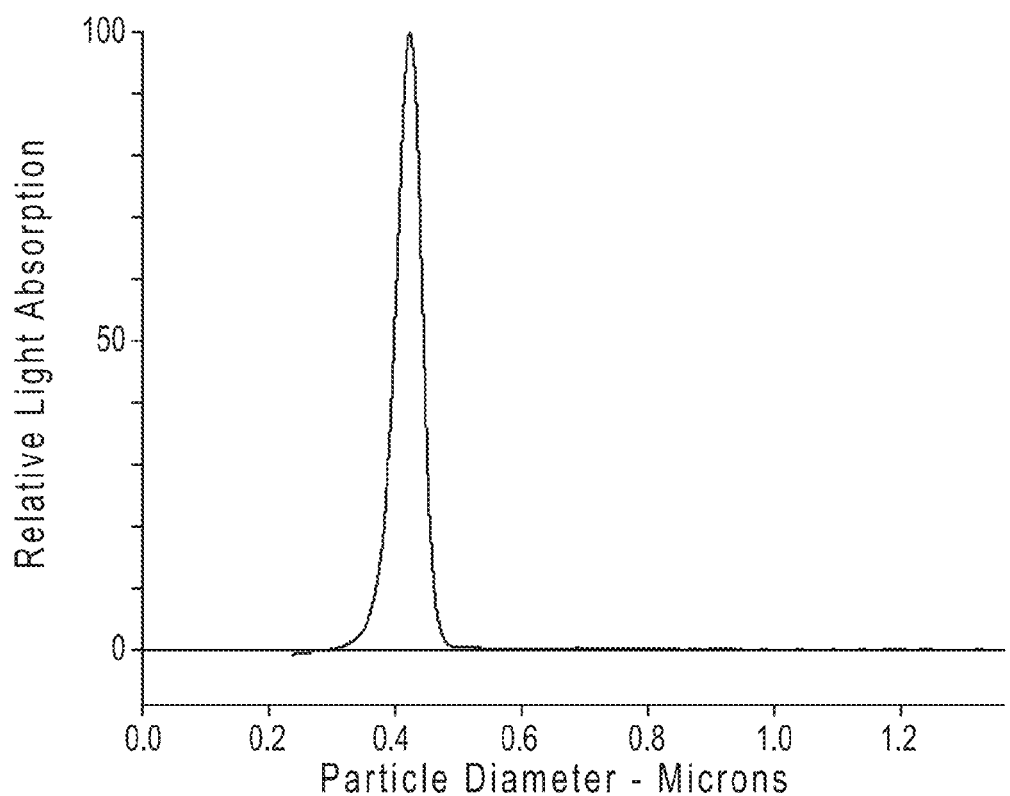
FIG. 11 illustrates the diameter and coefficient of variation (CV %) of the diameter obtained by disc centrifugation for porous polystyrene particle LK321, with a weight average CV of main peak of 8% as determined from the diameter range (0.27 μm-0.7 μm)
Figure 12:
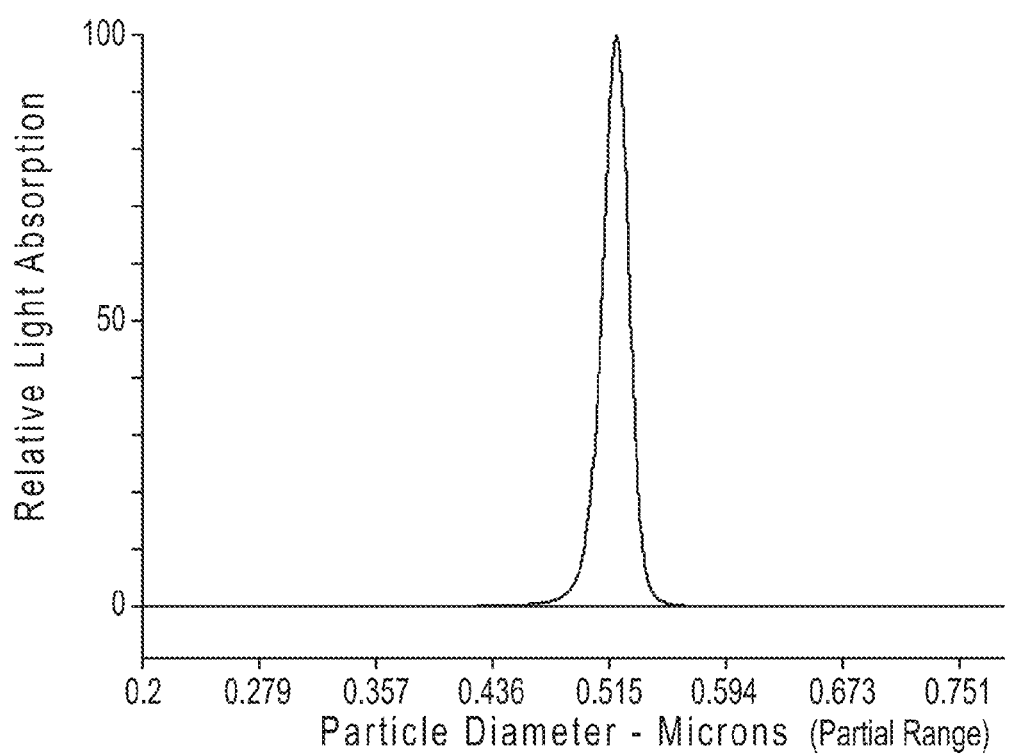
FIG. 12 illustrates the diameter and coefficient of variation (CV %) of the diameter obtained by disc centrifugation for polystyrene polymer particle L1713, with a weight average CV of main peak of 2% as determined from the diameter range (0.4 μm-0.6 μm)

The CV % for size for representative samples is illustrated in FIGS. 11 and 12. The CPS Disc Centrifugation runs used to generate the data for FIGS. 11 and 12 used a standard diameter of 0.478 µm and a speed of 19500. 1559 data points were recorded for FIG. 11 over a runtime of 4.17 minutes, while 2472 data points were recorded for FIG. 12 over a runtime of 67.87 minutes. The mode particle diameter illustrated in FIG. 11 is 0.424 µm, with a peak half width of 0.047 µm. The mode particle diameter illustrated in FIG. 12 is 0.520 µm, with a peak half width of 0.021 µm.

The surface area of the samples has been measured with a TriStar Surface Analyser and Porosity Analyser. For the porous submicron polymer particles the specific surface area for particles with 70 volume % porogen has been determined to be between 450-550 $m^2/g$. If the particles were non porous, that is no porogen was used in the Ugelstad process, polystyrene particles with a diameter of 300-900 nm would be expected to have a specific surface area of from 6 to 20 $m^2/g$.

Figure 13:
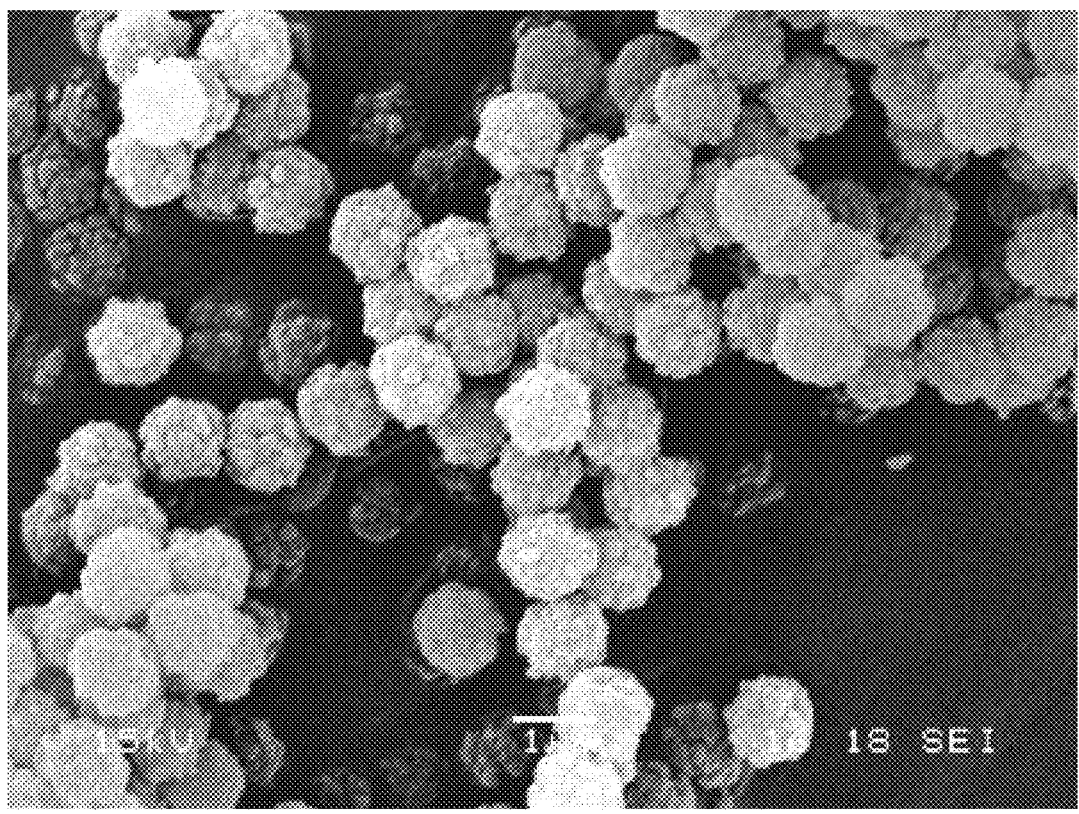
FIG. 13 is an SEM of prior art MyOne™ polymer particles.
Figure 14A:
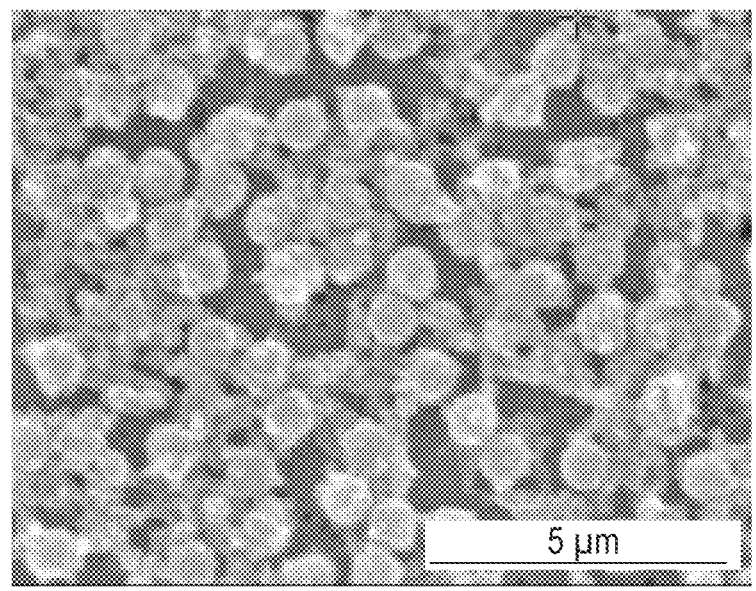
FIG. 14A, and FIG. 14B, are (a) an SEM and (b) a TEM of commercial sample 1.
Figure 14B:
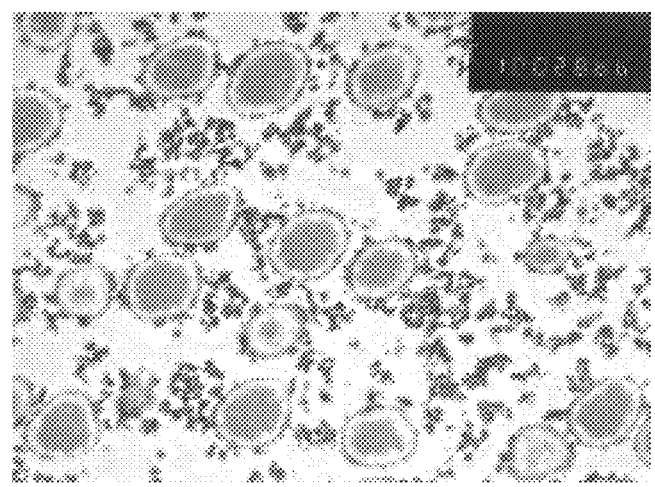
Figure 15A:
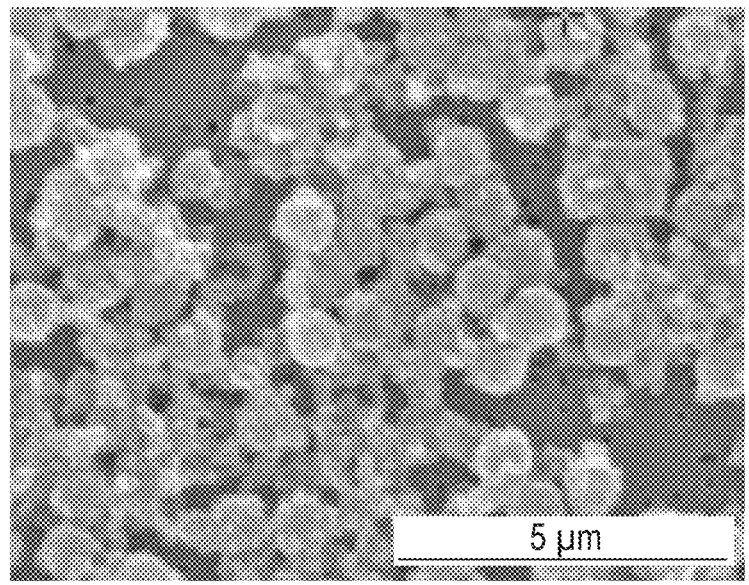
FIG. 15A and FIG. 15B, are (a) an SEM and (b) a TEM of commercial sample 2.
Figure 15B:
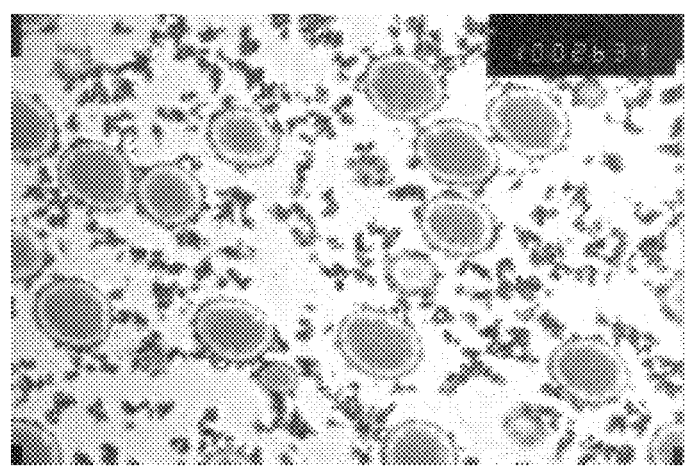
Figure 16A:
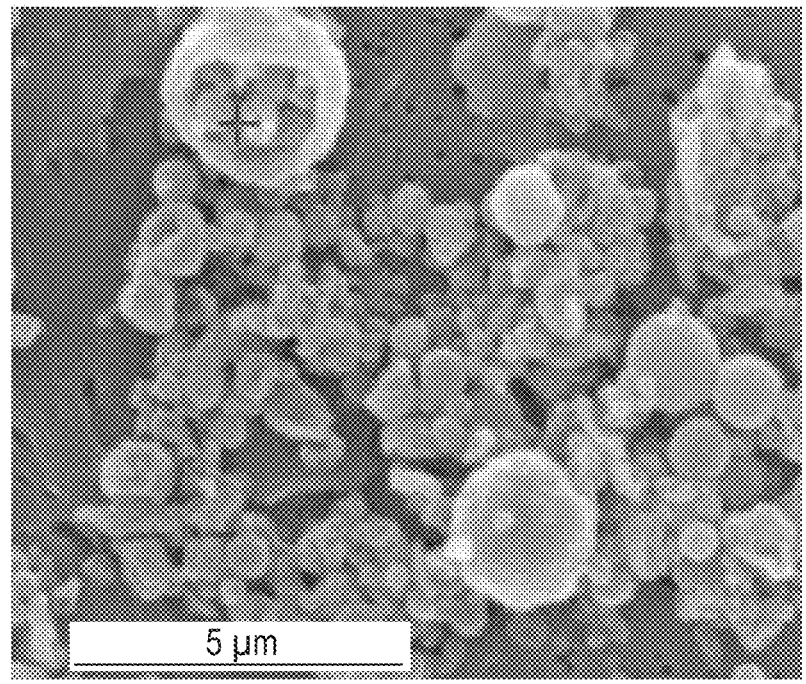
FIG. 16A and FIG. 16B, are (a) an SEM and (b) a TEM of commercial sample 3.
Figure 16B:
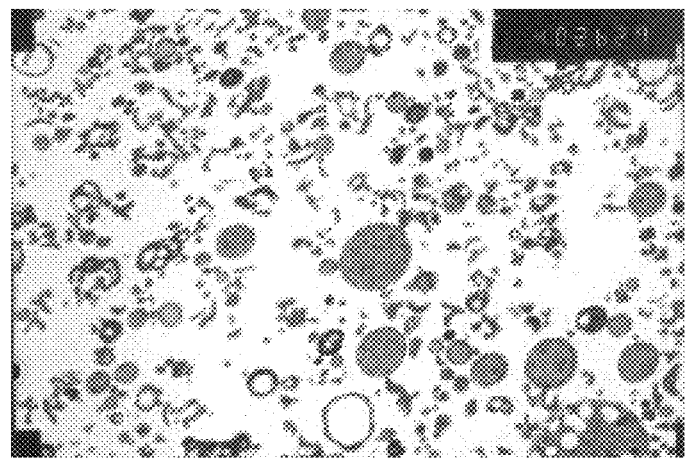
Figure 17A:
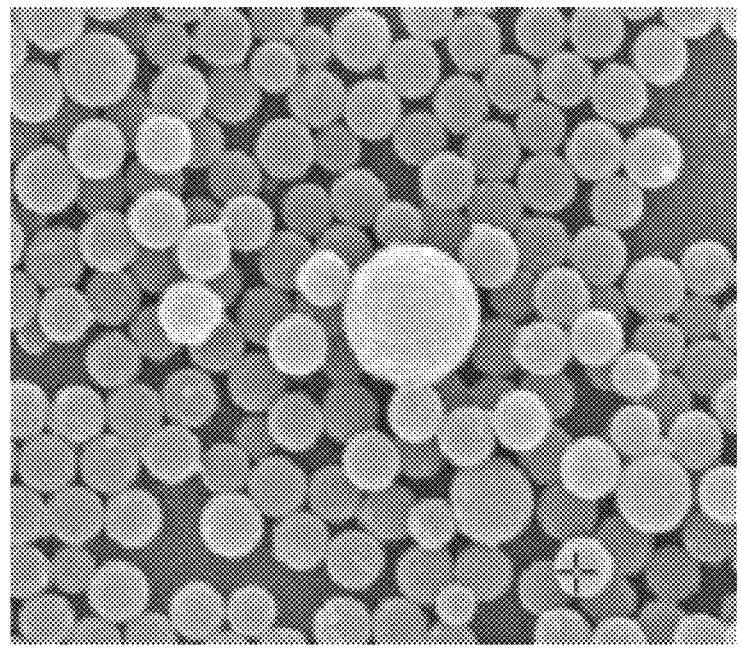
FIG. 17A and FIG. 17B, are (a) an SEM and (b) a TEM of commercial sample 4.
Figure 17B:
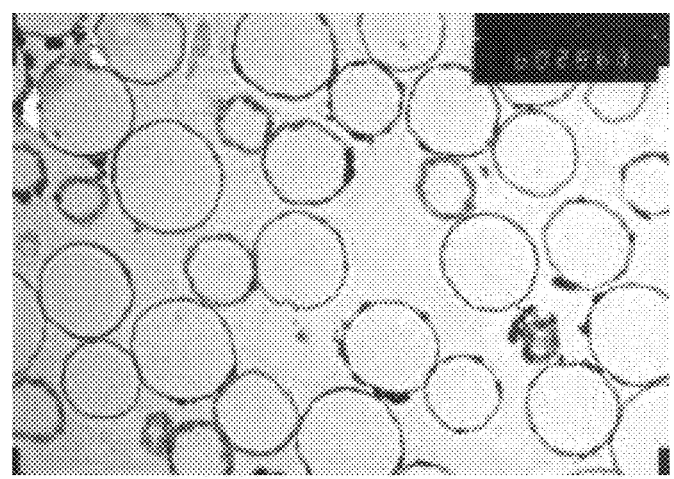
Figure 18A:
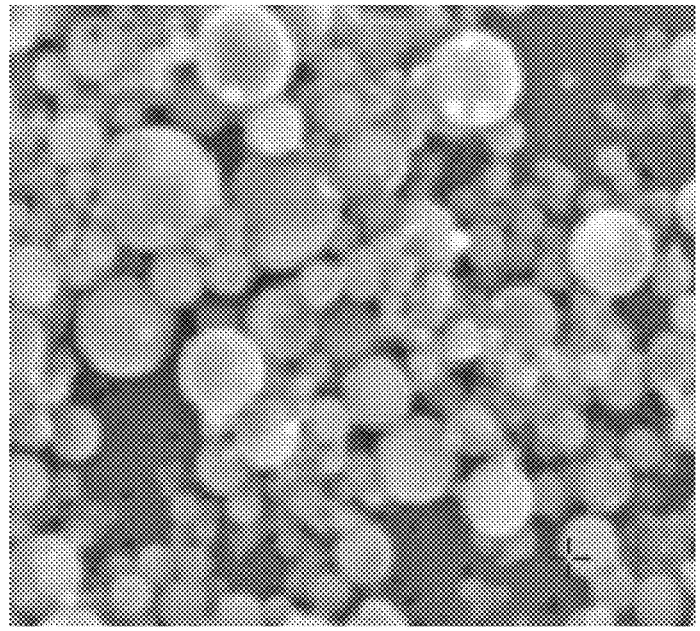
FIG. 18A and FIG. 18B, are (a) an SEM and (b) a TEM of commercial sample 5.
Figure 18B:
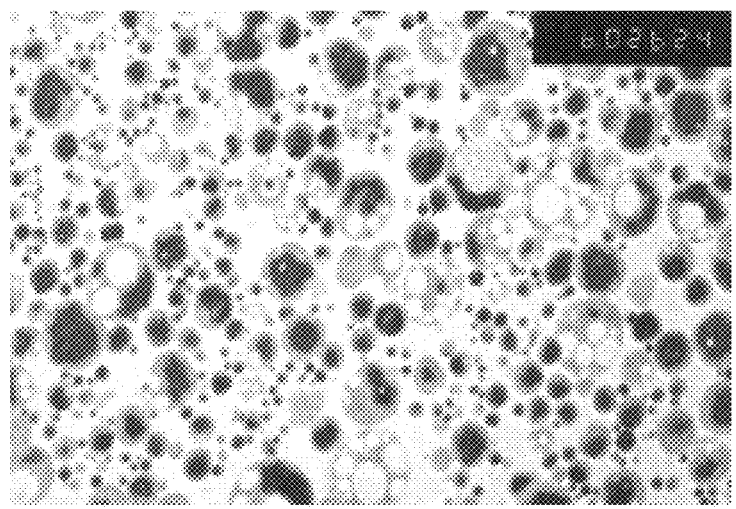
Figure 19A:
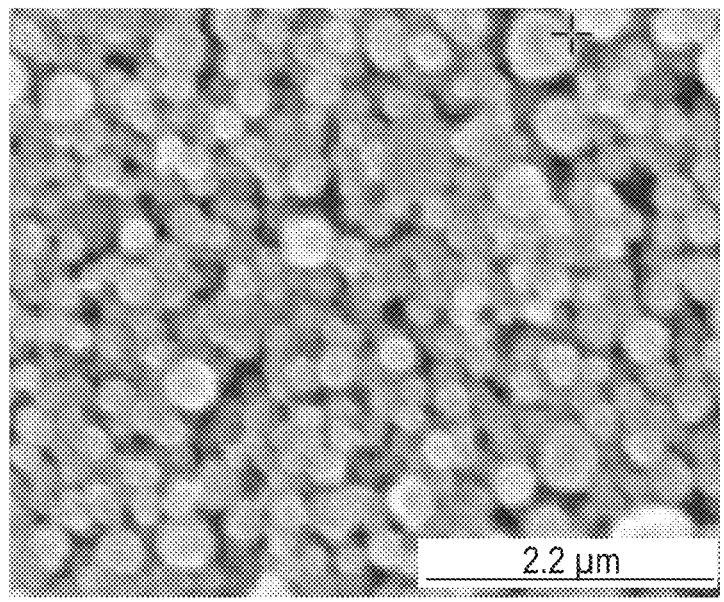
FIG. 19A and FIG. 19B, are (a) an SEM and (b) a TEM of commercial sample 6.
Figure 19B:
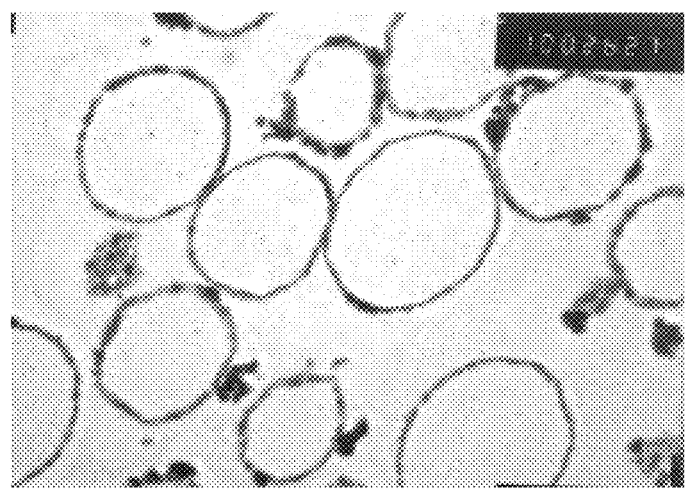
Figure 20A:
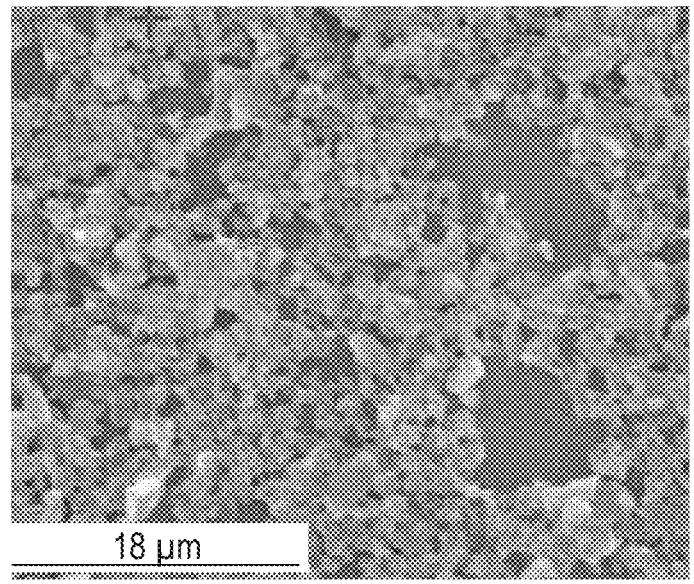
FIG. 20A and FIG. 20B, are (a) an SEM and (b) a TEM of commercial sample 7.
Figure 20B:
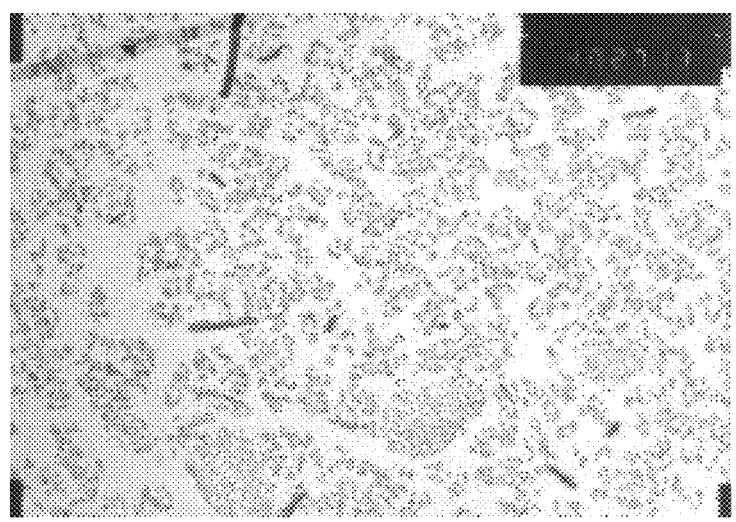
Figure 21A:
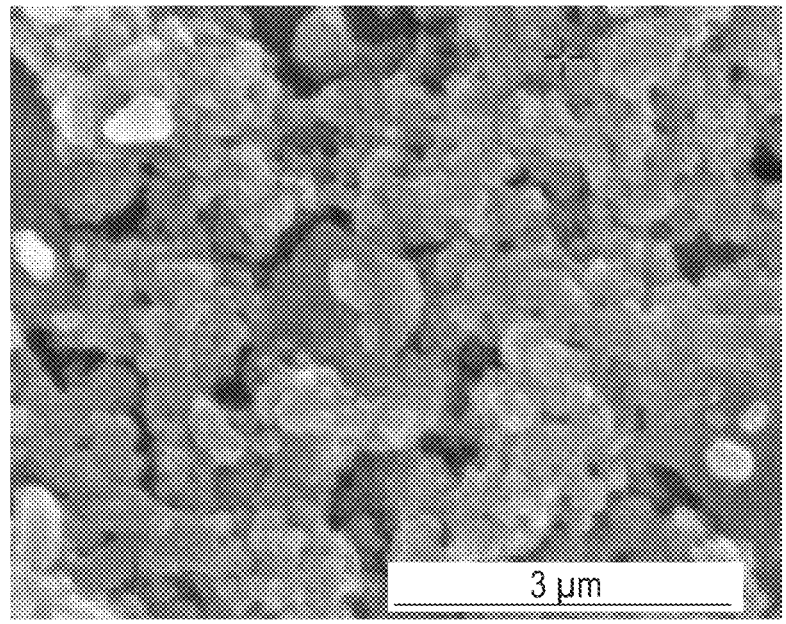
FIG. 21A and FIG. 21B, are (a) an SEM and (b) a TEM of commercial sample 8.
Figure 21B:
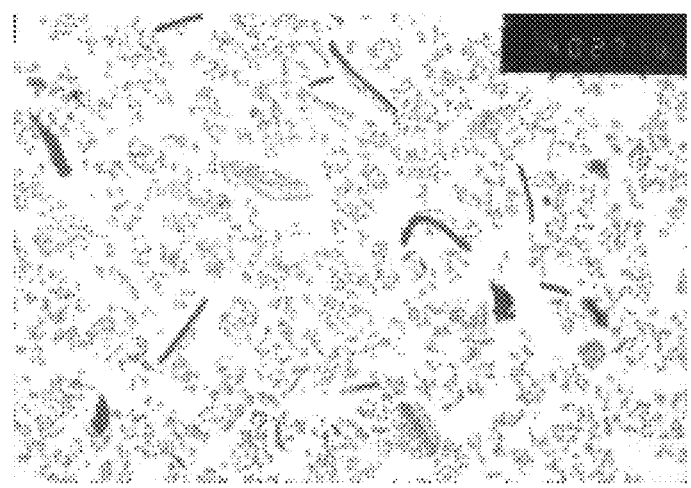
Figure 22A:
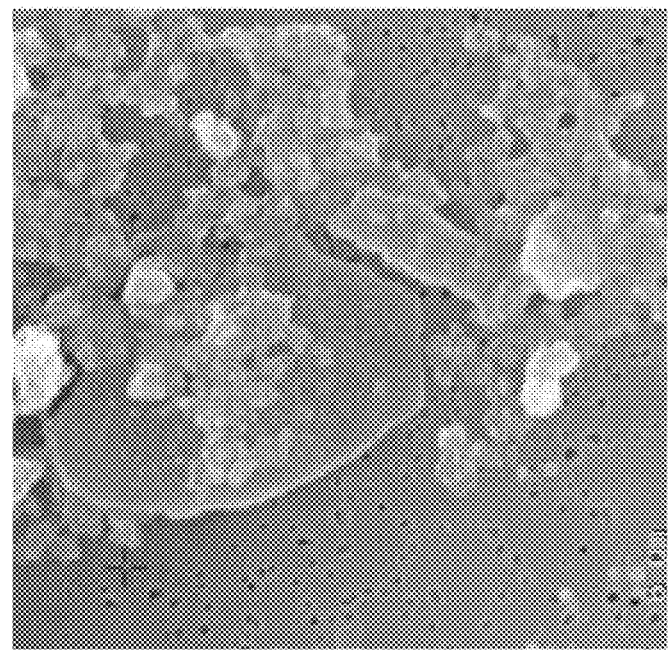
FIG. 22A and FIG. 22B, are (a) an SEM and (b) a TEM of commercial sample 9.
Figure 22B:
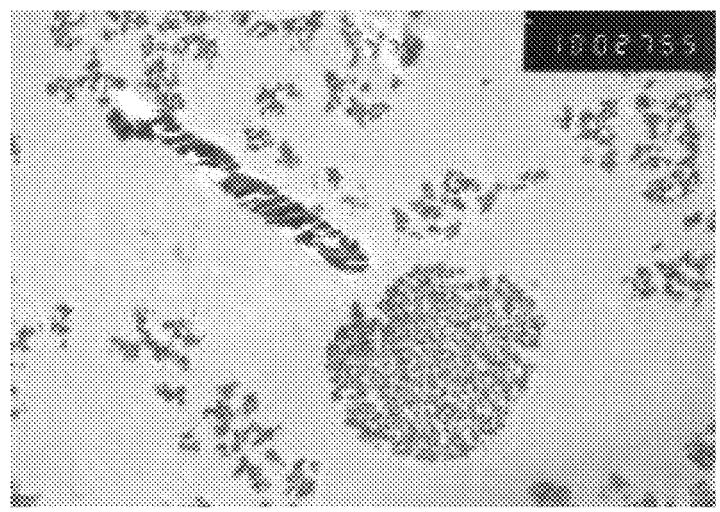
Figure 23A:
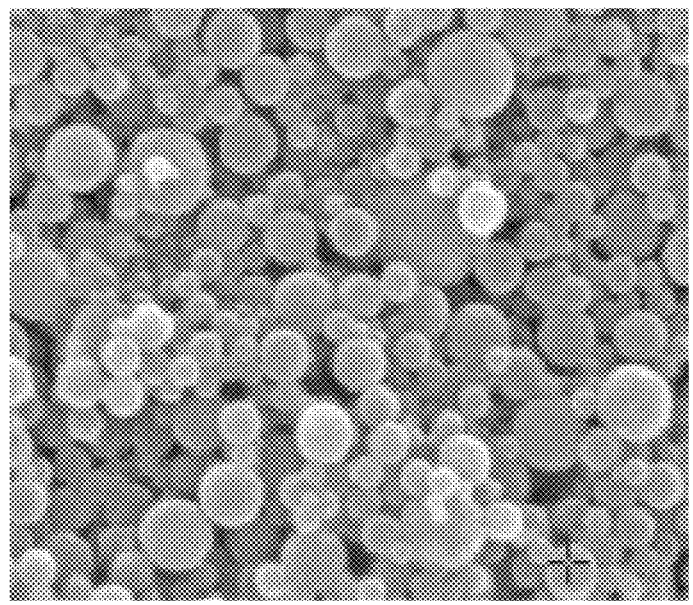
FIG. 23A and FIG. 23B, are (a) an SEM and (b) a TEM of commercial sample 10.
Figure 23B:
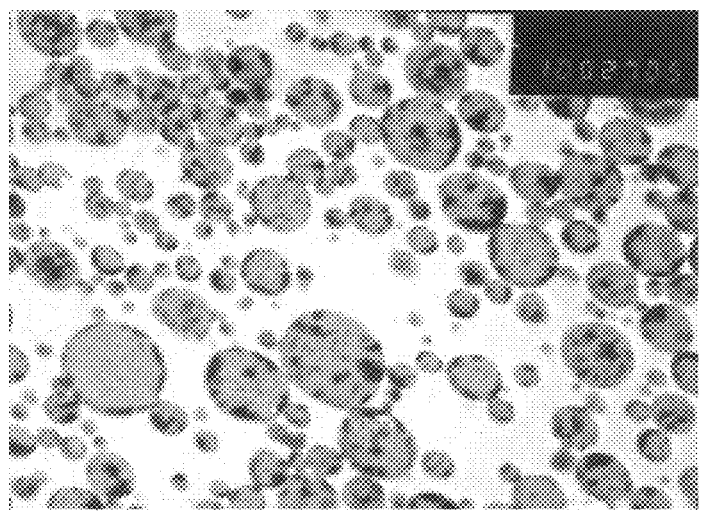
Figure 24A:
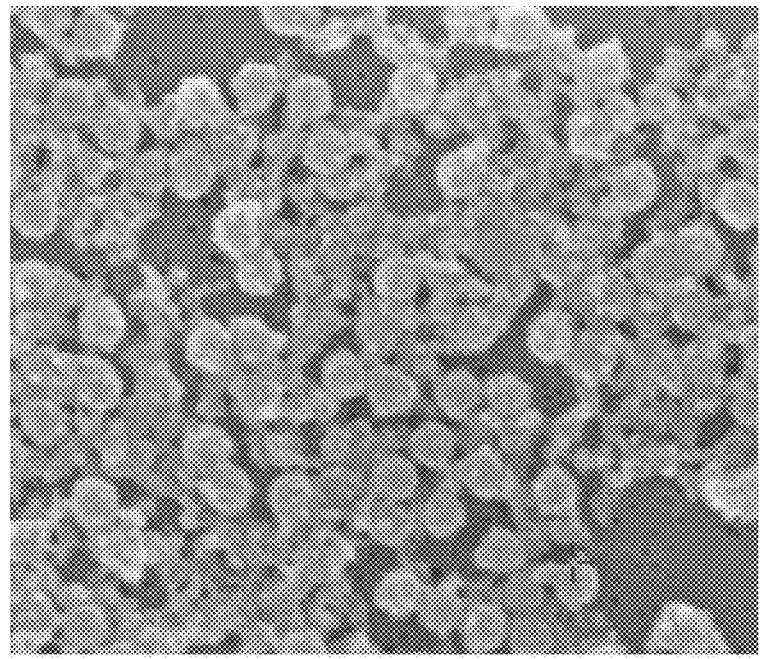
FIG. 24A and FIG. 24B, are (a) an SEM and (b) a TEM of commercial sample 11.
Figure 24B:
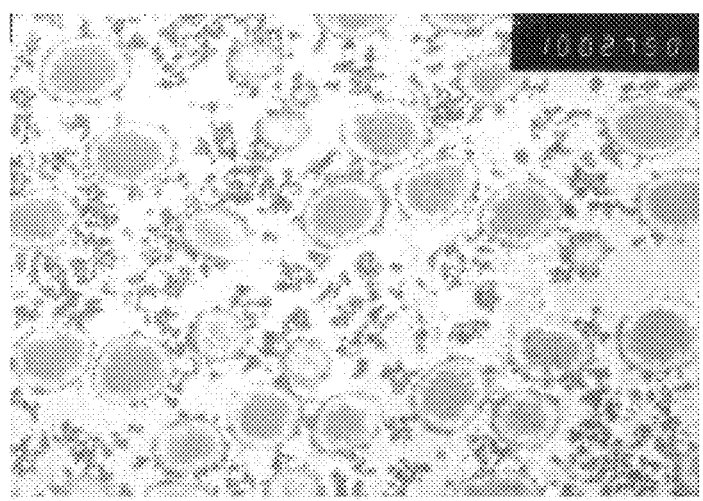
Figure 25A:
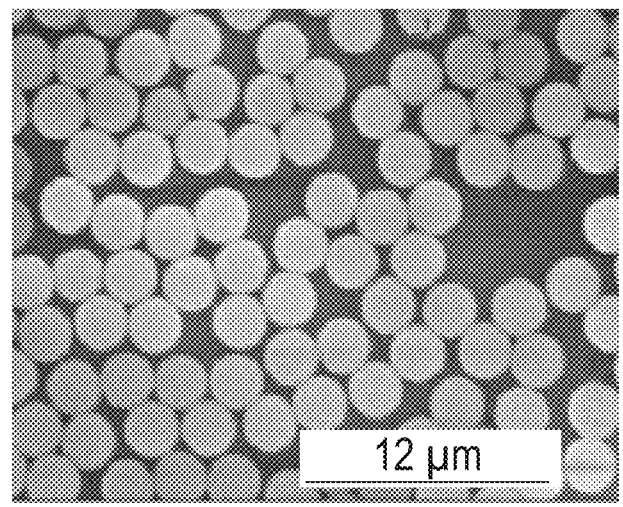
FIG. 25A and FIG. 25B, are (a) an SEM and (b) a TEM of commercial sample 12.
Figure 25B:
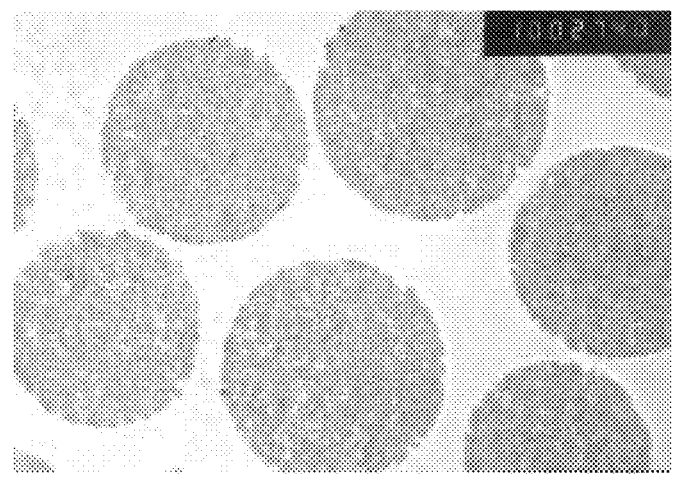
Figure 26A:
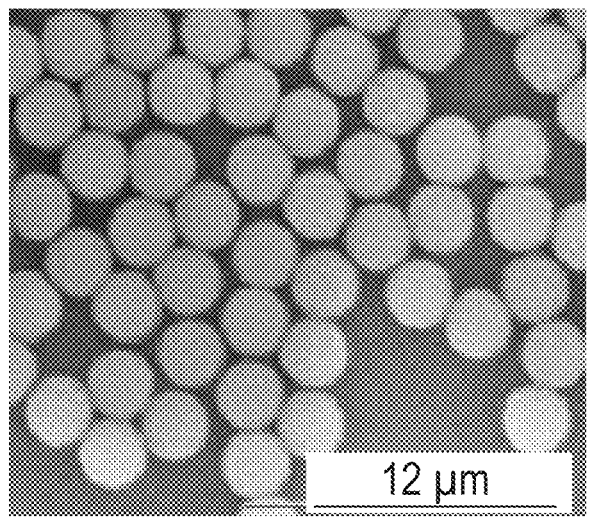
FIG. 26A and FIG. 26B, are (a) an SEM and (b) a TEM of commercial sample 13.
Figure 26B:
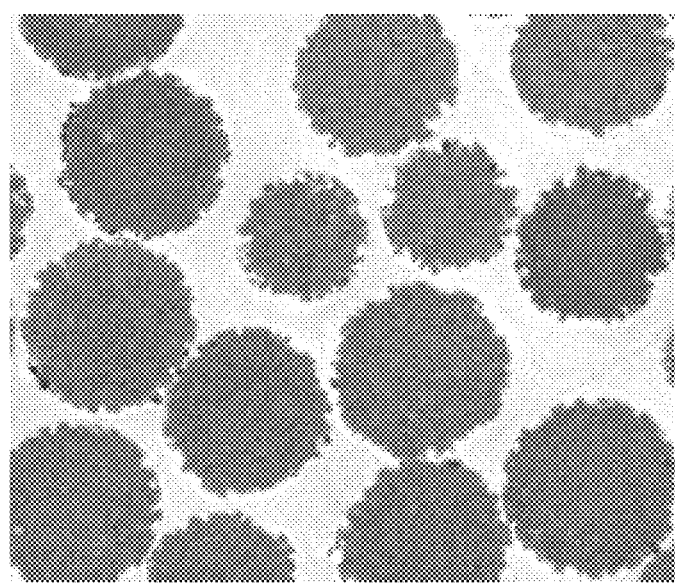
Figure 27A:
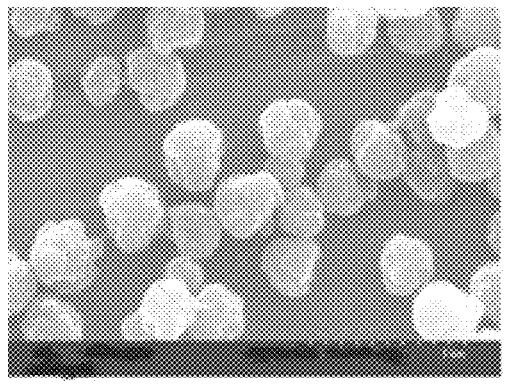
FIG. 27A and FIG. 27B shows SEM images of comparative polymer particles of two different porosities made using high molecular weight seed particles.
Figure 27B:
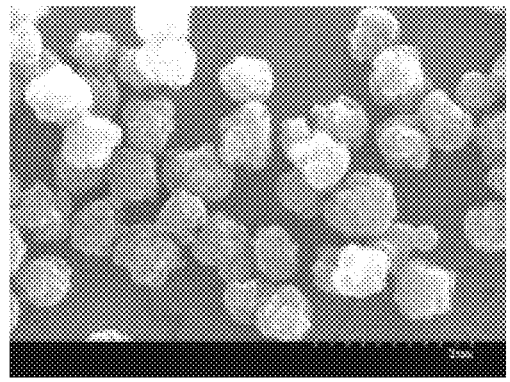

Example 10: Comparison of Size and Morphology of Porous Polymer Particles to MyOne™ Particles FIG. 13 is an SEM image taken at a magnification of 10,000 that provide a further comparison between porous polymer particles made according to the invention (e.g. as illustrated by FIG. 5) and uncoated micron sized MyOne™ polymer particles made according to example 2 of WO 2005/015216 (FIG. 13). A comparison of the SEM images of FIGS. 5 and 13 reveals important features:

The polymer particles of the present invention are smaller, that is submicron as opposed to micron sized.

The polymer particles of the present invention have a substantially smooth outer surface under a magnification of 10,000 as opposed to the rough and knobbly appearance of the outer surface of the MyOne™ polymer particles.

Example 11: Size and Morphology of Various Commercially Available Particles

The size and morphology of 13 commercially available particles were obtained for comparative purposes. Particle sizes were measured with a Coulter Counter Multisizer III™ according to the standard methods described in the manufacturer's instructions manual. The appearance was determined by examination by light microscopy and from SEM and transmission electron microscopy (TEM) images. The results are presented in table 3 and FIGS. 14 to 28 provide representative SEM and TEM images.

The results demonstrate that commercially available samples 1 to 11 comprise particles that are not monodisperse, e.g. CV % is greater than 10%. Samples 12 and 13 are monodisperse (CV<2%), but with a measured diameter of 2.85 µm. Many of these samples also appear rough and knobbly at the magnification levels displayed in the SEM and TEM images, e.g. in FIGS. 14 to 16, 18 to 22 and 24.

TABLE 3

Summary of size and morphology for commercially available particles of approximately 1 µm or larger

| No. | Product Name | Manufacturer | Stated diam. µm | Measured diam, µm | CV % (size variation, µm) | Appearance |
|---|---|---|---|---|---|---|
| 1 | SeraMag SA-1, Low streptavidin | Seradyn | 1.0 | 0.93 | 21.7% (0.5-1.6) | Round, some small fragments. |
| 2 | SeraMag SA-3, Medium streptavidin | Seradyn | 1.0 | 0.97 | 22.6% (0.5-1.4) | Round, some small fragments. |
| 3 | MagPrep | Merck | 1.0 | 0.67 | 37.5% (0.5-2.6) | Deformed fragments of many sizes |
| 4 | ProActive Microspheres Magnetic-Cl. Uniform 2.23 | Bangs | 2.23 | 2.44 | 31.1% (0.5-3.6) | Round, some small fragments many sizes |
| 5 | ProActive Microspheres Magnetic-Encapsulated 0.86 | Bangs | 0.86 | 0.63 | 40.6% (0.5-2.8) | Round + deformed fragments, many sizes |
| 6 | ProActive Microspheres Magnetic-Classical 0.83 | Bangs | 0.83 | 0.63 | 26.9% (0.5-1.7) | Round + deformed fragments, many sizes |
| 7 | Magnesphere | Promega | 0.5-1.5 | 0.86 | 43.3% (0.5-3.4) | Flakes of varying size |
| 8 | BioMag Streptavidin Ultraload | Polysciences | 1.0 | 0.67 | 32.8% (0.5-1.9) | Flakes of varying size |
| 9 | BioMag Streptavidin Nuclease Free | Polysciences | 1.0 | 0.67 | 32.4% (0.5-1.9) | Flakes of varying size |
| 10 | MagPrep | Novagen | 1.0 | 0.86/0.6 | 36.4% (0.5-2.6) | Mainly deformed, crushed particles |
| 11 | GenoPrep | GenoVision/Qiagen | unknown | 0.86 | 19.6% (0.5-1.6) | Round, some small fragments. |
| 12 | Dynabeads M270-Streptavidin | Dynal Biotech ASA | 2.8 | 2.85 | 1.24% | Monodisperse and monosized particles |
| 13 | Dynabeads M280-Streptavidin | Dynal Biotech ASA | 2.8 | 2.72 | 1.26% | Monodisperse and monosized particles |

Example 12: Nitration of Porous Polymer Particles

Porous polymer particles with a diameter of 0.45 µm were made in accordance with examples 4-6 from a low molecular weight seed particle of the disclosure.

In a 2 l glass vessel there was added 1240 gram concentrated sulfuric acid. The reactor was equipped with a jacketed glass reactor for temperature regulation and a teflon stirrer.

The acid was cooled down to 7° C. and 377 g nitric acid (65%) was added over a 15 minute interval, the reaction mixture reaching a maximum temperature of 28° C. The acid solution was cooled down to 6° C. 50 gram of dry porous polymer particles were added and the dispersion was heated to 30° C. for 90 minutes. The dispersion was then poured into 5 kg of ice-water, followed by purification of the nitrated polymer particles with water and methanol.

FTIR analysis showed strong adsorption at 1531 cm$^{-1}$ confirming the aromatic substitution of nitro groups. The reaction yield was 61.5 gram of dry nitrated particles.

Example 13: Magnetisation of Nitrated Porous Polymer Particles 300 gram dispersion of nitrated particles (4.8 weight % in water) from example 12 was added to a 0.5 liter jacketed glass reactor. 83 g of iron(II)sulfate heptahydrate and 0.11 g of manganese(II) sulfate hydrate were added. The mixture was stirred for 30 minutes to dissolve the iron salt. After 30 minutes, 116 gram 25% ammonia was added while stirring. The dispersion turned black immediately and was further heated to 60° C. and kept at 60° for 2 hours. The magnetic particles were purified with several centrifugal shifts to remove unbound magnetic material.
Purification Procedure:

The dispersion was concentrated and transferred to a 1 liter centrifugal bottle and then there was added 1 liter diluted ammonia (0.1 v % in water). The dispersion was set on a shaker to ensure a homogeneous dispersion. Then the supernatant was separated from the magnetic polymer particles by centrifugation and discarded. This procedure was repeated 5 times (* 1 liter) with diluted ammonia (0.1v %) and then 10 times (*1 liter) with purified water.

The final magnetic polymer particles contained 490 mg/g iron oxide determined by elemental analysis.

Example 14: Coating 7.5 g of magnetic particles from example 13 dispersed in 61 g diethyleneglycol dimethylether were added a 200 mL reactor. The reactor was placed in a temperature controlled water bath and equipped with a stirrer.

For a pre-coating step 1.4 gram of butanediol diglycidylether+bisphenol A diglycidylether (Araldite® LY 564) was added and the dispersion was heated to 75° C. and kept at 75° C. for 3 hours. After cooling down the solution 15.0 g butanediol diglycidylether, 6.0 g glycidol, 11.0 g glycidolmethacrylate and 6.0 g diethylene glycoldimethylether were added. The dispersion was heated to 75° C. and kept at 75° C. for 18 hours. The dispersion was purified by separating the particles from the supernatant with an external magnet, and washed 4 times with 100 mL methanol and 4 times with 100 mL methanol/isopropanol mixture (30/70 v %).

The measured yield of the coated magnetic particles was 8.8 g.

FTIR analysis confirmed the incorporation of epoxy coating and vinyl functional groups.

Example 15: Polyacrylic Acid Modified Beads 6.5 g of coated magnetic particles from example 14 were dispersed in 24.5 gram methanol/isopropanol mixture (30/70 v %) and charged in 100 mL reactor. The reactor was equipped with a stirrer, a cooler and placed in an oil bath with temperature regulation.

In a separate 50 mL beaker 0.4 gram azobisisobutyronitrile (AIBN) was dissolved in 19.9 mL methanol/isopropanol mixture (30/70v %).

The dissolved azobisisobutyronitrile and 7.8 gram acrylic acid were added to the particle dispersion, heated to 75° C. and kept at 75° C. for 19 hours.

The dispersion was purified by separating the particles from the supernatant with an external magnet, and washed 6 times with 40 mL methanol and finally dispersed in 60 mL 0.15 M sodium hydroxide solution. The dispersion was heated to 75° C. for 4 hours. The particles were purified with water by consecutive magnetic separations.

The final particle had a mode diameter of 0.5 μm with a narrow size distribution determined by disc-centrifugation. FTIR confirmed the incorporation of carboxylic acid groups and the acid content was determined to be 0.8 mmol/g dry weight by titration.

Example 16: Compact Beads With High Cross Linking 15.5 g SDS, 1290 g water, 0.1 g Synperonic™ All (a polyoxyethylene (11) C12-C15 alcohol emulsifier), 15.5 g acetone and 129 g dioctanoylperoxide were mixed with an Ultra-Turrax disperser and homogenised with a pressure homogeniser (=initiator emulsion)

503.6 g of a low molecular weight seed dispersion (4.57 w % dry content) made according to example 1 and with a measured seed diameter of 0.11 μm was gently mixed with 194.3 g of the initiator emulsion. The mixture was stirred at 25° C. for 24 hours (=activated seed particles).

30.6 g styrene, 37.0 g glycidylmethacrylate, 117.4 g divinylbenzene (comprising 65 g divinylbenzene and 45 g ethylvinylbenzene), 307 g water and 1.3 g SDS were charged to a 1 liter reactor and 268 g of the activated seed particles were added. After stirring for 4 hours at 25° C., 238 g water was charged and the temperature was raised to 60° C. and kept at 60° C. for 2 hours and further 70° C. for 5 hours.

To introduce amine functional groups 15.6 g ethylene diamine was charged to 500 ml of the particle dispersion and the mixture was heated to 80° C. and kept at 80° C. for 2 hours.

The compact polymer particles have a mode diameter of 0.3 μm measured by disc centrifugation.

Example 17: Silica Coated Submicron Monosized Magnetic Particles

Monosized 0.5 μm magnetic particles were made according to reaction scheme 1 and examples 12 and 13.

In a reactor a mixture of 2 g magnetic 0.5 μm particles and 6.3 g absolute ethanol was stirred at room temperature. Then 2.4 g tetraethyl orthosilicate, 98%, 24.0 g water and 8.0 mL ammonium solution, 28%, were charged. The mixture reacted for 18 hours at room temperature. The particles were purified by magnetic separation of the coated particles from the supernatant. The reaction yield was 26 g and FTIR analysis confirmed the presence of Si—O groups.

Example 18: Comparative Example Using High Molecular Weight Seed Particles

A high molecular weight seed ($M_w$ 4.6×10$^5$) with a diameter of 0.15 μm was used to make two porous particle dispersions with different pore volumes.

The synthesis procedure followed the same steps as outlined in example 4 but with a initiator/seed (Y/P) ratio of 1 and a monomer to polymer ratio of 35 (M/P).

SEM images showed that the resulting particles appeared cornered and not spherical, and with a broad size distribution.

Example 19: Distribution of Magnetic Material

Figure 28:
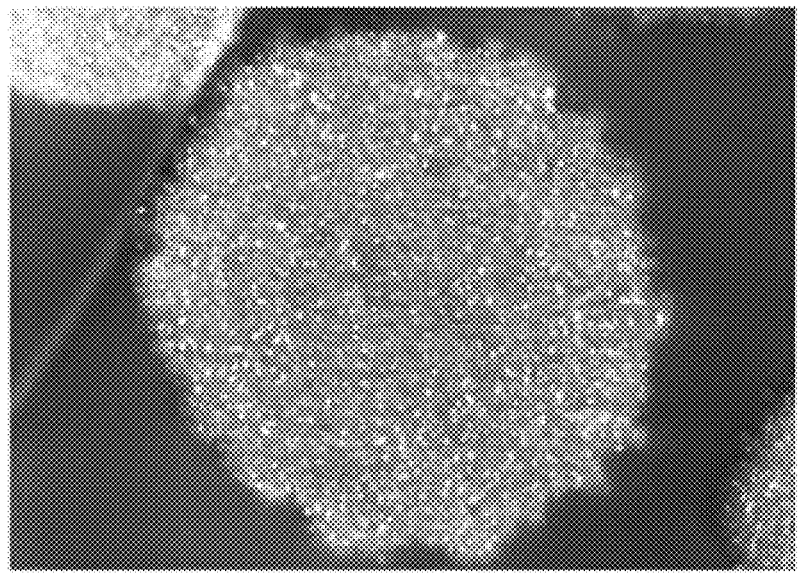
FIG. 28 shows an SEM image of a cross section of a magnetic polymer particle cast in epoxy, in which the iron oxide is visualized as bright points.

An SEM is made of a cross-section of a magnetic polymer particle made by the Ugelstad process. The particle has a diameter of 2.8 μm and therefore falls outside the scope of the invention but, nevertheless, serves to illustrate that the incorporation of magnetic material in polymer pores does not change the particle morphology. The SEM is shown in FIG. 28, where iron oxide (i.e. magnetic material) shows as bright points, illustrating how the magnetic material is dispersed throughout the interior of the particle (in pores) without clumping and without changing the external morphology.

The invention claimed is:

1. A process for the preparation of monodisperse particles for use as Ugelstad seed particles, the process comprising an emulsion polymerization process comprising:
   forming an aqueous dispersion comprising a vinylic monomer and a water soluble polymerization initiator; and
   agitating until the dispersion becomes visibly cloudy,
   wherein the aqueous dispersion comprises a surfactant and a chain transfer agent is added after the dispersion becomes visibly cloudy, such that the polymerization forms monodisperse seed particles having a z-average diameter of from 50 nm to 200 nm and, when measured by gel permeation chromatography, the polymer has a mean weight average molecular weight of more than 1,000 and less than 70,000.

2. The process of claim 1, wherein the surfactant is present below its critical micelle concentration.

3. The process of claim 1, wherein the surfactant is present in a concentration of not more than 2.5 g/L.

4. The process of claim 1, wherein the surfactant is sodium dodecyl sulfate.

5. The process of claim 1, wherein the vinylic monomer is an acrylic monomer, a styrene monomer or a methacrylate monomer.

6. The process of claim 1, wherein the chain transfer agent comprises a haloalkane.

7. The process of claim 6, wherein the haloalkane is bromotrichloromethane.

8. The process of claim 1, wherein the chain transfer agent comprises an alkylmercaptan.

9. The process of claim 8, wherein the alkylmercaptan is butyl mercaptan, isooctyl 3-mercaptopropionate or octylmercaptan.

10. The process of claim 1, wherein the addition of chain transfer agent starts about 5 to 15 minutes after the dispersion becomes visibly cloudy.

11. The process of claim 1, further comprising subjecting the monodisperse seed particles to an Ugelstad process wherein the percentage by weight of cross-linker monomer included in the total monomer used in the suspension polymerization stage of the Ugelstad process (the final polymerization stage where there are plural polymerization stages) is >25% wt cross-linker, to form submicron monodisperse particles having a z-average diameter of less than 1 μm.

12. The process of claim 11, wherein the submicron monodisperse particles are porous particles having a smooth outer surface.

13. The process of claim 11, wherein the submicron monodisperse particles have a specific surface area of from 300 m$^2$/g to 700 m$^2$/g when measured by gas adsorption analysis.

14. The process of claim 11, wherein the Ugelstad process comprises:
(i) forming an aqueous dispersion comprising
the monodisperse seed particles,
finely divided droplets comprising an organic compound of molecular weight below 5,000 and water solubility at 25° C. of less than 10-2 g/L, and
an organic solvent in which the organic compound is soluble, the organic solvent being optional when the polymer forming the seed particles has an average molecular weight which corresponds to up to 50 monomer units;
(ii) allowing the organic compound to diffuse into the monodisperse seed particles, causing the seed particles to become activated;
(iii) removing the organic solvent, where present from inside the seed particles, and contacting the activated seed particle with an aqueous vehicle containing a monomer that is at least 10 times more soluble in water than the organic compound, and a crosslinker;
(iv) allowing the monomer to diffuse into the activated seed particles to form an aqueous dispersion of swollen seed particles; and
(v) initiating polymerization of the monomer in the swollen seed particles.

15. The process of claim 1, wherein the surfactant is present in a concentration of not more than 2 g/L.

16. The process of claim 1, wherein the surfactant is present in a concentration of not more than 1.7 g/L.

17. The process of claim 1, wherein the surfactant is present in a concentration of not more than 1.5 g/L.

* * * * *